(12) United States Patent
Wang et al.

(10) Patent No.: US 9,890,188 B2
(45) Date of Patent: Feb. 13, 2018

(54) SUBSTITUTED NUCLEOSIDES, NUCLEOTIDES AND ANALOGS THEREOF

(71) Applicant: ALIOS BIOPHARMA, INC., South San Francisco, CA (US)

(72) Inventors: Guangyi Wang, Carlsbad, CA (US); David Bernard Smith, San Mateo, CA (US); Leonid Beigelman, San Mateo, CA (US); Christian Andreas Jekle, San Francisco, CA (US)

(73) Assignee: Alios BioPharma, Inc., South San Francisco, CA (US)

( * ) Notice: Subject to any disclaimer, the term of this patent is extended or adjusted under 35 U.S.C. 154(b) by 0 days.

(21) Appl. No.: 14/971,926

(22) Filed: Dec. 16, 2015

(65) Prior Publication Data

US 2016/0176910 A1   Jun. 23, 2016

Related U.S. Application Data

(60) Provisional application No. 62/094,418, filed on Dec. 19, 2014.

(51) Int. Cl.
| A01N 43/04 | (2006.01) |
| A61K 31/70 | (2006.01) |
| C07H 19/06 | (2006.01) |
| C07H 19/10 | (2006.01) |

(52) U.S. Cl.
CPC ............ *C07H 19/06* (2013.01); *C07H 19/10* (2013.01)

(58) Field of Classification Search
None
See application file for complete search history.

(56) References Cited

U.S. PATENT DOCUMENTS

| 5,432,272 | A | 7/1995 | Benner et al. |
| 7,125,855 | B2 | 10/2006 | Bhat et al. |
| 2012/0070411 | A1 | 3/2012 | Beigelman et al. |
| 2012/0070415 | A1 | 3/2012 | Beigelman et al. |
| 2012/0071434 | A1 | 3/2012 | Smith et al. |
| 2012/0149657 | A1 | 6/2012 | Secrist, III et al. |
| 2012/0165286 | A1 | 6/2012 | Beigelman et al. |
| 2013/0164261 | A1 | 6/2013 | Wang et al. |
| 2013/0165400 | A1 | 6/2013 | Beigelman et al. |
| 2013/0252920 | A1 | 9/2013 | Blatt et al. |
| 2013/0253181 | A1 | 9/2013 | Serebryany et al. |
| 2013/0281687 | A1 | 10/2013 | Serebryany et al. |
| 2014/0179627 | A1 | 6/2014 | Beigelman et al. |
| 2014/0179910 | A1 | 6/2014 | Beigelman et al. |
| 2014/0303108 | A1 | 10/2014 | Beigelman et al. |
| 2014/0303113 | A1 | 10/2014 | Krop et al. |
| 2015/0011497 | A1 | 1/2015 | Beigelman et al. |
| 2015/0038451 | A1 | 2/2015 | Smith et al. |
| 2015/0051167 | A1 | 2/2015 | Wang et al. |
| 2015/0105341 | A1 | 4/2015 | Beigelman et al. |
| 2015/0141363 | A1 | 5/2015 | Wang et al. |
| 2015/0175647 | A1 | 6/2015 | Kuldipkumar et al. |
| 2015/0183819 | A1 | 7/2015 | Beigelman et al. |
| 2015/0315228 | A1 | 11/2015 | Beigelman et al. |
| 2015/0366887 | A1 | 12/2015 | Blatt et al. |
| 2015/0366888 | A1 | 12/2015 | Blatt et al. |
| 2015/0368286 | A1 | 12/2015 | Serebryany et al. |
| 2016/0016987 | A1 | 1/2016 | Beigelman et al. |
| 2016/0022724 | A1 | 1/2016 | Chanda et al. |
| 2016/0024136 | A1 | 1/2016 | Beigelman et al. |
| 2016/0039858 | A1 | 2/2016 | Beigelman et al. |
| 2016/0039861 | A1 | 2/2016 | Smith et al. |
| 2016/0115190 | A1 | 4/2016 | Serebryany et al. |
| 2016/0176911 | A1 | 6/2016 | Beigelman et al. |
| 2016/0264610 | A1 | 9/2016 | Beigelman et al. |
| 2016/0318967 | A1 | 11/2016 | Dyatkina et al. |
| 2016/0318969 | A1 | 11/2016 | Kuldipkumar et al. |
| 2016/0331770 | A1 | 11/2016 | Beigelman et al. |
| 2017/0002037 | A1 | 1/2017 | Beigelman et al. |
| 2017/0037075 | A1 | 2/2017 | Beigelman et al. |
| 2017/0037077 | A1 | 2/2017 | Beigelman et al. |
| 2017/0143749 | A1 | 5/2017 | Blatt et al. |
| 2017/0143751 | A1 | 5/2017 | Blatt et al. |

FOREIGN PATENT DOCUMENTS

| EP | 1404347 | 1/2006 | |
| EP | 2177527 | 4/2010 | |
| WO | WO 00/69876 | 11/2000 | |
| WO | WO 2009/067409 | 5/2009 | |
| WO | WO 2010/030858 | 3/2010 | |
| WO | WO 2010/108140 | 9/2010 | |
| WO | WO 2013/096679 A1 * | 6/2013 | ............ C07H 19/06 |
| WO | WO 2013/142124 | 9/2013 | |
| WO | WO 2013/142159 | 9/2013 | |
| WO | WO 2013/142525 | 9/2013 | |
| WO | WO 2014/100498 | 6/2014 | |

(Continued)

OTHER PUBLICATIONS

Kitano et al. Tetrahedron (1997), vol. 53, pp. 13315-13322.*
Matsuda et al. Cancer Sci. (2004), vol. 95, pp. 105-111.*
Pollard et al. Biochemistry (1973), vol. 12, pp. 1063-1066.*
Second Written Opinion dated Nov. 15, 2016 for PCT Application No. PCT/US2015/066193 filed Dec. 16, 2015.
Kitano et al., "Synthesis of Novel 4'-C-Methyl-Pyrimidine Nucleosides and Their Biological Activities" Bioorganic & Medicinal Chemistry Letters (1999) 9:827-830.
Ohrui, H., "4'-C-ethynyl-2'-deoxynucleosides," Chapter 16, Modified Nucleosides in Biochemistry, Biotechnology and Medicine, 2008, (ed. P. Herdewjin) Wiley-Vch Verlag GmBH & Co. KGaA, pp. 425-431.
Tiwari et al., "Synthesis and Anticancer Evaluation of 4'-C-Methyl-2'-Fluoro-Arabino Nucleosides" Nucleosides, Nucleotides & Nucleic Acids (2009) 28:657-677.
Waga et al., "Synthesis and Biological Evaluation of 4'-C-Methyl Nucleosides" Nucleosides & Nucleotides (1996) 15(1-3):287-304.

(Continued)

*Primary Examiner* — Patrick T Lewis
(74) *Attorney, Agent, or Firm* — Knobbe, Martens, Olson & Bear, LLP

(57) ABSTRACT

Disclosed herein are nucleosides, nucleotides and nucleotide analogs, methods of synthesizing the same and methods of treating diseases and/or conditions such as a Picornavirus infection with one or more nucleosides, nucleotides and nucleotide analogs.

38 Claims, No Drawings

(56) References Cited

FOREIGN PATENT DOCUMENTS

| WO | WO 2014/134251 | 9/2014 |
|---|---|---|
| WO | WO 2014/164533 | 10/2014 |
| WO | WO 2014/209983 | 12/2014 |
| WO | WO 2015/054465 | 4/2015 |
| WO | WO 2015/120237 | 8/2015 |
| WO | WO 2015/200205 | 12/2015 |
| WO | WO 2015/200219 | 12/2015 |
| WO | WO 2016/022464 | 2/2016 |

OTHER PUBLICATIONS

Wang et al., "Synthesis and anti-HIV activity of 2'-deoxy-2'-fluoro-4'-C-ethynyl nucleoside analogs" Bioorganic & Medicinal Chemistry Letters (2010) 20:4053-4056.

International Search Report and Written Opinion dated Mar. 16, 2016 for PCT Application No. PCT/US2015/066193, filed Dec. 16, 2015.

Chen et al., "A general synthesis of specifically deuterated nucleotides for studies of DNA and RNA" Bioorg. Med. Chem. Lett. (2002) 12(21):3093-3096.

Greene, et al., Protective Groups in Organic Synthesis, 3. Ed., John Wiley & Sons, (1999) Cover & Contents pages.

"IUPAC-IUB Commission on Biochemical Nomenclature Abbreviated Nomenclature of Synthetic Polypeptides (Polymerized Amino Acids)* Revised Recommendations (1971)" *Biochem*istry. (1972) 11(5):942-944.

Kitano et al., "Synthesis of 4'-C-fluoromethylnucleosides as potential antineoplastic agents" Tetrahedron (1997) 53(39):13315-13322.

McOmie, J. F. W., Protective Groups in Organic Chemistry, Plenum Press, 1973. Cover & Contents pages only.

Wang et al., "Discovery of 4'-Chloromethyl-2'-deoxy-3',5'-di-O-isobutyryl-2'-fluorocytidine (ALS-8176), A First-in-Class RSV Polymerase Inhibitor for Treatment of Human Respiratory Syncytial Virus Infection"J. Med. Chem. (2015) 58(4):1862-1878.

Renis et al., "Nucleic Acids. III. Antiviral Activity of Nucleotides and Dinucleotide Phosphate Containing ara-Cytidine" J. Med. Chem. (1967) 10:777-782.

Wecher, W., "Nucleic Acids. I. Antiviral Activity of Nucleotides and Dinucleotide Phosphate Containing ara-Cytidine" J. Med. Chem. (1967) 10:762-773.

Third Written Opinion dated Feb. 9, 2017 for PCT Application No. PCT/US2015/066193 filed Dec. 16, 2015.

International Preliminary Report on Patentability dated Apr. 13, 2017 for PCT Application No. PCT/US2015/066193 filed Dec. 16, 2015.

* cited by examiner

1

SUBSTITUTED NUCLEOSIDES, NUCLEOTIDES AND ANALOGS THEREOF

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6.

BACKGROUND

Field

The present application relates to the fields of chemistry, biochemistry and medicine. More particularly, disclosed herein are nucleotide analogs, pharmaceutical compositions that include one or more nucleosides and/or nucleotide analogs and methods of synthesizing the same. Also disclosed herein are methods of treating diseases and/or conditions with a nucleoside and/or a nucleotide analog, alone or in combination therapy with one or more other agents.

Description

Nucleoside analogs are a class of compounds that have been shown to exert antiviral and anticancer activity both in vitro and in vivo, and thus, have been the subject of widespread research for the treatment of viral infections. Nucleoside analogs are usually therapeutically inactive compounds that are converted by host or viral enzymes to their respective active anti-metabolites, which, in turn, may inhibit polymerases involved in viral or cell proliferation. The activation occurs by a variety of mechanisms, such as the addition of one or more phosphate groups and, or in combination with, other metabolic processes.

SUMMARY

Some embodiments disclosed herein relate to a compound of Formula (I), or a pharmaceutically acceptable salt thereof.

Some embodiments disclosed herein relate to a method of ameliorating and/or treating a picornavirus infection that can include administering to a subject identified as suffering from the picornavirus infection an effective amount of one or more compounds of Formula (I), or a pharmaceutically acceptable salt thereof, or a pharmaceutical composition that includes one or more compounds of Formula (I), or a pharmaceutically acceptable salt thereof. Other embodiments described herein relate to using one or more compounds of Formula (I), or a pharmaceutically acceptable salt thereof, in the manufacture of a medicament for ameliorating and/or treating a picornavirus infection. Still other embodiments described herein relate to one or more compounds of Formula (I), or a pharmaceutically acceptable salt thereof, or a pharmaceutical composition that includes one or more compounds of Formula (I), or a pharmaceutically acceptable salt thereof, that can be used for ameliorating and/or treating a picornavirus infection.

Some embodiments disclosed herein relate to a method of ameliorating and/or treating a picornavirus infection that can include contacting a cell infected with the picornavirus with an effective amount of one or more compounds described herein (for example, a compound of Formula (I), or a pharmaceutically acceptable salt thereof), or a pharmaceutical composition that includes one or more compounds described herein, or a pharmaceutically acceptable salt thereof. Other embodiments described herein relate to using one or more compounds described herein (for example, a compound of Formula (I), or a pharmaceutically acceptable salt thereof) in the manufacture of a medicament for ameliorating and/or treating a picornavirus infection that can include contacting a cell infected with the picornavirus with an effective amount of said compound(s). Still other embodiments described herein relate to one or more compounds described herein (for example, a compound of Formula (I), or a pharmaceutically acceptable salt thereof), or a pharmaceutical composition that includes one or more compounds described herein, or a pharmaceutically acceptable salt thereof, that can be used for ameliorating and/or treating a picornavirus infection by contacting a cell infected with the picornavirus with an effective amount of said compound(s).

Some embodiments disclosed herein relate to a method of inhibiting replication of a picornavirus that can include contacting a cell infected with the picornavirus with an effective amount of one or more compounds described herein (for example, a compound of Formula (I), or a pharmaceutically acceptable salt thereof), or a pharmaceutical composition that includes one or more compounds described herein, or a pharmaceutically acceptable salt thereof. Other embodiments described herein relate to using one or more compounds described herein (for example, a compound of Formula (I), or a pharmaceutically acceptable salt thereof) in the manufacture of a medicament for inhibiting replication of a picornavirus that can include contacting a cell infected with the picornavirus with an effective amount of said compound(s). Still other embodiments described herein relate to one or more compounds described herein (for example, a compound of Formula (I), or a pharmaceutically acceptable salt thereof), or a pharmaceutical composition that includes one or more compounds described herein, or a pharmaceutically acceptable salt thereof, that can be used for inhibiting replication of a picornavirus by contacting a cell infected with the picornavirus with an effective amount of said compound(s). In some embodiments, the picornavirus can be selected from a rhinovirus, hepatitis A virus, a coxasackie virus and an enterovirus.

DETAILED DESCRIPTION

The viruses within the Picornaviridae family are non-enveloped, positive sense, single-stranded, spherical RNA viruses with an icosahedral capsid. Picornavirus genomes are approximately 7-8 kilobases long and have an IRES (Internal Ribosomal Entry Site). These viruses are polyadenylated at the 3' end, and has a VPg protein at the 5' end in place of a cap. Genera within the Picornaviridae family include Aphthovirus, Aquamavirus, Avihepatovirus, Cardiovirus, Cosavirus, Dicipivirus, Enterovirus, Erbovirus, Hepatovirus, Kobuvirus, Megrivirus, Parechovirus, Rhinovirus, Salivirus, Sapelovirus, Senecavirus, Teschovirus and Tremovirus.

Enteroviruses are transmitted through the fecal-oral route and/or via aerosols of respiratory droplets, and are highly communicable. The genus of Enterovirus includes several species, including: enterovirus A, enterovirus B, enterovirus C, enterovirus D, enterovirus E, enterovirus F, enterovirus G, enterovirus Henterovirus J, rhinovirus A, rhinovirus B and rhinovirus C. Within a species of the aforementioned enteroviruses are the following serotypes: polioviruses, rhinoviruses, coxsackieviruses, echoviruses and enterovirus.

Rhinoviruses are the cause of the common cold. Rhinoviruses are named because of their transmission through the respiratory route and replication in the nose. A person can be infected with numerous rhinoviruses over their lifetime because immunity develops for each serotype. Thus, each serotype can cause a new infection.

A hepatitis A infection is the result of an infection with a Hepatitis A virus. Hepatovirus is transmitted through the fecal-oral route. Transmission can occur via person-to-person by ingestion of contaminated food or water, or through direct contact with an infectious person.

Parechovirus include human parechovirus 1 (echovirus 22), human parechovirus 2 (echovirus 23), human parechovirus 3, human parechovirus 4, human parechovirus 5 and human parechovirus 6.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein, any "R" group(s) such as, without limitation, $R^{1A}$, $R^{2A}$, $R^{3A}$, $R^{4A}$, $R^{5A}$, $R^{6A}$, $R^{7A}$, $R^{8A}$, $R^{9A}$, $R^{10A}$, $R^{11A}$, $R^{12A}$, $R^{13A}$, $R^{14A}$, $R^{15A}$, $R^{16A}$, $R^{17A}$, $R^{18A}$, $R^{19A}$, $R^{20A}$, $R^{21A}$, $R^{22A}$, $R^{23A}$, $R^{24A}$, $R^{25A}$, $R^{26A}$, $R^{27A}$, $R^{28A}$, $R^{29A}$, $R^{30A}$, $R^{31A}$, $R^{32A}$, $R^{33A}$, $R^{34A}$, $R^{35A}$, $R^{36A}$, $R^{37A}$ and $R^{38A}$ represent substituents that can be attached to the indicated atom. An R group may be substituted or unsubstituted. If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded to one another to form a ring:

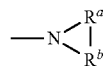

In addition, if two "R" groups are described as being "taken together" with the atom(s) to which they are attached to form a ring as an alternative, the R groups are not limited to the variables or substituents defined previously.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, aryl, heteroaryl, heterocyclyl, aryl(alkyl), heteroaryl(alkyl), heterocyclyl(alkyl), hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, azido, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heteroalicyclyl group. That is, the alkyl, alkenyl, alkynyl, ring(s) of the cycloalkyl, ring(s) of the cycloalkenyl, ring(s) of the aryl, ring(s) of the heteroaryl or ring(s) of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocyclyl or a heteroalicyclyl may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and 3,4-methylenedioxyphenyl).

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to, benzyl, 2-phenyl(alkyl), 3-phenyl(alkyl) and naphthyl(alkyl).

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl) and their benzo-fused analogs.

A "heteroalicyclyl(alkyl)" and "heterocyclyl(alkyl)" refer to a heterocyclic or a heteroalicylylic group connected, as a substituent, via a lower alkylene group. The lower alkylene and heterocyclyl of a heteroalicyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl (methyl), and 1,3-thiazinan-4-yl(methyl).

"Lower alkylene groups" are straight-chained —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) connected, as substituents, via a carbonyl group. Examples include formyl, acetyl, propanoyl, benzoyl and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

A "sulfenyl" group refers to an "—SR" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "X$_3$CSO$_2$—" group wherein each X is a halogen.

A "trihalomethanesulfonamido" group refers to an "X$_3$CS(O)$_2$N(R$_A$)—" group wherein each X is a halogen, and R$_A$ hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl).

The term "amino" as used herein refers to a —NH$_2$ group.

As used herein, the term "hydroxy" refers to a —OH group.

A "cyano" group refers to a "—CN" group.

The term "azido" as used herein refers to a —N$_3$ group.

An "isocyanato" group refers to a "—NCO" group.

A "thiocyanato" group refers to a "—CNS" group.

An "isothiocyanato" group refers to an "—NCS" group.

A "carbonyl" group refers to a C=O group.

An "S-sulfonamido" group refers to a "—SO$_2$N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An S-sulfonamido may be substituted or unsubstituted.

An "N-sulfonamido" group refers to a "RSO$_2$N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-sulfonamido may be substituted or unsubstituted.

An "O-carbamyl" group refers to a "—OC(=O)N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-carbamyl may be substituted or unsubstituted.

An "N-carbamyl" group refers to an "ROC(=O)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-carbamyl may be substituted or unsubstituted.

An "O-thiocarbamyl" group refers to a "—OC(=S)—N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-thiocarbamyl may be substituted or unsubstituted.

An "N-thiocarbamyl" group refers to an "ROC(=S)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-thiocarbamyl may be substituted or unsubstituted.

A "C-amido" group refers to a "—C(=O)N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A C-amido may be substituted or unsubstituted.

An "N-amido" group refers to a "RC(=O)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-amido may be substituted or unsubstituted.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "nucleoside" is used herein in its ordinary sense as understood by those skilled in the art, and refers to a compound composed of an optionally substituted pentose moiety or modified pentose moiety attached to a heterocyclic base or tautomer thereof via a N-glycosidic bond, such as attached via the 9-position of a purine-base or the 1-position of a pyrimidine-base. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers. In some instances, the nucleoside can be a nucleoside analog drug.

The term "nucleotide" is used herein in its ordinary sense as understood by those skilled in the art, and refers to a nucleoside having a phosphate ester bound to the pentose moiety, for example, at the 5'-position.

As used herein, the term "heterocyclic base" refers to an optionally substituted nitrogen-containing heterocyclyl that can be attached to an optionally substituted pentose moiety or modified pentose moiety. In some embodiments, the heterocyclic base can be selected from an optionally substituted purine-base, an optionally substituted pyrimidine-base and an optionally substituted triazole-base (for example, a 1,2,4-triazole). The term "purine-base" is used herein in its ordinary sense as understood by those skilled in the art, and includes its tautomers. Similarly, the term "pyrimidine-base" is used herein in its ordinary sense as understood by those skilled in the art, and includes its tautomers. A non-limiting list of optionally substituted purine-bases includes purine, adenine, guanine, hypoxanthine, xanthine, alloxanthine, 7-alkylguanine (e.g. 7-methylguanine), theobromine, caffeine, uric acid and isoguanine. Examples of pyrimidine-bases include, but are not limited to, cytosine, thymine, uracil, 5,6-dihydrouracil and 5-alkylcytosine (e.g., 5-methylcytosine). An example of an optionally substituted triazole-base is 1,2,4-triazole-3-carboxamide. Other non-limiting examples of heterocyclic bases include diaminopurine, 8-oxo-$N^6$-alkyladenine (e.g., 8-oxo-$N^6$-methyladenine), 7-deazaxanthine, 7-deazaguanine, 7-deazaadenine, $N^4,N^4$-ethanocytosin, $N^6,N^6$-ethano-2,6-diaminopurine, 5-halouracil (e.g., 5-fluorouracil and 5-bromouracil), pseudoisocytosine, isocytosine, isoguanine, and other heterocyclic bases described in U.S. Pat. Nos. 5,432,272 and 7,125,855, which are incorporated herein by reference for the limited purpose of disclosing additional heterocyclic bases. In some embodiments, a heterocyclic base can be optionally substituted with an amine or an enol protecting group(s).

The term "—N-linked amino acid" refers to an amino acid that is attached to the indicated moiety via a main-chain amino or mono-substituted amino group. When the amino acid is attached in an —N-linked amino acid, one of the hydrogens that is part of the main-chain amino or mono-substituted amino group is not present and the amino acid is attached via the nitrogen. N-linked amino acids can be substituted or unsubstituted.

The term "—N-linked amino acid ester derivative" refers to an amino acid in which a main-chain carboxylic acid group has been converted to an ester group. In some embodiments, the ester group has a formula selected from alkyl-O—C(=O)—, cycloalkyl-O—C(=O)—, aryl-O—C(=O)— and aryl(alkyl)-O—C(=O)—. A non-limiting list of ester groups include substituted and unsubstituted versions of the following: methyl-O—C(=O)—, ethyl-O—C(=O)—, n-propyl-O—C(=O)—, isopropyl-O—C(=O)—, n-butyl-O—C(=O)—, isobutyl-O—C(=O)—, tert-butyl-O—C(=O)—, neopentyl-O—C(=O)—, cyclopropyl-O—C(=O)—, cyclobutyl-O—C(=O)—, cyclopentyl-O—C(=O)—, cyclohexyl-O—C(=O)—, phenyl-O—C(=O)—, benzyl-O—C(=O)—, and naphthyl-O—C(=O)—. N-linked amino acid ester derivatives can be substituted or unsubstituted.

The term "—O-linked amino acid" refers to an amino acid that is attached to the indicated moiety via the hydroxy from its main-chain carboxylic acid group. When the amino acid is attached in an —O-linked amino acid, the hydrogen that is part of the hydroxy from its main-chain carboxylic acid group is not present and the amino acid is attached via the oxygen. O-linked amino acids can be substituted or unsubstituted.

As used herein, the term "amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine.

The term "interferon" is used herein as is commonly understood by one of ordinary skill in the art. Several types of interferons are known to those skilled in the art, such as Type I interferons, Type 2 interferons and Type 3 interferons. A non-limiting list of examples include: alpha-interferons, beta-interferons, delta-interferons, gamma interferons, lambda interferons, omega-interferons, tau-interferons, x-interferons, consensus interferons and asialo-interferons. Interferons can be pegylated. Examples of type 1 interferons include interferon alpha 1A, interferon alpha 1B, interferon alpha 2A, interferon alpha 2B, pegylated-interferon alpha 2a (PEGASYS, Roche), recombinant interferon alpha 2a (ROFERON, Roche), inhaled interferon alpha 2b (AERX, Aradigm), pegylated-interferon alpha 2b (ALBUFERON, Human Genome Sciences/Novartis, PEGINTRON, Schering), recombinant interferon alpha 2b (INTRON A, Schering), pegylated interferon alpha 2b (PEG-INTRON, Schering, VIRAFERONPEG, Schering), interferon beta-1a (REBIF, Serono, Inc. and Pfizer), consensus interferon alpha (INFERGEN, Valeant Pharmaceutical). Examples of type 2 interferons include interferon gamma 1, interferon gamma 2 and pegylated interferon gamma; and examples of type 3 interferons include interferon lambda 1, interferon lambda 2 and interferon lambda 3.

The terms "phosphorothioate" and "phosphothioate" refer to a compound of the general formula

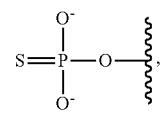

its protonated forms

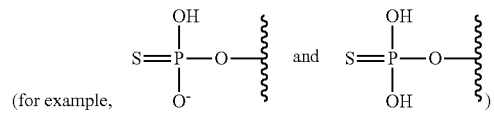 [SMILES: *OP([O-])(O)=S ; *OP(O)(O)=S]

(for example,                          and                          )

and its tautomers

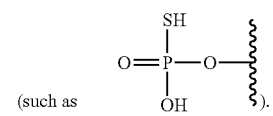

(such as                          ).

As used herein, the term "phosphate" is used in its ordinary sense as understood by those skilled in the art, and includes its protonated forms

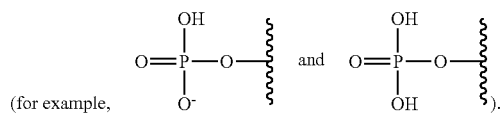 [SMILES: *OP(=O)([O-])O ; *OP(=O)(O)O]

(for example,                          and                          ).

As used herein, the terms "monophosphate," "diphosphate," and "triphosphate" are used in their ordinary sense as understood by those skilled in the art, and include protonated forms.

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4''-trimethoxytrityl (TMTr); and those described herein).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' preferred, 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included. For example all tautomers of a phosphate and a phosphorothioate groups are intended to be included. Examples of tautomers of a phosphorothioate include the following:

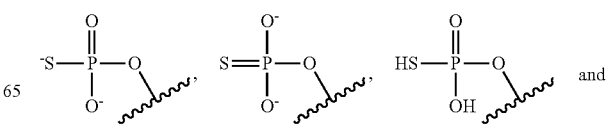

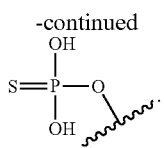

Furthermore, all tautomers of heterocyclic bases known in the art are intended to be included, including tautomers of natural and non-natural purine-bases and pyrimidine-bases.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Compounds

Some embodiments disclosed herein relate to a compound of Formula (I), or a pharmaceutically acceptable salt thereof:

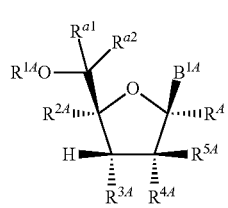

(I)

wherein: $B^{1A}$ can be an optionally substituted heterocyclic base or an optionally substituted heterocyclic base with a protected amino group; $R^A$ can be hydrogen or deuterium; $R^{1A}$ can be selected from hydrogen, an optionally substituted acyl, an optionally substituted O-linked amino acid,

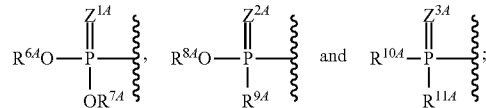

$R^{a1}$ and $R^{a2}$ can be independently hydrogen or deuterium; $R^{2A}$ can be an unsubstituted $C_{1-4}$ alkyl, an unsubstituted $C_{2-4}$ alkenyl, an unsubstituted $C_{2-4}$ alkynyl, a $C_{1-6}$ haloalkyl, a $C_{1-6}$ azidoalkyl or a $C_{1-6}$ aminoalkyl; $R^{3A}$ can be selected from hydrogen, deuterium, halo, OH, —OC(=O)$R^{n4}$ and an optionally substituted O-linked amino acid; $R^{4A}$ can be hydrogen or deuterium; $R^{5A}$ can be hydrogen, deuterium, halogen, $N_3$, OH, an optionally substituted $C_{1-6}$ alkyl, an optionally substituted $C_{2-6}$ alkenyl and an optionally substituted $C_{2-6}$ alkynyl; $R^{6A}$, $R^{7A}$ and $R^{8A}$ can be independently selected from absent, hydrogen, an optionally substituted $C_{1-24}$ alkyl, an optionally substituted $C_{3-24}$ alkenyl, an optionally substituted $C_{3-24}$ alkynyl, an optionally substituted $C_{3-6}$ cycloalkyl, an optionally substituted $C_{3-6}$ cycloalkenyl, an optionally substituted aryl, an optionally substituted heteroaryl, an optionally substituted aryl($C_{1-6}$ alkyl), an optionally substituted *—(CR$^{15A}$R$^{16A}$)$_p$—O—C$_{1-24}$ alkyl, an optionally substituted *—(CR$^{17A}$R$^{18A}$)$_q$—O—C$_{1-24}$ alkenyl,

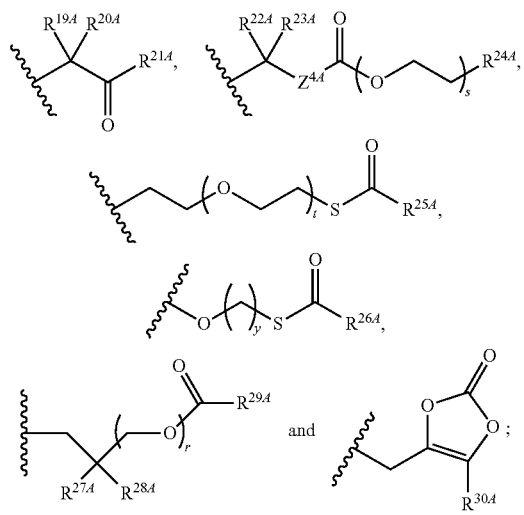

or $R^{6A}$ can be

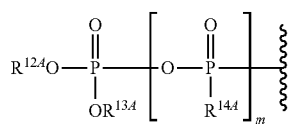

and $R^{7A}$ can be absent or hydrogen; or $R^{6A}$ and $R^{7A}$ can be taken together to form a moiety selected from the group consisting of an optionally substituted

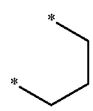 [SMILES: *CCC*]

and an optionally substituted

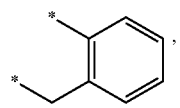, wherein the oxygens connected to $R^{6A}$ and $R^{7A}$, the phosphorus and the moiety form a six-membered to ten-membered ring system; $R^{9A}$ can be independently selected from an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, NR an optionally substituted N-linked amino acid and an optionally substituted N-linked amino acid ester derivative; $R^{10A}$ and $R^{11A}$ can be independently an optionally substituted N-linked amino acid or an optionally substituted N-linked amino acid ester derivative; $R^{12A}$ and $R^{13A}$ can be independently absent or hydrogen; $R^{14A}$ can be O$^-$, OH or methyl; each $R^{15A}$, each $R^{16A}$, each $R^{17A}$ and each $R^{18A}$ can be independently hydrogen, an optionally substituted $C_{1-24}$ alkyl or alkoxy; $R^{19A}$, $R^{20A}$, $R^{22A}$ and $R^{23A}$ can be independently selected from hydrogen, an optionally substituted $C_{1-24}$ alkyl and an optionally substituted aryl; $R^{21A}$ and $R^{24A}$ can be independently selected from hydrogen, an optionally substituted $C_{1-24}$ alkyl, an optionally substituted aryl, an optionally substituted —O—$C_{1-24}$ alkyl, an optionally substituted —O-aryl an optionally substituted —O-heteroaryl, an optionally substituted —O-monocyclic heterocyclyl and

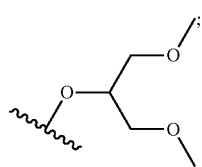 [SMILES: *OC(COC)COC];

$R^{25A}$, $R^{26A}$, $R^{30A}$ can be independently selected from hydrogen, an optionally substituted $C_{1-24}$ alkyl and an optionally substituted aryl; $R^{27A}$ and $R^{28A}$ can be independently —C≡N or an optionally substituted substituent selected from the group consisting of $C_{2-8}$ organylcarbonyl, $C_{2-8}$ alkoxycarbonyl and $C_{2-8}$ organylaminocarbonyl; $R^{29A}$ can be selected from hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl; $R^{31A}$ and $R^{32A}$ can be independently selected from hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl and an optionally substituted aryl ($C_{1-4}$ alkyl); $R^{mA}$ can be an optionally substituted $C_{1-24}$ alkyl; m and t can be independently 0 or 1; p and q can be independently selected from 1, 2 and 3; s can be 0, 1, 2 or 3; r and u can be independently 1 or 2; y can be 3, 4 or 5; and $Z^{1A}$, $Z^{2A}$, $Z^{3A}$ and $Z^{4A}$ can be independently O (oxygen) or S (sulfur).

In some embodiments, $R^{1A}$ can be

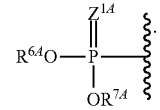

In some embodiments, $R^{6A}$ and $R^{7A}$ can be both hydrogen. In other embodiments, $R^{6A}$ and $R^{7A}$ can be both absent. In still other embodiments, at least one $R^{6A}$ and $R^{7A}$ can be absent. In yet still other embodiments, at least one $R^{6A}$ and $R^{7A}$ can be hydrogen. Those skilled in the art understand that when $R^{6A}$ and/or $R^{7A}$ are absent, the associated oxygen(s) will have a negative charge. For example, when $R^{6A}$ is absent, the oxygen associated with $R^{6A}$ will have a negative charge. In some embodiments, $Z^{1A}$ can be O (oxygen). In other embodiments, $Z^{1A}$ can be S (sulfur). In some embodiments, $R^{1A}$ can be a monophosphate. In other embodiments, $R^{1A}$ can be a monothiophosphate.

In some embodiments, when $R^{1A}$ is

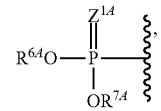

one of $R^{6A}$ and $R^{7A}$ can be hydrogen, and the other of $R^{6A}$ and $R^{7A}$ can be selected from an optionally substituted $C_{1-24}$ alkyl, an optionally substituted $C_{3-24}$ alkenyl, an optionally substituted $C_{3-24}$ alkynyl, an optionally substituted $C_{3-6}$ cycloalkyl, an optionally substituted $C_{3-6}$ cycloalkenyl, an optionally substituted aryl, an optionally substituted heteroaryl and an optionally substituted aryl($C_{1-6}$ alkyl). In some embodiments, one of $R^{6A}$ and $R^{7A}$ can be hydrogen, and the other of $R^{6A}$ and $R^{7A}$ can be an optionally substituted $C_{1-24}$ alkyl. In other embodiments, both $R^{6A}$ and $R^{7A}$ can be independently selected from an optionally substituted $C_{1-24}$ alkyl, an optionally substituted $C_{3-24}$ alkenyl, an optionally substituted $C_{3-24}$ alkynyl, an optionally substituted $C_{3-6}$ cycloalkyl, an optionally substituted $C_{3-6}$ cycloalkenyl, an optionally substituted aryl, an optionally substituted heteroaryl and an optionally substituted aryl($C_{1-6}$ alkyl). In some embodiments, both $R^{6A}$ and $R^{7A}$ can be an optionally substituted $C_{1-24}$ alkyl. In other embodiments, both $R^{6A}$ and $R^{7A}$ can be an optionally substituted $C_{3-24}$ alkenyl. In some embodiments, $R^{6A}$ and $R^{7A}$ can be independently an optionally substituted version of the following: myristoleyl, myristyl, palmitoleyl, palmityl, sapienyl, oleyl, elaidyl, vaccenyl, linoleyl, α-linolenyl, arachidonyl, eicosapentaenyl, erucyl, docosahexaenyl, caprylyl, capryl, lauryl, stearyl, arachidyl, behenyl, lignoceryl and cerotyl.

In some embodiments, at least one of $R^{6A}$ and $R^{7A}$ can be *—(CR$^{15A}$R$^{16A}$)$_p$—O—$C_{1-24}$ alkyl. In other embodiments, $R^{6A}$ and $R^{7A}$ can be both *—(CR$^{15A}$R$^{16A}$)$_p$—O—$C_{1-24}$ alkyl. In some embodiments, each $R^{15A}$ and each $R^{16A}$ can be hydrogen. In other embodiments, at least one of $R^{15A}$ and $R^{16A}$ can be an optionally substituted $C_{1-24}$ alkyl. In other embodiments, at least one of $R^{15A}$ and $R^{16A}$ can be an alkoxy (for example, benzoxy). In some embodiments, p can be 1. In other embodiments, p can be 2. In still other embodiments, p can be 3.

In some embodiments, at least one of $R^{6A}$ and $R^{7A}$ can be *—$(CR^{17A}R^{18A})_q$—O—$C_{2-24}$ alkenyl. In other embodiments, $R^{6A}$ and $R^{7A}$ can be both *—$(CR^{17A}R^{18A})_q$—O—$C_{2-24}$ alkenyl. In some embodiments, each $R^{17A}$ and each $R^{18A}$ can be hydrogen. In other embodiments, at least one of $R^{17A}$ and $R^{18A}$ can be an optionally substituted $C_{1-24}$ alkyl. In some embodiments, q can be 1. In other embodiments, q can be 2. In still other embodiments, q can be 3. When at least one of $R^{6A}$ and $R^{7A}$ is *—$(CR^{15A}R^{16A})_p$—O—$C_{1-24}$ alkyl or *—$(CR^{17A}R^{18A})_q$—O—$C_{2-24}$ alkenyl, the $C_{1-24}$ alkyl can be selected from caprylyl, capryl, lauryl, myristyl, palmityl, stearyl, arachidyl, behenyl, lignoceryl, and cerotyl, and the $C_{2-24}$ alkenyl can be selected from myristoleyl, palmitoleyl, sapienyl, oleyl, elaidyl, vaccenyl, linoleyl, α-linolenyl, arachidonyl, eicosapentaenyl, erucyl and docosahexaenyl.

In some embodiments, when $R^{1A}$ is

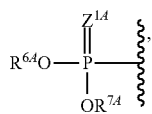

at least one of $R^{6A}$ and $R^{7A}$ can be selected from

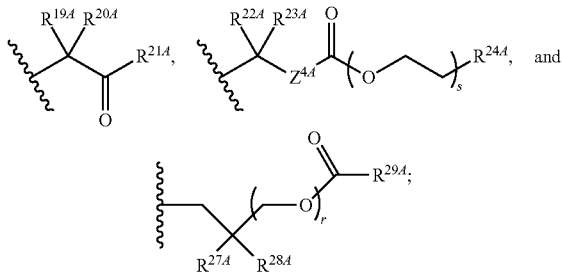

and the other of $R^{6A}$ and $R^{7A}$ can be selected from absent, hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, an optionally substituted aryl, an optionally substituted heteroaryl and an optionally substituted aryl($C_{1-6}$ alkyl).

In some embodiments, at least one of $R^{6A}$ and $R^{7A}$ can be

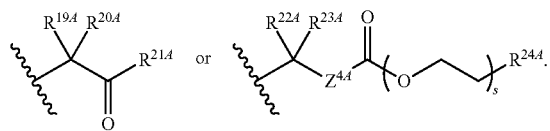

In some embodiments, at least one of $R^{6A}$ and $R^{7A}$ can be

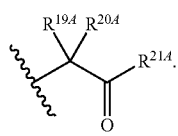

When one or both of $R^{6A}$ and $R^{7A}$ are

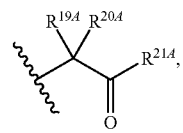

$R^{19A}$ and $R^{20A}$ can be independently selected from hydrogen, an optionally substituted $C_{1-24}$ alkyl and an optionally substituted aryl; and $R^{21A}$ can be selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl, an optionally substituted —O-monocyclic heterocyclyl and

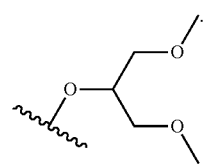 [SMILES: *OC(COC)COC]

In some embodiments, $R^{19A}$ and $R^{20A}$ can be hydrogen. In other embodiments, at least one of $R^{19A}$ and $R^{20A}$ can be an optionally substituted $C_{1-24}$ alkyl or an optionally substituted aryl. In some embodiments, $R^{21A}$ can be an optionally substituted $C_{1-24}$ alkyl. In other embodiments, $R^{21A}$ can be an optionally substituted aryl. In still other embodiments, $R^{21A}$ can be an optionally substituted —O—$C_{1-24}$ alkyl or an optionally substituted —O-aryl. In some embodiments, $R^{21A}$ can be an optionally substituted —O—$C_{1-24}$ alkyl, an optionally substituted —O-aryl, an optionally substituted —O-heteroaryl or an optionally substituted —O-monocyclic heterocyclyl.

In some embodiments, both $R^{6A}$ and $R^{7A}$ can be

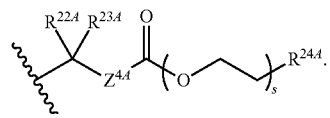

When one or both of $R^{6A}$ and $R^{7A}$ are

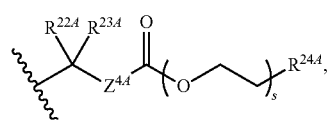

$R^{22A}$ and $R^{23A}$ can be independently selected from hydrogen, an optionally substituted $C_{1-24}$ alkyl and an optionally substituted aryl; $R^{24A}$ can be independently selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl, an optionally substituted —O-monocyclic heterocyclyl and

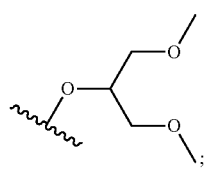 [SMILES: *OC(COC)COC]

and $Z^{4A}$ can be independently O (oxygen) or S (sulfur). In some embodiments, $R^{22A}$ and $R^{23A}$ can be hydrogen. In other embodiments, at least one of $R^{22A}$ and $R^{23A}$ can be an optionally substituted $C_{1-24}$ alkyl or an optionally substituted aryl. In some embodiments, $R^{24A}$ can be an optionally substituted $C_{1-24}$ alkyl. In other embodiments, $R^{24A}$ can be an optionally substituted aryl. In still other embodiments, $R^{24A}$ can be an optionally substituted —O—$C_{1-24}$ alkyl, an optionally substituted —O-aryl, an optionally substituted —O-heteroaryl or an optionally substituted —O-monocyclic heterocyclyl. In yet still other embodiments, $R^{24A}$ can be

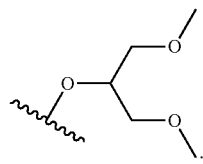 [SMILES: *OC(COC)COC]

In some embodiments, $Z^{4A}$ can be O (oxygen). In other embodiments, $Z^{4A}$ can be or S (sulfur). In some embodiments, s can be 0. In other embodiments, s can be 1. In still other embodiments, s can be 2. In yet still embodiments, s can be 3. In some embodiments, s can be 0, and $R^{24A}$ can be

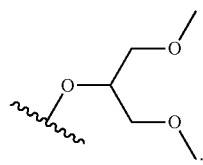 [SMILES: *OC(COC)COC]

In some embodiments, u can be 1. In other embodiments, u can be 2. In some embodiments, one or both of $R^{6A}$ and $R^{7A}$ can be isopropyloxycarbonyloxymethyl (POC). In some embodiments, one or both of $R^{6A}$ and $R^{7A}$ can be pivaloyloxymethyl (POM). In some embodiments, $R^{6A}$ and $R^{7A}$ can be both a isopropyloxycarbonyloxymethyl group, and form a bis(isopropyloxycarbonyloxymethyl) (bis(POC)) prodrug. In some embodiments, $R^{6A}$ and $R^{7A}$ can be both a pivaloyloxymethyl group, and form a bis(pivaloyloxymethyl) (bis(POM)) prodrug.

In some embodiments, both $R^{6A}$ and $R^{7A}$ can be

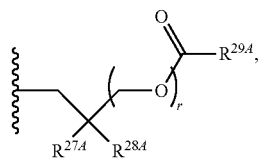

wherein $R^{27A}$ and $R^{28A}$ can be independently —C≡N or an optionally substituted substituent selected from $C_{2-8}$ organylcarbonyl, $C_{2-8}$ alkoxycarbonyl and $C_{2-8}$ organylaminocarbonyl; $R^{29A}$ can be selected from hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl; and r can be 1 or 2.

In some embodiments, $R^{6A}$ and $R^{7A}$ can be both an optionally substituted aryl. In some embodiments, at least one of $R^{6A}$ and $R^{7A}$ can be an optionally substituted aryl. For example, both $R^{6A}$ and $R^{7A}$ can be an optionally substituted phenyl or an optionally substituted naphthyl. When substituted, the substituted aryl can be substituted with 1, 2, 3 or more than 3 substituents. When more the two substituents are present, the substituents can be the same or different. In some embodiments, when at least one of $R^{6A}$ and $R^{7A}$ is a substituted phenyl, the substituted phenyl can be a para-, ortho- or meta-substituted phenyl.

In some embodiments, $R^{6A}$ and $R^{7A}$ can be both an optionally substituted aryl($C_{1-6}$ alkyl). In some embodiments, at least one of $R^{6A}$ and $R^{7A}$ can be an optionally substituted aryl($C_{1-6}$ alkyl). For example, both $R^{6A}$ and $R^{7A}$ can be an optionally substituted benzyl. When substituted, the substituted benzyl group can be substituted with 1, 2, 3 or more than 3 substituents. When more the two substituents are present, the substituents can be the same or different. In some embodiments, the aryl group of the aryl($C_{1-6}$ alkyl) can be a para-, ortho- or meta-substituted phenyl.

In some embodiments, $R^{6A}$ and $R^{7A}$ can be both

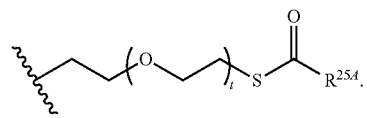

In some embodiments, at least one of $R^{6A}$ and $R^{7A}$ can be

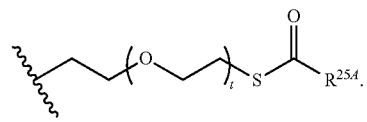

In some embodiments, $R^{25A}$ can be hydrogen. In other embodiments, $R^{25A}$ can be an optionally substituted $C_{1-24}$ alkyl. In still other embodiments, $R^{25A}$ can be an optionally substituted aryl, for example, an optionally substituted phenyl. In some embodiments, $R^{25A}$ can be a $C_{1-6}$ alkyl, for example, methyl, ethyl, n-propyl, isopropyl, n-butyl, isobutyl, tert-butyl, pentyl (branched and straight-chained) and hexyl (branched and straight-chained). In some embodiments, t can be 0. In other embodiments, t can be 1. In some embodiments, one or both of $R^{6A}$ and $R^{7A}$ can be a S-acyl-thioethyl (SATE).

In some embodiments, $R^{6A}$ and $R^{7A}$ can be both

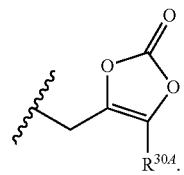

In some embodiments, at least one of $R^{6A}$ and $R^{7A}$ can be

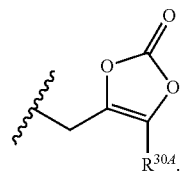

In some embodiments, $R^{30A}$ can be hydrogen. In other embodiments, $R^{30A}$ can be an optionally substituted $C_{1-24}$ alkyl. In some embodiments, $R^{30A}$ can be a $C_{1-4}$ alkyl, such as methyl, ethyl, n-propyl, iso-propyl, n-butyl, iso-butyl and t-butyl. In still other embodiments, $R^{30A}$ can be an optionally substituted aryl, such as an optionally substituted phenyl or an optionally substituted naphthyl. In some embodiments, $R^{6A}$ and $R^{7A}$ can be both a dioxolenone group and form a dioxolenone prodrug.

In some embodiments, $R^{1A}$ can be

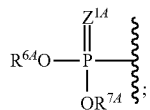

$R^{6A}$ can be

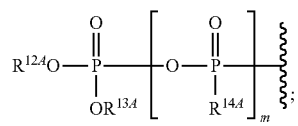

$R^{7A}$ can be absent or hydrogen; $R^{12A}$ and $R^{13A}$ can be independently absent or hydrogen; $R^{14A}$ can be O⁻, OH or methyl; and m can be 0 or 1. In some embodiments, m can be 0, and $R^{7A}$, $R^{12A}$ and $R^{13A}$ can be independently absent or hydrogen. In other embodiments, m can be 1, and $R^{7A}$, —$R^{12A}$ and $R^{13A}$ can be independently absent or hydrogen; and $R^{14A}$ can be O⁻ or OH. In other embodiments, m can be 1, and $R^{7A}$, $R^{12A}$ and $R^{13A}$ can be independently absent or hydrogen; and $R^{14A}$ and be methyl. Those skilled in the art understand that when $R^{6A}$ is

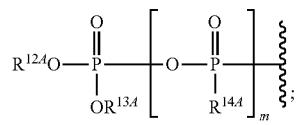

$R^{7A}$ is absent or hydrogen and m is 0, $R^{1A}$ can be diphosphate, when $Z^{1A}$ is oxygen, or an alpha-thiodiphosphate, when $Z^{1A}$ is sulfur. Likewise, those skilled in the art understand that when $R^{6A}$ is

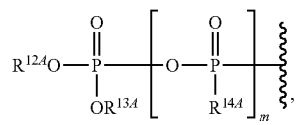

$R^{7A}$ is absent or hydrogen, m is 1 and $R^{14A}$ is O⁻ or OH, $R^{1A}$ can be triphosphate, when $Z^{1A}$ is oxygen, or an alpha-thiotriphosphate, when $Z^{1A}$ is sulfur.

In some embodiments, $R^{6A}$ and $R^{7A}$ can be taken together to form an optionally substituted

For example, $R^{1A}$ can be an optionally substituted

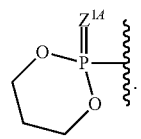

When substituted, the ring can be substituted 1, 2, 3 or 3 or more times. When substituted with multiple substituents, the substituents can be the same or different. In some embodiments, when $R^{1A}$ is

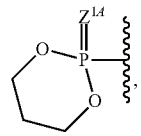

the ring can be substituted with an optionally substituted aryl group and/or an optionally substituted heteroaryl. An example of a suitable heteroaryl is pyridinyl. In some embodiments, $R^{6A}$ and $R^{7A}$ can be taken together to form an optionally substituted

such as

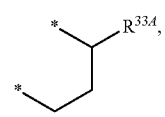

wherein $R^{33A}$ can be an optionally substituted aryl, an optionally substituted heteroaryl or an optionally substituted heterocyclyl. In some embodiments, $R^{6A}$ and $R^{7A}$ can form a cyclic 1-aryl-1,3-propanyl ester (HepDirect) prodrug moiety.

In some embodiments, $R^{6A}$ and $R^{7A}$ can be taken together to form an optionally substituted

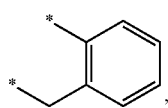 [SMILES: *Cc1ccccc1*]

wherein the oxygens connected to $R^{6A}$ and $R^{7A}$, the phosphorus and the moiety form a six-membered to ten-membered ring system. Example of an optionally substituted

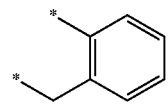

include

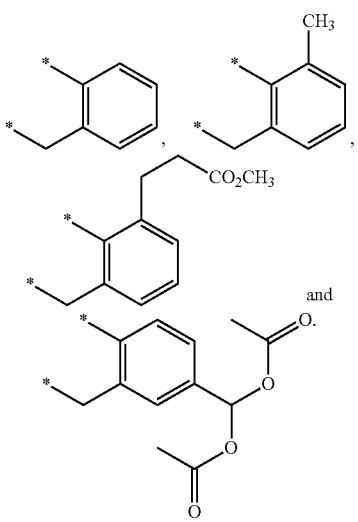

In some embodiments, $R^{6A}$ and $R^{7A}$ can form a cyclosaligenyl (cycloSal) prodrug.

In some embodiments, $R^{6A}$ and $R^{7A}$ can be the same. In some embodiments, $R^{6A}$ and $R^{7A}$ can be different.

In some embodiments, $Z^{1A}$ can be O (oxygen). In other embodiments, $Z^{1A}$ can be S (sulfur).

In some embodiments, $R^{1A}$ can be

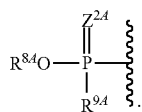

In some embodiments, $R^{8A}$ can be selected from absent, hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl; and $R^{9A}$ can be independently selected from an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl.

In some embodiments, $R^{8A}$ can be hydrogen, and $R^{9A}$ can be an optionally substituted $C_{1-6}$ alkyl. Examples of suitable $C_{1-6}$ alkyls include methyl, ethyl, n-propyl, isopropyl, n-butyl, isobutyl, tert-butyl, pentyl (branched and straight-chained) and hexyl (branched and straight-chained). In other embodiments, $R^{8A}$ can be hydrogen, and $R^{9A}$ can be $NR^{30A}R^{31A}$, wherein $R^{30}$ and $R^{31}$ can be independently selected from hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl.

In some embodiments, $R^{8A}$ can be absent or hydrogen; and $R^{9A}$ can be an optionally substituted N-linked amino acid or an optionally substituted N-linked amino acid ester derivative. In other embodiments, $R^{8A}$ can be an optionally substituted aryl; and $R^{9A}$ can be an optionally substituted N-linked amino acid or an optionally substituted N-linked amino acid ester derivative. In still other embodiments, $R^{8A}$ can be an optionally substituted heteroaryl; and $R^{9A}$ can be an optionally substituted N-linked amino acid or an optionally substituted N-linked amino acid ester derivative. In some embodiments, $R^{9A}$ can be selected from alanine, asparagine, aspartate, cysteine, glutamate, glutamine, glycine, proline, serine, tyrosine, arginine, histidine, isoleucine, leucine, lysine, methionine, phenylalanine, threonine, tryptophan, valine and ester derivatives thereof. Examples of an optionally substituted N-linked amino acid ester derivatives include optionally substituted versions of the following: alanine isopropyl ester, alanine cyclohexyl ester, alanine neopentyl ester, valine isopropyl ester and leucine isopropyl ester. In some embodiments, $R^{9A}$ can have the structure

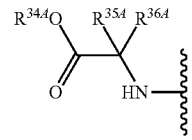

wherein $R^{34A}$ can be selected from hydrogen, an optionally substituted $C_{1-6}$-alkyl, an optionally substituted $C_{3-6}$ cycloalkyl, an optionally substituted aryl, an optionally substituted aryl($C_{1-6}$ alkyl) and an optionally substituted haloalkyl; $R^{35A}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{36A}$ can be hydrogen or an optionally substituted $C_{1-4}$ alkyl; or $R^{35A}$ and $R^{36A}$ can be taken together to form an optionally substituted $C_{3-6}$ cycloalkyl.

When $R^{35A}$ is substituted, $R^{35A}$ can be substituted with one or more substituents selected from N-amido, mercapto, alkylthio, an optionally substituted aryl, hydroxy, an optionally substituted heteroaryl, O-carboxy and amino. In some embodiments, $R^{35A}$ can be an unsubstituted $C_{1-6}$-alkyl, such as those described herein. In some embodiments, $R^{35A}$ can be hydrogen. In other embodiments, $R^{35A}$ can be methyl. In some embodiments, $R^{34A}$ can be an optionally substituted $C_{1-6}$ alkyl. Examples of optionally substituted $C_{1-6}$-alkyls include optionally substituted variants of the following: methyl, ethyl, n-propyl, isopropyl, n-butyl, isobutyl, tert-butyl, pentyl (branched and straight-chained) and hexyl (branched and straight-chained). In some embodiments, $R^{34A}$ can be methyl or isopropyl. In some embodiments, $R^{34A}$ can be ethyl or neopentyl. In other embodiments, $R^{34A}$ can be an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. In an embodiment, $R^{34A}$ can be an optionally substituted cyclohexyl. In still other embodiments, $R^{34A}$ can be an optionally substituted aryl, such as phenyl and naphthyl. In yet still other embodiments, $R^{34A}$ can be an optionally substituted aryl($C_{1-6}$ alkyl). In some embodiments, $R^{34A}$ can be an optionally substituted benzyl. In some embodiments, $R^{34A}$ can be an optionally substituted $C_{1-6}$ haloalkyl, for example, $CF_3$. In some embodiments, $R^{36A}$ can be hydrogen. In other embodiments, $R^{36A}$ can be an optionally substituted $C_{1-4}$ alkyl, such as methyl, ethyl, n-propyl, isopropyl, n-butyl, isobutyl and tert-butyl. In an embodiment, $R^{36A}$ can be methyl. In some embodiments, $R^{35A}$ and $R^{36A}$ can be taken together to form an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. Depending on the groups that are selected for $R^{35A}$ and $R^{36A}$, the carbon to which $R^{35A}$ and $R^{36A}$ are attached may be a chiral center. In some embodiment, the carbon to which $R^{35A}$ and $R^{36A}$ are attached may be a (R)-chiral center. In other embodiments, the carbon to which $R^{35A}$ and $R^{36A}$ are attached may be a (S)-chiral center.

In some embodiments, when $R^{1A}$ is

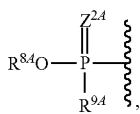

$Z^{2A}$ can be O (oxygen). In other embodiments, when $R^{1A}$ is

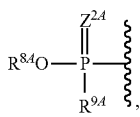

$Z^{2A}$ can be S (sulfur). In other embodiments, when $R^{1A}$ is

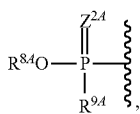

a compound of Formula (I) can be a phosphoramidate prodrug, such as an aryl phosphoramidate prodrug.

In some embodiments, $R^{1A}$ can be

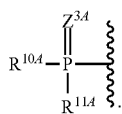

In some embodiments, $R^{10A}$ and $R^{11A}$ can be both an optionally substituted N-linked amino acid or an optionally substituted N-linked amino acid ester derivative. In some embodiments, $R^{10A}$ and $R^{11A}$ can be independently selected from alanine, asparagine, aspartate, cysteine, glutamate, glutamine, glycine, proline, serine, tyrosine, arginine, histidine, isoleucine, leucine, lysine, methionine, phenylalanine, threonine, tryptophan, valine and ester derivatives thereof.

In some embodiments, $R^{10A}$ and $R^{11A}$ can be an optionally substituted version of the following: alanine isopropyl ester, alanine cyclohexyl ester, alanine neopentyl ester, valine isopropyl ester and leucine isopropyl ester. In some embodiments, $R^{10A}$ and $R^{11A}$ can independently have the structure

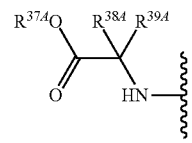

wherein $R^{37A}$ can be selected from hydrogen, an optionally substituted $C_{1-6}$-alkyl, an optionally substituted $C_{3-6}$ cycloalkyl, an optionally substituted aryl, an optionally substituted aryl($C_{1-6}$ alkyl) and an optionally substituted haloalkyl; $R^{38A}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{39A}$ can be hydrogen or an optionally substituted $C_{1-4}$ alkyl; or $R^{38A}$ and $R^{39A}$ can be taken together to form an optionally substituted $C_{3-6}$ cycloalkyl.

When $R^{38A}$ is substituted, $R^{38A}$ can be substituted with one or more substituents selected from N-amido, mercapto, alkylthio, an optionally substituted aryl, hydroxy, an optionally substituted heteroaryl, O-carboxy and amino. In some embodiments, $R^{38A}$ can be an unsubstituted $C_{1-6}$-alkyl, such as those described herein. In some embodiments, $R^{38A}$ can be hydrogen. In other embodiments, $R^{38A}$ can be methyl. In some embodiments, $R^{37A}$ can be an optionally substituted $C_{1-6}$ alkyl. Examples of optionally substituted $C_{1-6}$-alkyls include optionally substituted variants of the following: methyl, ethyl, n-propyl, isopropyl, n-butyl, isobutyl, tert-butyl, pentyl (branched and straight-chained) and hexyl (branched and straight-chained). In some embodiments, $R^{37A}$ can be methyl or isopropyl. In some embodiments, $R^{37A}$ can be ethyl or neopentyl. In other embodiments, $R^{37A}$ can be an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. In an embodiment, $R^{37A}$ can be an optionally substituted cyclohexyl. In still other embodiments, $R^{37A}$ can be an optionally substituted aryl, such as phenyl and naphthyl. In yet still other embodiments, $R^{37A}$ can be an optionally substituted aryl($C_{1-6}$ alkyl). In some embodiments, $R^{37A}$ can be an optionally substituted benzyl. In some embodiments, $R^{37A}$ can be an optionally substituted $C_{1-6}$ haloalkyl, for example, $CF_3$. In some embodiments, $R^{39A}$ can be hydrogen. In other embodiments, $R^{39A}$ can be an optionally substituted $C_{1-4}$ alkyl, such as methyl, ethyl, n-propyl, isopropyl, n-butyl, isobutyl and tert-butyl. In an embodiment, $R^{39A}$ can be methyl. In some embodiments, $R^{38A}$ and $R^{39A}$ can be taken together to form an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. Depending on the groups that are selected for $R^{38A}$ and $R^{39A}$, the carbon to which $R^{38A}$ and $R^{39A}$ are attached may be a chiral center. In some embodiment, the carbon to which $R^{38A}$ and $R^{39A}$ are attached may be a (R)-chiral center. In other embodiments, the carbon to which $R^{38A}$ and $R^{39A}$ are attached may be a (S)-chiral center.

Examples of suitable

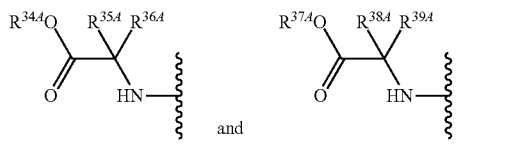

and groups include the following:

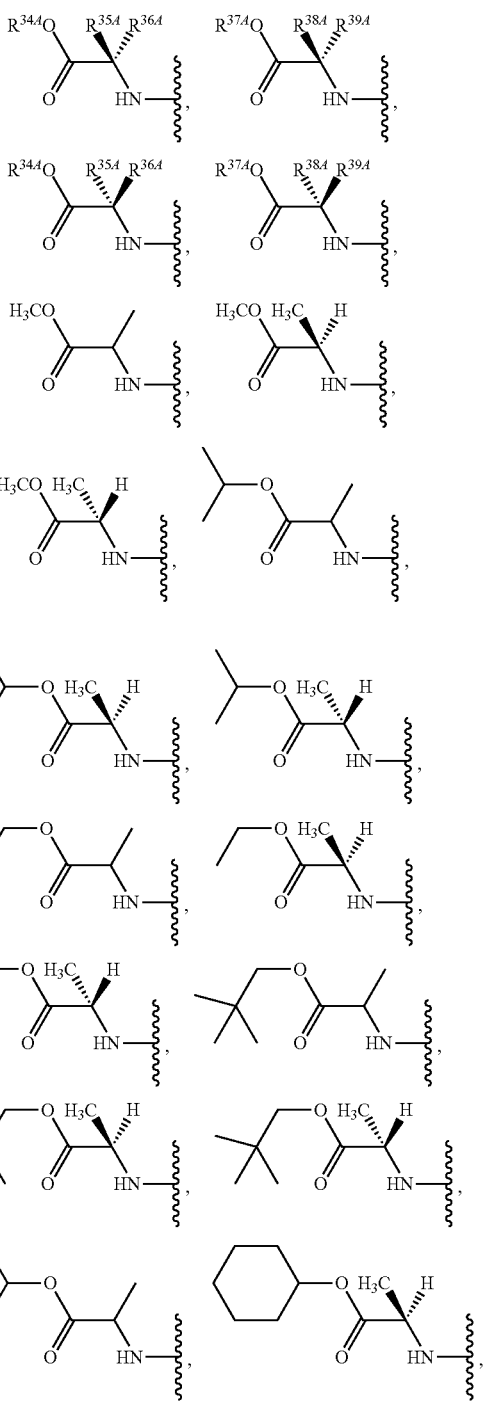

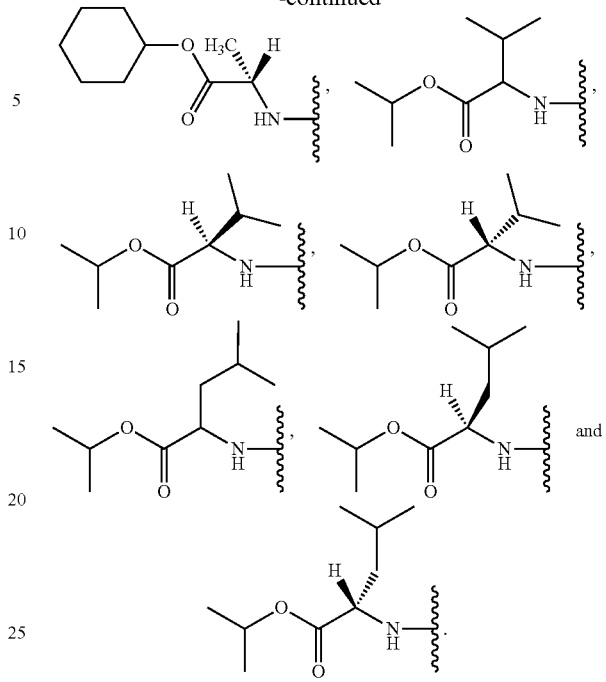

In some embodiments, $R^{10A}$ and $R^{11A}$ can be the same. In some embodiments, $R^{10A}$ and $R^{11A}$ can be different.

In some embodiments, $Z^{3A}$ can be O (oxygen). In other embodiments, $Z^{3A}$ can be S (sulfur). In some embodiments, when $R^{1A}$ is

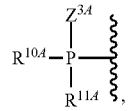

a compound of Formula (I) can be a phosphonic diamide prodrug.

In some embodiments, $R^{1A}$ can be hydrogen. In some embodiments, $R^{1A}$ can be an optionally substituted acyl. In other embodiments, $R^{1A}$ can be —C(=O)$R^{40A}$, wherein $R^{40A}$ can be selected from an optionally substituted $C_{1-12}$ alkyl, an optionally substituted $C_{2-12}$ alkenyl, an optionally substituted $C_{2-12}$ alkynyl, an optionally substituted $C_{3-8}$ cycloalkyl, an optionally substituted $C_{5-8}$ cycloalkenyl, an optionally substituted $C_{6-10}$ aryl, an optionally substituted heteroaryl, an optionally substituted heterocyclyl, an optionally substituted aryl($C_{1-6}$ alkyl), an optionally substituted heteroaryl($C_{1-6}$ alkyl) and an optionally substituted heterocyclyl($C_{1-6}$ alkyl). In some embodiments, $R^{40A}$ can be a substituted $C_{1-12}$ alkyl. In other embodiments, $R^{40A}$ can be an unsubstituted $C_{1-12}$ alkyl.

In still other embodiments, $R^{1A}$ can be an optionally substituted O-linked amino acid. Examples of suitable O-linked amino acids include alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine. In some embodiments, the O-linked amino acid can have the structure

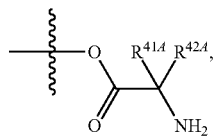

wherein $R^{41A}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{42A}$ can be hydrogen or an optionally substituted $C_{1-4}$ alkyl; or $R^{41A}$ and $R^{42A}$ can be taken together to form an optionally substituted $C_{3-6}$ cycloalkyl. Those skilled in the art understand that when $R^{1A}$ is an optionally substituted O-linked amino acid, the oxygen of $R^{1A}O$— of Formula (I) is part of the optionally substituted O-linked amino acid. For example, when $R^{1A}$ is

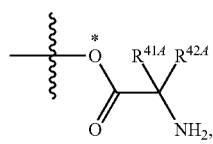

the oxygen indicated with "*" is the oxygen of $R^{1A}O$— of Formula (I).

When $R^{41A}$ is substituted, $R^{41A}$ can be substituted with one or more substituents selected from N-amido, mercapto, alkylthio, an optionally substituted aryl, hydroxy, an optionally substituted heteroaryl, O-carboxy and amino. In some embodiments, $R^{41A}$ can be an unsubstituted $C_{1-6}$-alkyl, such as those described herein. In some embodiments, $R^{41A}$ can be hydrogen. In other embodiments, $R^{41A}$ can be methyl. In some embodiments, $R^{42A}$ can be hydrogen. In other embodiments, $R^{42A}$ can be an optionally substituted $C_{1-4}$ alkyl, such as methyl, ethyl, n-propyl, isopropyl, n-butyl, isobutyl and tert-butyl. In an embodiment, $R^{42A}$ can be methyl. Depending on the groups that are selected for $R^{41A}$ and $R^{42A}$, the carbon to which $R^{41A}$ and $R^{42A}$ are attached may be a chiral center. In some embodiment, the carbon to which $R^{41A}$ and $R^{42A}$ are attached may be a (R)-chiral center. In other embodiments, the carbon to which $R^{41A}$ and $R^{42A}$ are attached may be a (S)-chiral center.

Examples of suitable

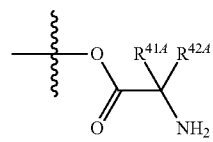

include the following:

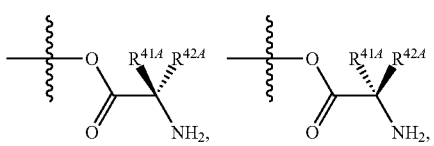

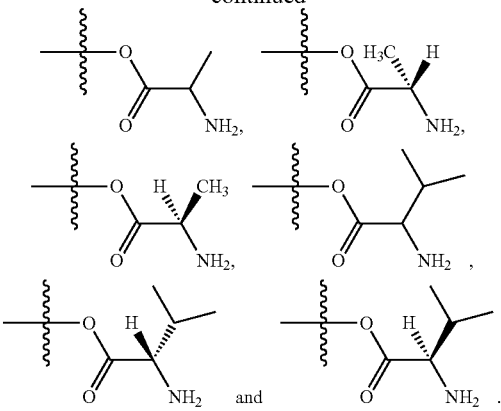

Various substituents can be present at the 4'-position of the pentose ring. In some embodiments, $R^{2A}$ can be an unsubstituted $C_{1-4}$ alkyl. Unsubstituted $C_{1-4}$ alkyls include methyl, ethyl, n-propyl, iso-propyl, n-butyl, iso-butyl and tert-butyl. In other embodiments, $R^{2A}$ can be an unsubstituted $C_{2-4}$ alkenyl, such as ethenyl, propenyl and butenyl. In still other embodiments, $R^{2A}$ can be an unsubstituted $C_{2-4}$ alkynyl, for example, ethynyl, propynyl and butynyl. In yet still other embodiments, $R^{2A}$ can be a haloalkyl. Examples of a haloalkyls are —$(CH_2)_{1-6}$ halogen and —$CHF_2$. In some embodiments, the haloalkyl can be —$(CH_2)_{1-6}F$ or —$(CH_2)_{1-6}Cl$. In yet still other embodiments, $R^{2A}$ can be a $C_{1-6}$ azidoalkyl. For example, $R^{2A}$ can be an azidomethyl, azidoethyl, azidopropyl, azidobutyl, azidopentyl or azidohexyl. In some embodiments, $R^{2A}$ can be a $C_{1-6}$ aminoalkyl. For example, $R^{2A}$ can be an aminomethyl, aminoethyl, aminopropyl, aminobutyl, aminopentyl or aminohexyl.

The groups attached to the 3'-position of the pentose ring can vary. In some embodiments, $R^{3A}$ can be hydrogen. In other embodiments, $R^{3A}$ can be deuterium. In still other embodiments, $R^{3A}$ can be halo. In yet still other embodiments, $R^{3A}$ can be OH.

In some embodiments, $R^{3A}$ can be an optionally substituted O-linked amino acid. Examples of suitable O-linked amino acids include alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine. In some embodiments, the O-linked amino acid can have the structure

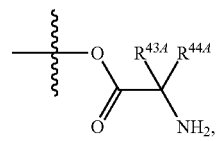

wherein $R^{43A}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{44A}$ can be hydrogen or an optionally substituted $C_{1-4}$ alkyl; or $R^{43A}$ and $R^{44A}$ can be taken together to form an optionally substituted $C_{3-6}$ cycloalkyl.

When $R^{43A}$ is substituted, $R^{43A}$ can be substituted with one or more substituents selected from N-amido, mercapto, alkylthio, an optionally substituted aryl, hydroxy, an optionally substituted heteroaryl, O-carboxy and amino. In some embodiments, $R^{43A}$ can be an unsubstituted $C_{1-6}$-alkyl, such as those described herein. In some embodiments, $R^{43A}$ can be hydrogen. In other embodiments, $R^{43A}$ can be methyl. In some embodiments, $R^{44A}$ can be hydrogen. In other embodiments, $R^{44A}$ can be an optionally substituted $C_{1-4}$ alkyl, such as methyl, ethyl, n-propyl, isopropyl, n-butyl, isobutyl and tert-butyl. In an embodiment, $R^{44A}$ can be methyl. Depending on the groups that are selected for $R^{43A}$ and $R^{44A}$, the carbon to which $R^{43A}$ and $R^{44A}$ are attached may be a chiral center. In some embodiment, the carbon to which $R^{43A}$ and $R^{44A}$ are attached may be a (R)-chiral center. In other embodiments, the carbon to which $R^{43A}$ and $R^{44A}$ are attached may be a (S)-chiral center.

In yet still other embodiments, $R^{3A}$ can be —OC(=O)$R'''^A$, wherein $R'''^A$ can be an optionally substituted $C_{1-24}$ alkyl. In some embodiments, $R'''^A$ can be a substituted $C_{1-8}$ alkyl. In other embodiments, $R'''^A$ can be an unsubstituted $C_{1-8}$ alkyl. In still other embodiments, $R^{3A}$ can be an optionally substituted —O-acyl. In some embodiments, $R^{3A}$ can be —OC(=O)$R^{45A}$, wherein $R^{45A}$ can be selected from an optionally substituted $C_{1-12}$ alkyl, an optionally substituted $C_{2-12}$ alkenyl, an optionally substituted $C_{2-12}$ alkynyl, an optionally substituted $C_{3-8}$ cycloalkyl, an optionally substituted $C_{5-8}$ cycloalkenyl, an optionally substituted $C_{6-10}$ aryl, an optionally substituted heteroaryl, an optionally substituted heterocyclyl, an optionally substituted aryl($C_{1-6}$ alkyl), an optionally substituted heteroaryl($C_{1-6}$ alkyl) and an optionally substituted heterocyclyl($C_{1-6}$ alkyl). In some embodiments, $R^{45A}$ can be a substituted $C_{1-12}$ alkyl. In other embodiments, $R^{45A}$ can be an unsubstituted $C_{1-12}$ alkyl. In some embodiment, the hydrogen shown in a compound of Formula (I), or a pharmaceutically acceptable salt thereof, attached to the 3'-position along with $R^{3A}$ can be an isotope of hydrogen, such as deuterium.

A variety of substituents can also be present at the 2'-position of the pentose ring. In some embodiments, $R^{4A}$ can be hydrogen. In other embodiments, $R^{4A}$ can be deuterium.

Examples of suitable

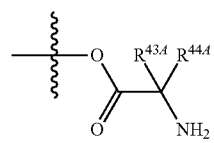

include the following:

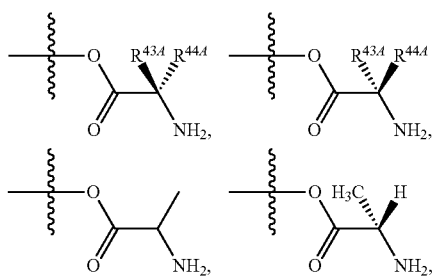

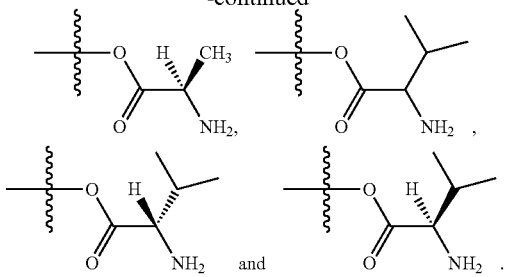

In some embodiments, $R^{5A}$ can be hydrogen. In other embodiments, $R^{5A}$ can be deuterium. In still other embodiments, $R^{5A}$ can be halogen, for example, fluoro or chloro. In yet still other embodiments, $R^{5A}$ can be $N_3$. In some embodiments, $R^{5A}$ can be OH. In other embodiments, $R^{5A}$ can be an optionally substituted $C_{1-6}$ alkyl. For example, in some embodiments, $R^{5A}$ can be a halo-substituted $C_{1-4}$ alkyl, such as a fluoro-substituted $C_{1-4}$ alkyl or a chloro-substituted $C_{1-4}$ alkyl. In still other embodiments, $R^{5A}$ can be an optionally substituted $C_{2-6}$ alkenyl. In yet still other embodiments, $R^{5A}$ can be an optionally substituted $C_{2-6}$ alkynyl. In some embodiments, $R^{5A}$ can be an unsubstituted $C_{1-6}$ alkyl, for example, for example, methyl, ethyl, n-propyl, isopropyl, n-butyl, isobutyl, tert-butyl, pentyl (branched and straight-chained) and hexyl (branched and straight-chained). In some embodiments, $R^{5A}$ can be an unsubstituted $C_{2-6}$ alkenyl. In still other embodiments, $R^{5A}$ can be an unsubstituted $C_{2-6}$ alkynyl.

In some embodiments, $R^{3A}$ can be OH and $R^{4A}$ can be hydrogen. In some embodiments, $R^{3A}$ can be OH, $R^{4A}$ can be hydrogen and $R^{5A}$ can be hydrogen. In some embodiments, $R^{3A}$ can be OH, $R^{4A}$ can be hydrogen and $R^{5A}$ can be an unsubstituted $C_{1-4}$ alkyl, for example, methyl, ethyl, n-propyl, iso-propyl, n-butyl, iso-butyl and tert-butyl. In some embodiments, $R^{3A}$ can be OH, $R^{4A}$ can be hydrogen and $R^{5A}$ can be a substituted $C_{1-4}$ alkyl, such as a halo-substituted $C_{1-4}$ alkyl. In some embodiments, $R^{3A}$ can be OH, $R^{4A}$ can be hydrogen and $R^{5A}$ can be an unsubstituted $C_{2-4}$ alkynyl, for example, ethynyl, propynyl, and butynyl. In some embodiments, $R^{3A}$ can be OH, $R^{4A}$ can be hydrogen and $R^{5A}$ can be chloro. In some embodiments, $R^{3A}$ can be OH, $R^{4A}$ can be hydrogen and $R^{5A}$ can be fluoro. In some embodiments, $R^{3A}$ can be OH, $R^{4A}$ can be hydrogen and $R^{5A}$ can be azido. In some embodiments, $R^{3A}$ can be OH, $R^{4A}$ can be hydrogen and $R^{5A}$ can be OH.

A variety of substituents can also be present at the 5'-position of the pentose ring. In some embodiments, both $R^{a1}$ and $R^{a2}$ can be hydrogen. In other embodiments, $R^{a1}$ can be hydrogen and $R^{a2}$ can be deuterium. In still other embodiments, both $R^{a1}$ and $R^{a2}$ can be deuterium. For the 1'-position, in some embodiments, $R^A$ can be hydrogen. In other embodiments, $R^A$ can be deuterium.

Various optionally substituted heterocyclic bases can be attached to the pentose ring. In some embodiments, one or more of the amine and/or amino groups may be protected with a suitable protecting group. For example, an amino group may be protected by transforming the amine and/or amino group to an amide or a carbamate. In some embodiments, an optionally substituted heterocyclic base or an optionally substituted heterocyclic base with one or more protected amino groups can have one of the following structures:

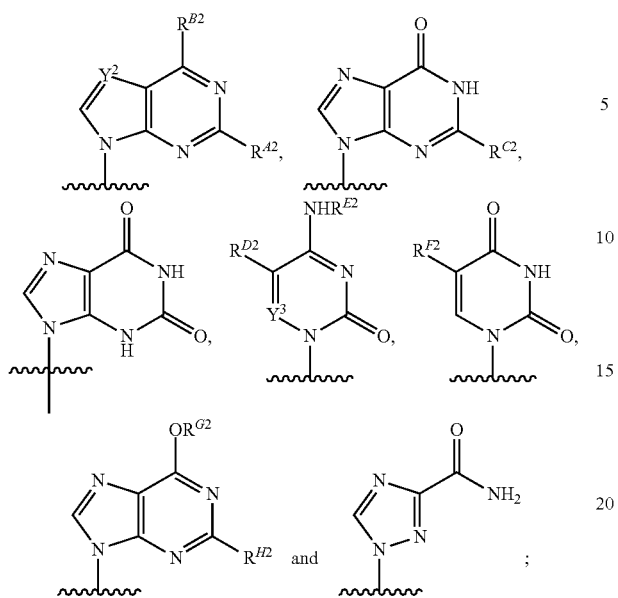

wherein: $R^{A2}$ can be selected from hydrogen, halogen and $NHR^{J2}$, wherein $R^{J2}$ can be selected from hydrogen, —C(=O)$R^{K2}$ and —C(=O)O$R^{L2}$; $R^{B2}$ be halogen or $NHR^{W2}$, wherein $R^{W2}$ can be selected from hydrogen, an optionally substituted $C_{1-6}$ alkyl, an optionally substituted $C_{2-6}$ alkenyl, an optionally substituted $C_{3-8}$ cycloalkyl, —C(=O)$R^{M2}$ and —C(=O)O$R^{N2}$; $R^{C2}$ can be hydrogen or $NHR^{O2}$, wherein $R^{O2}$ can be selected from hydrogen, —C(=O)$R^{P2}$ and —C(=O)O$R^{Q2}$; $R^{D2}$ can be selected from hydrogen, deuterium, halogen, an optionally substituted $C_{1-6}$ alkyl, an optionally substituted $C_{2-6}$ alkenyl and an optionally substituted $C_{2-6}$ alkynyl; $R^{E2}$ can be selected from hydrogen, hydroxy, an optionally substituted $C_{1-6}$ alkyl, an optionally substituted $C_{3-8}$ cycloalkyl, —C(=O)$R^{R2}$ and —C(=O)O$R^{S2}$; $R^{F2}$ can be selected from hydrogen, halogen, an optionally substituted $C_{1-6}$ alkyl, an optionally substituted $C_{2-6}$ alkenyl and an optionally substituted $C_{2-6}$ alkynyl; $Y^2$ and $Y^3$ can be independently N (nitrogen) or $CR^{I2}$, wherein $R^{I2}$ can be selected from hydrogen, halogen, an optionally substituted $C_{1-6}$-alkyl, an optionally substituted $C_{2-6}$-alkenyl and an optionally substituted $C_{2-6}$-alkynyl; $R^{G2}$ can be an optionally substituted $C_{1-6}$ alkyl; $R^{H2}$ can be hydrogen or $NHR^{T2}$, wherein $R^{T2}$ can be independently selected from hydrogen, —C(=O)$R^{U2}$ and —C(=O)O$R^{V2}$; and $R^{K2}$, $R^{L2}$, $R^{M2}$, $R^{N2}$, $R^{P2}$, $R^{Q2}$, $R^{R2}$, $R^{S2}$, $R^{U2}$ and $R^{V2}$ can be independently selected from $C_{1-6}$ alkyl, $C_{2-6}$ alkenyl, $C_{2-6}$ alkynyl, $C_{3-6}$ cycloalkyl, $C_{3-6}$ cycloalkenyl, $C_{6-10}$ aryl, heteroaryl, heterocyclyl, aryl($C_{1-6}$ alkyl), heteroaryl($C_{1-6}$ alkyl) and heterocyclyl($C_{1-6}$ alkyl). In some embodiments, the structures shown above can be modified by replacing one or more hydrogens with substituents selected from the list of substituents provided for the definition of "substituted."

In some embodiments, $B^{1A}$ can be

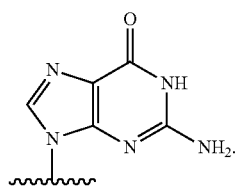 [SMILES: *n1cnc2c(=O)[nH]c(N)nc21]

In other embodiments, $B^{1A}$ can be

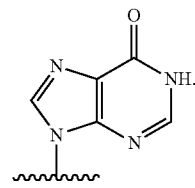 [SMILES: *n1cnc2c(=O)[nH]cnc21]

In still other embodiments, $B^{1A}$ can be

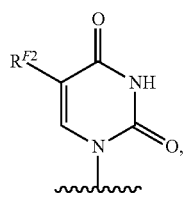

such as

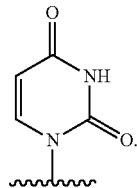 [SMILES: *n1ccc(=O)[nH]c1=O]

In yet still other embodiments, $B^{1A}$ can be

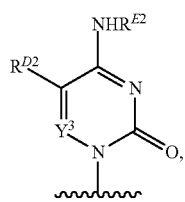

for example,

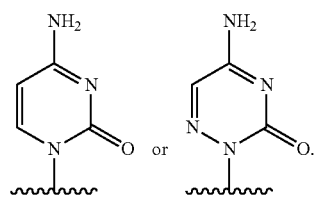 [SMILES: *n1ccc(N)nc1=O ; *n1ncc(N)nc1=O]

In some embodiments, $R^{D2}$ can be hydrogen. In other embodiments, $B^{1A}$ can be
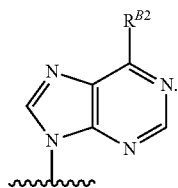
In some embodiments, $R^{B2}$ can be $NH_2$. In other embodiments, $R^{B2}$ can be $NHR^{W2}$, wherein $R^{W2}$ can be $-C(=O)R^{M2}$ or $-C(=O)OR^{N2}$. In still other embodiments, $B^{1A}$ can be
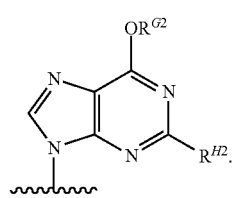
In some embodiments, $B^{1A}$ can be
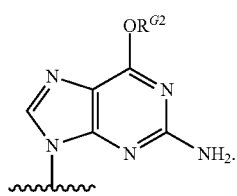
In some embodiments, a compound of Formula (I) can have the structure:
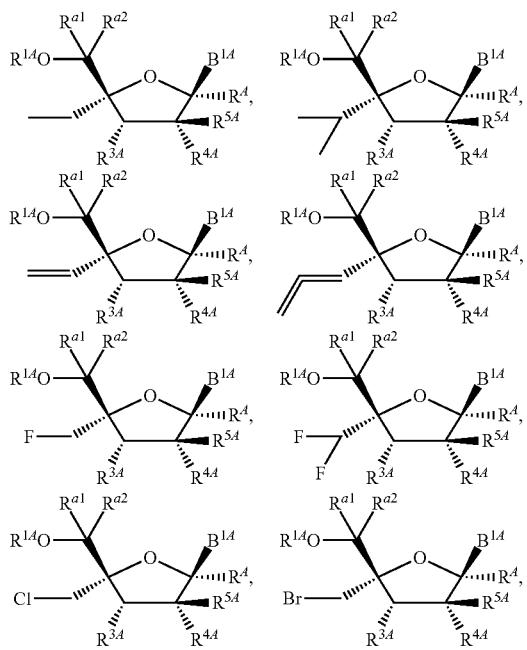
-continued
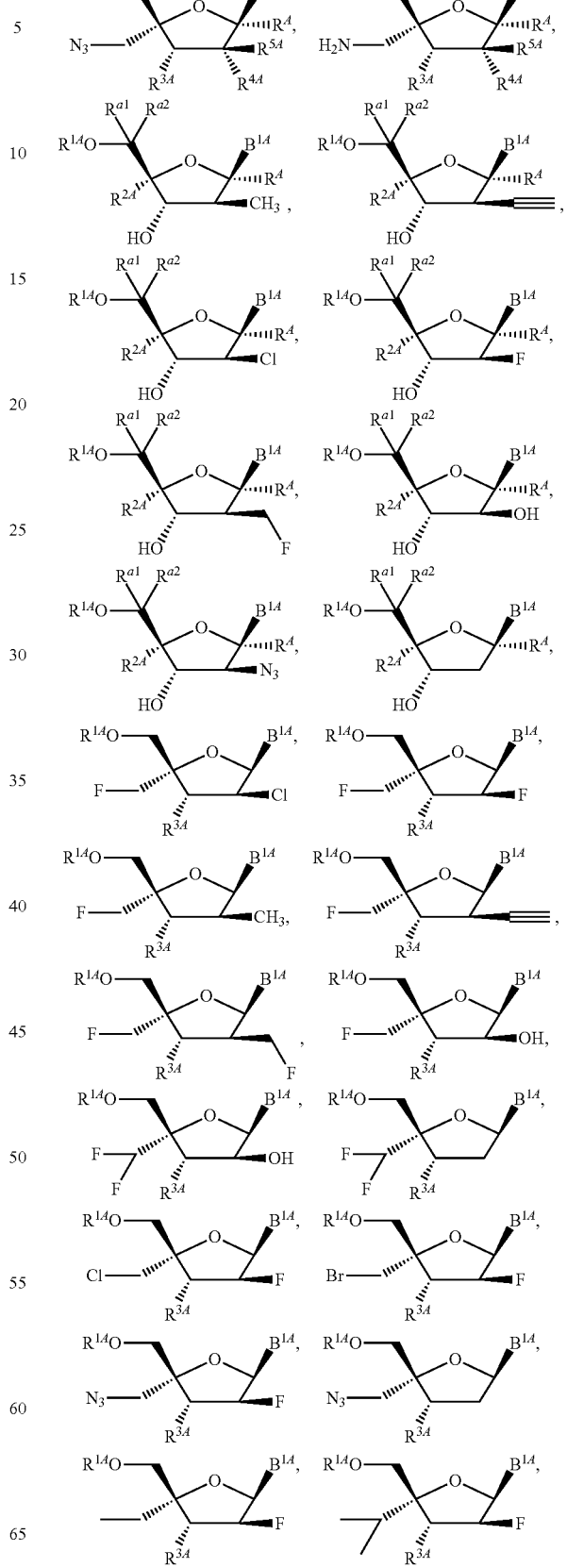

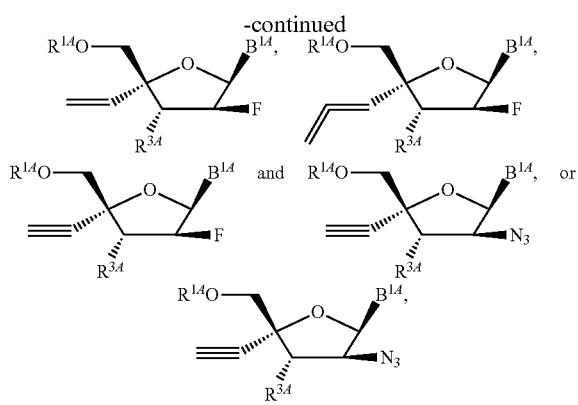

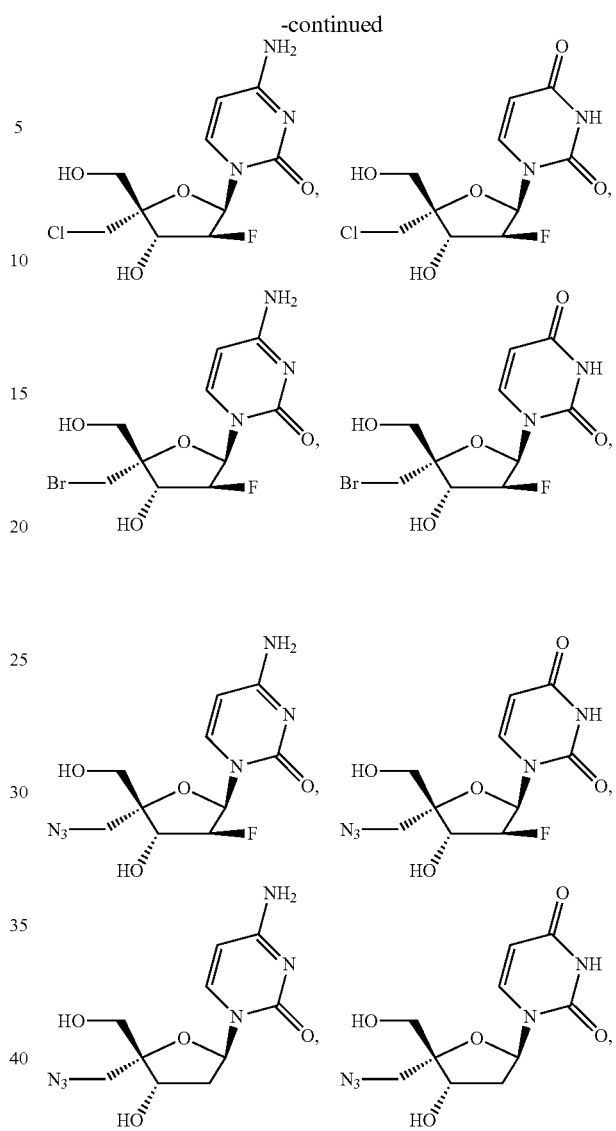

or a pharmaceutically acceptable salt of the foregoing. In some embodiments of this paragraph, $B^{1A}$ can be an optionally substituted purine base. In other embodiments of this paragraph, $B^{1A}$ can be an optionally substituted pyrimidine base. In some embodiments of this paragraph, $B^{1A}$ can be guanine. In other embodiments of this paragraph, $B^{1A}$ can be thymine. In still other embodiments of this paragraph, $B^{1A}$ can be cytosine. In yet still other embodiments of this paragraph, $B^{1A}$ can be uracil. In some embodiments of this paragraph, $B^{1A}$ can be adenine. In some embodiments of this paragraph, $R^{1A}$ can be hydrogen. In other embodiments of this paragraph, $R^{1A}$ can be an optionally substituted acyl. In still other embodiments of this paragraph, $R^{1A}$ can be mono-, di- or tri-phosphate. In yet other embodiments of this paragraph, $R^{1A}$ can be phosphoramidate prodrug, such as an aryl phosphoramidate prodrug. In some embodiments of this paragraph, $R^{1A}$ can be an acyloxyalkyl ester phosphate prodrug. In other embodiments of this paragraph, $R^{1A}$ can be a S-acylthioethyl (SATE) prodrug. In still other embodiments, $R^{1A}$ can be a phosphonic diamide prodrug. In yet still other embodiments, of this paragraph, $R^{1A}$ can be a cyclic 1-aryl-1,3-propanyl ester (HepDirect) prodrug moiety. In some embodiments of this paragraph, $R^{1A}$ can be a cyclosaligenyl (cycloSal) prodrug. In some embodiments of this paragraph, $R^{3A}$ can be OH. In some embodiments of this paragraph, $R^{3A}$ can be an optionally substituted O-linked amino acid, such as one of those described herein.

Examples of suitable compounds of Formula (I) include, but are not limited to the following:

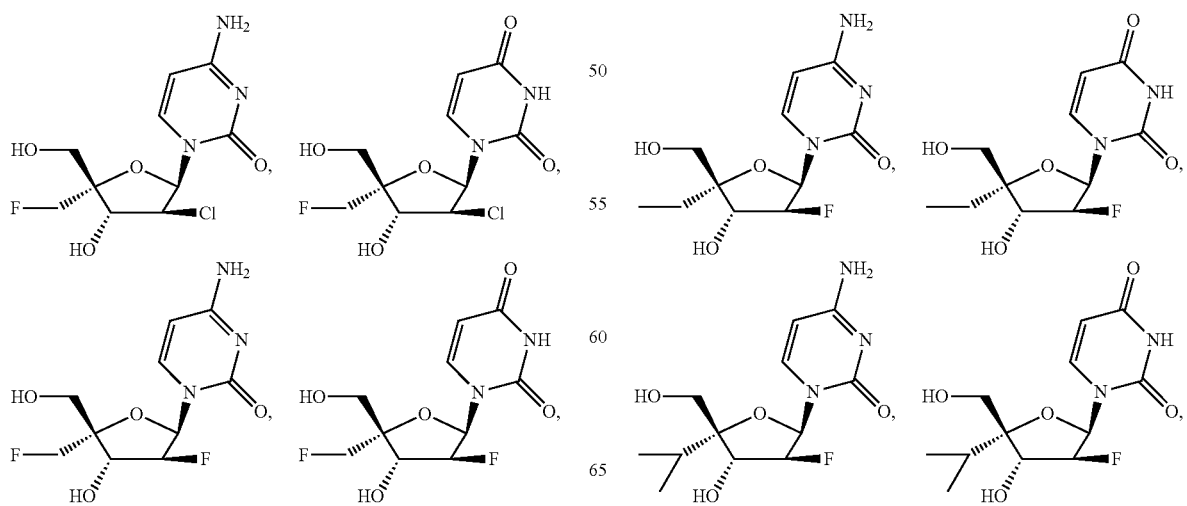

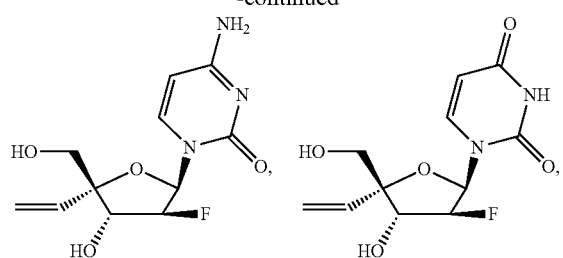
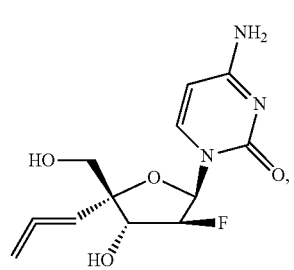
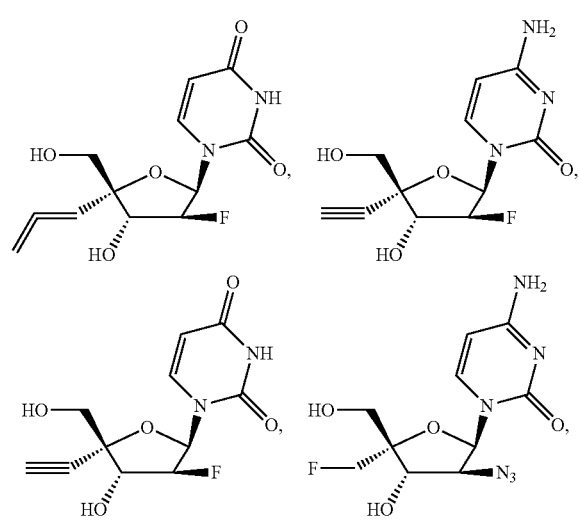
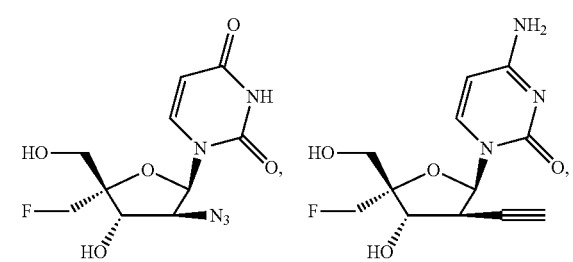
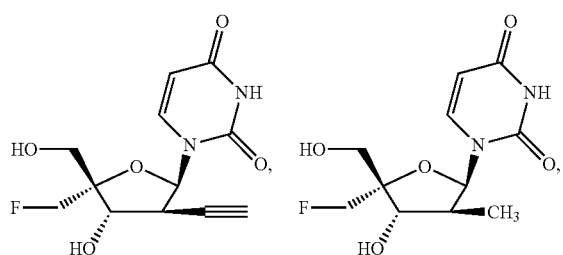
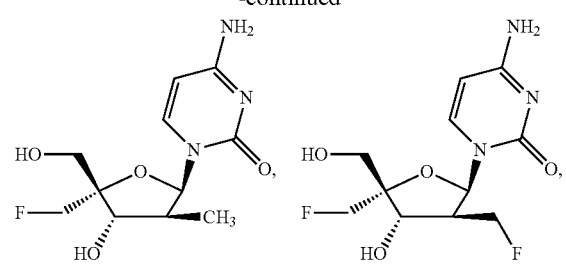
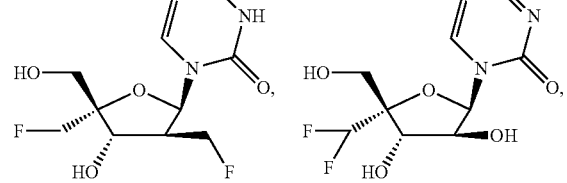
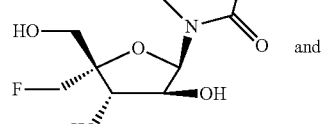
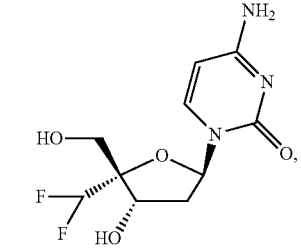
or a pharmaceutically acceptable salt of the foregoing.
Additional examples of suitable compounds of Formula (I) include, but are not limited to the following:
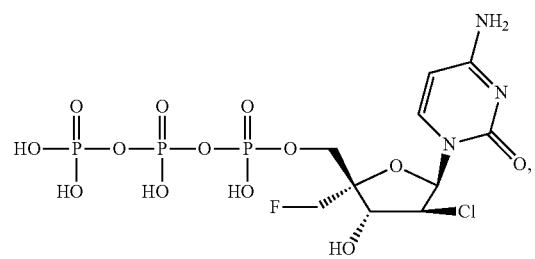
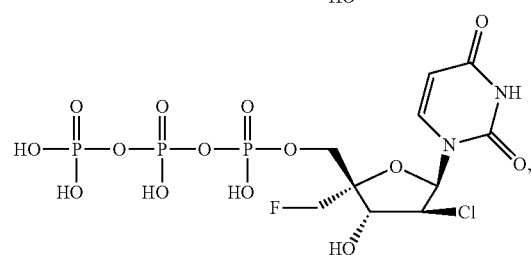

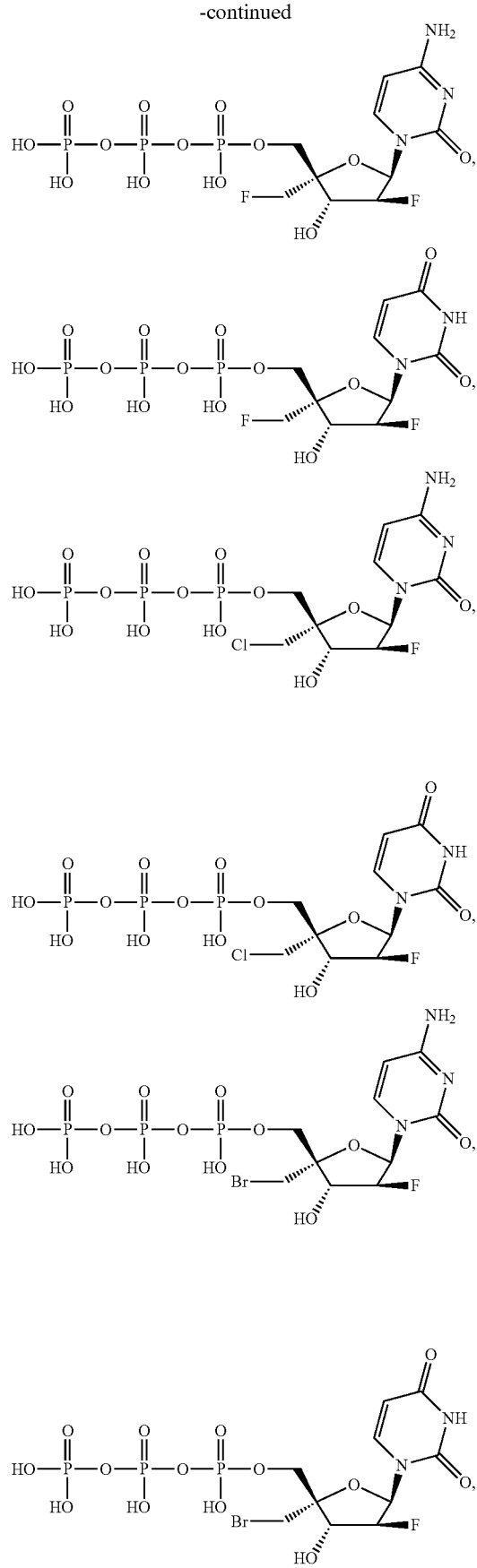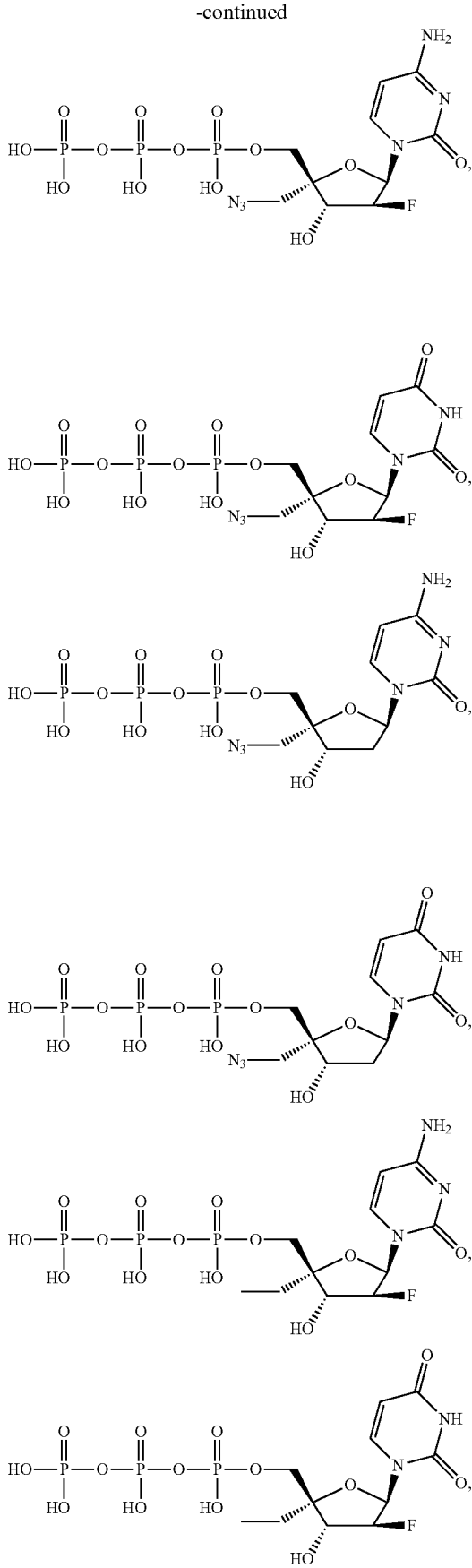

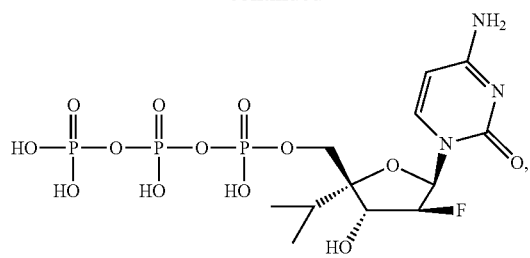
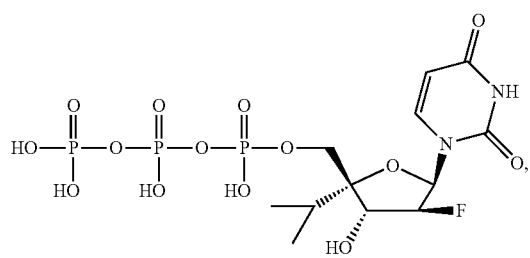
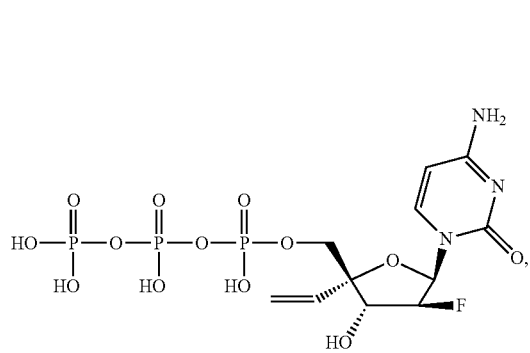
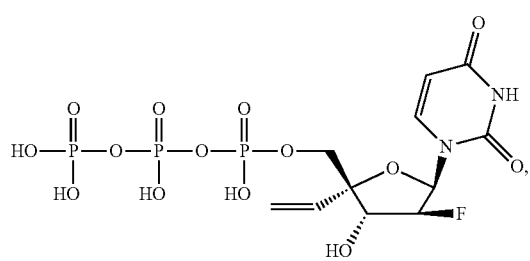
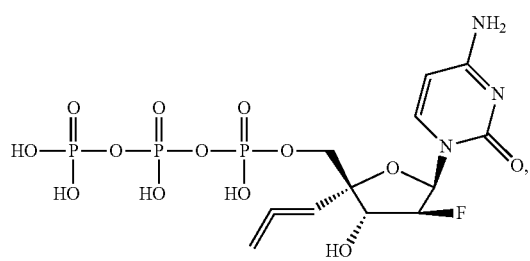
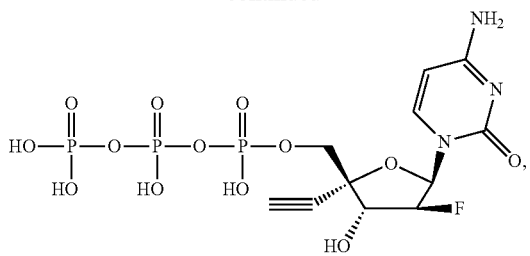
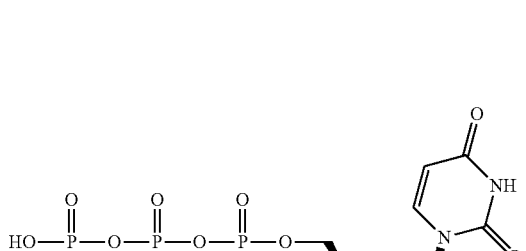
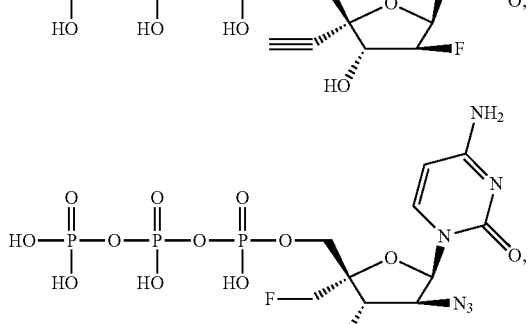
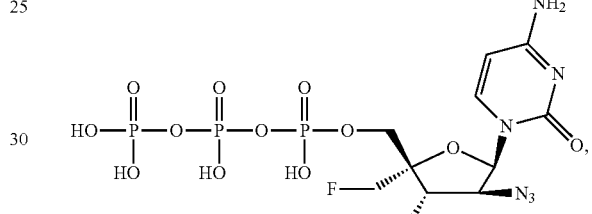

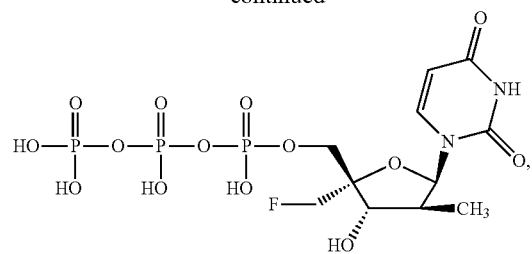

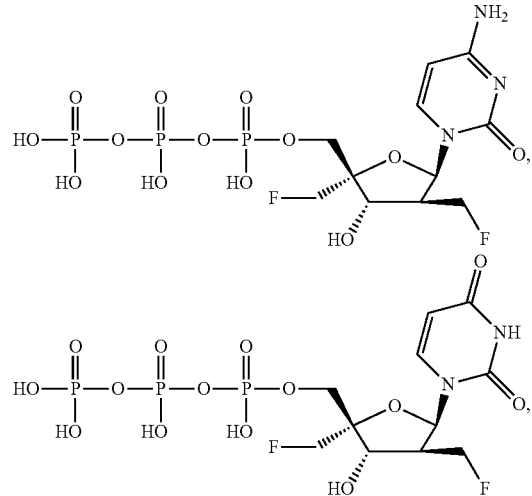

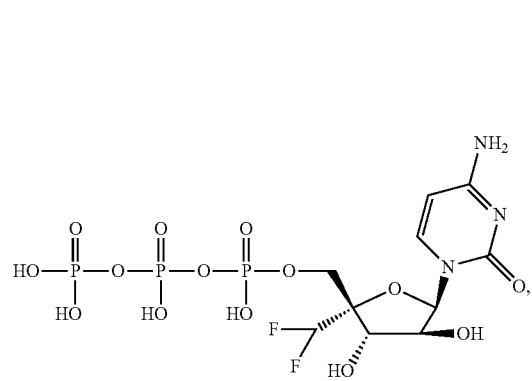

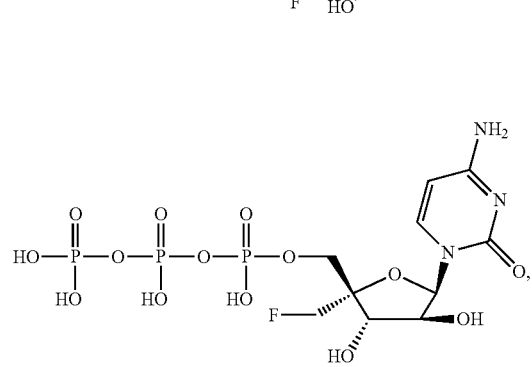

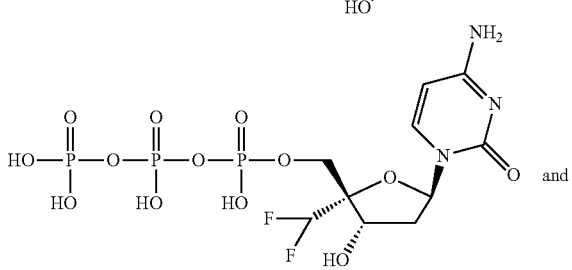

and

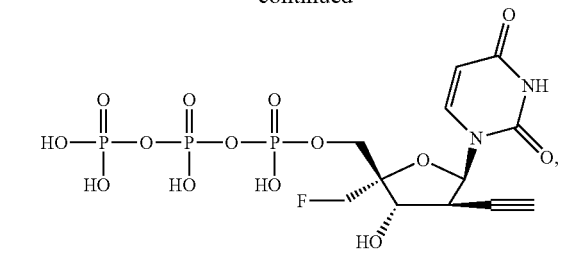

or a pharmaceutically acceptable salt of the foregoing.

Synthesis

Compounds of Formula (I) and those described herein may be prepared in various ways. Some compounds of Formula (I) can be obtained commercially and/or prepared utilizing known synthetic procedures. General synthetic routes to the compounds of Formula (I), and some examples of starting materials used to synthesize the compounds of Formula (I) are shown and described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

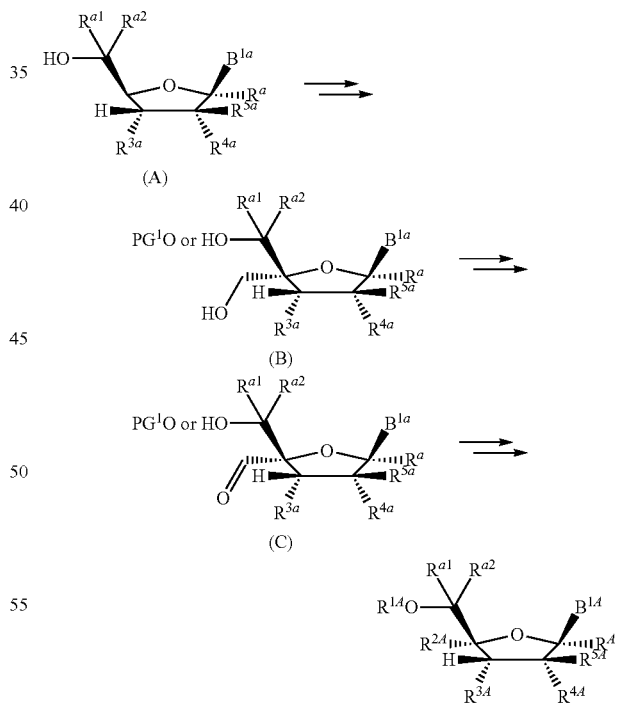

As shown in Scheme 1, compounds of Formula (I), wherein the 4'-position is a haloalkyl, can be prepared from a nucleoside, for example, a nucleoside of Formula (A). In Scheme 1, $R^a$, $R^{3a}$, $R^{4a}$, $R^{5a}$, and $B^{1a}$ can be the same as $R^A$, $R^{3A}$, $R^{4A}$, $R^{5A}$, and $B^{1A}$ as described herein for Formula (I), respectively, and $PG^1$ is a suitable protecting group. A hydroxyalkyl group can be formed at the 4'-position of the pentose ring using suitable conditions known to those skilled in the art. Examples of suitable conditions for forming a hydroxyalkyl include the use of 2-iodoxybenzoic acid (IBX) aqueous formaldehyde and sodium borohydride. A compound of Formula (B) can be transformed to a haloalkyl using a suitable agent(s), for example, to an iodide using imidazole, triphenylphosphine and iodine; to a fluoro using diethylaminosulfur trifluoride (DAST); or to a chloro using triphenylphosphine and carbontetrachloride in dichloroethylene (DCE).

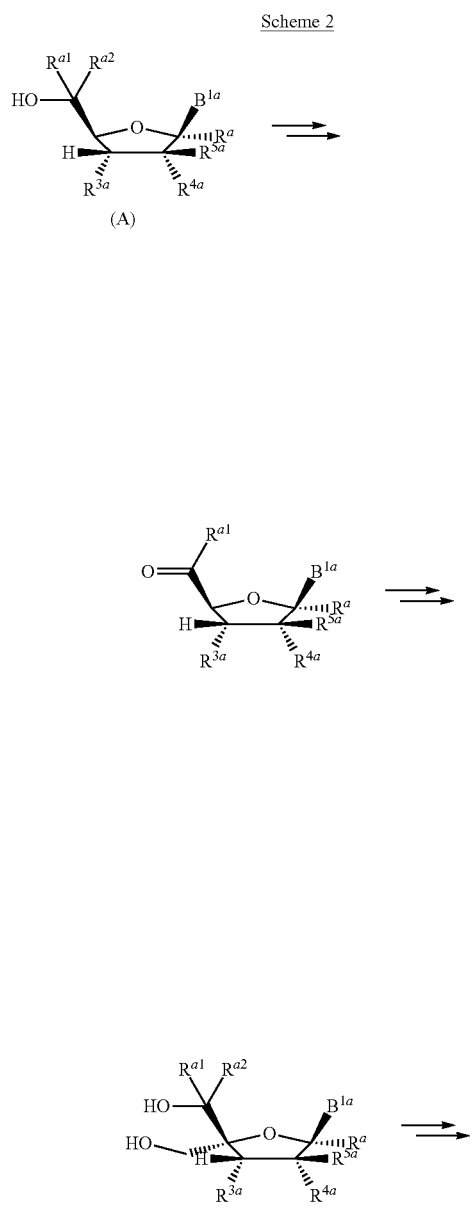

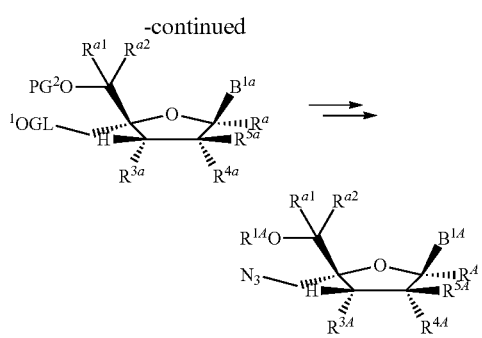

Compounds of Formula (I), where $R^{2A}$ is a $C_{1-6}$ azidoalkyl can be prepared from a nucleoside, for example, a nucleoside of Formula (A). In Scheme 2, $R^a$, $R^{3a}$, $R^{4a}$, $R^{5a}$ and $B^{1a}$ can be the same as $R^A$, $R^{3A}$, $R^{4A}$, $R^{5A}$ and $B^{1A}$ as described herein for Formula (I), $PG^2$ can be a suitable protecting group and $LG^1$ can be a suitable leaving group. The 5'-position of the nucleoside can be oxidized to an aldehyde using methods known to those skilled in the art. Suitable oxidation conditions include, but are not limited to, Moffatt oxidation, Swern oxidation and Corey-Kim oxidation; and suitable oxidizing agents include, but are not limited to, Dess-Martin periodinane, IBX (2-iodoxybenzoic acid), TPAP/NMO (tetrapropylammonium perruthenate/N-methylmorpholine N-oxide), Swern oxidation reagent, PCC (pyridinium chlorochromate), PDC (pyridinium dichromate), sodium periodate, Collin's reagent, ceric ammonium nitrate CAN, $Na_2Cr_2O_7$ in water, $Ag_2CO_3$ on celite, hot $HNO_3$ in aqueous glyme, $O_2$-pyridine CuCl, $Pb(OAc)_4$-pyridine and benzoyl peroxide-$NiBr_2$. A hydroxymethyl group can be added to the 4'-position of the pentose ring along with the reduction of the aldehyde to an alcohol. The hydroxymethyl group can be added via a condensation reaction using formaldehyde and a base, such as sodium hydroxide. After addition of the hydroxymethyl group, reduction of the intermediate compound with a 4'-hydroxymethyl group can be conducted using a reducing reagent. Examples of suitable reducing agents include, but are not limited to, $NaBH_4$ and $LiAlH_4$. A suitable leaving group, such as a triflate, can be formed by replacing the hydrogen of the hydroxymethyl group attached to the 4'-position, and the oxygen attached to the 5'-position can be protected with a suitable protecting group (for example, by cyclization with the base, $B^{1a}$, or with a separate protecting group). The leaving group can be replaced with an azido group using a metal azide reagent, for example, sodium azide.

A $C_{1-6}$ azidoalkyl at the 4'-position can be reduced to a $C_{1-6}$ aminoalkyl. Various reduction agents/conditions known to those skilled in the art can be utilized. For example, the azido group can be reduced to an amino group via hydrogenation (for example, $H_2$—Pd/C or $HCO_2NH_4$—Pd/C), Staudinger Reaction, $NaBH_4/CoCl_2.6\ H_2O$, Fe/$NH_4Cl$ or Zn/$NH_4Cl$.

Scheme 3
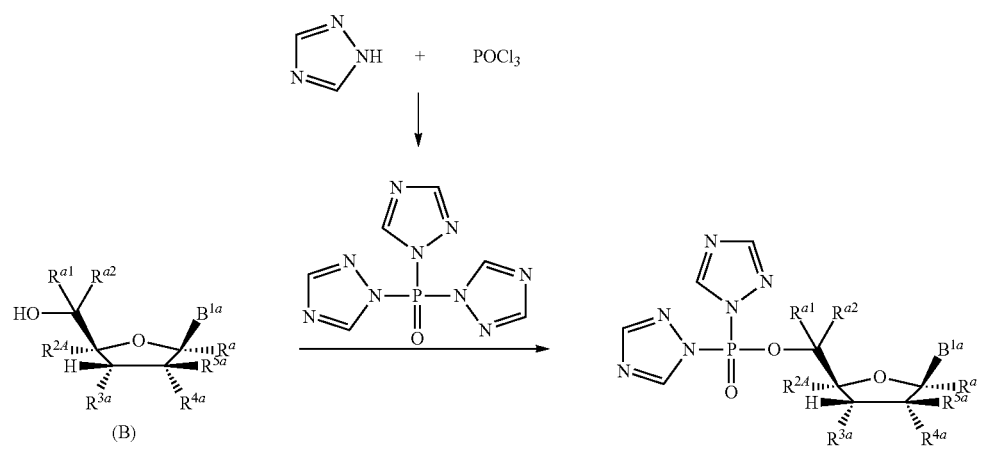
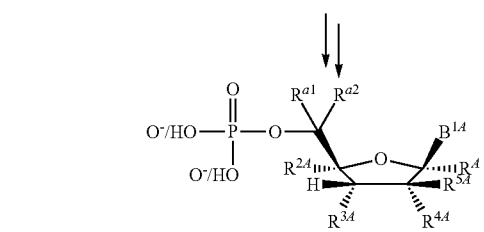
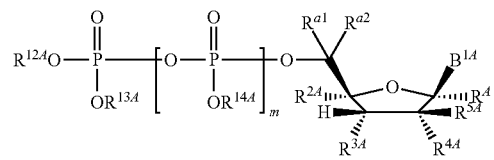
Scheme 4
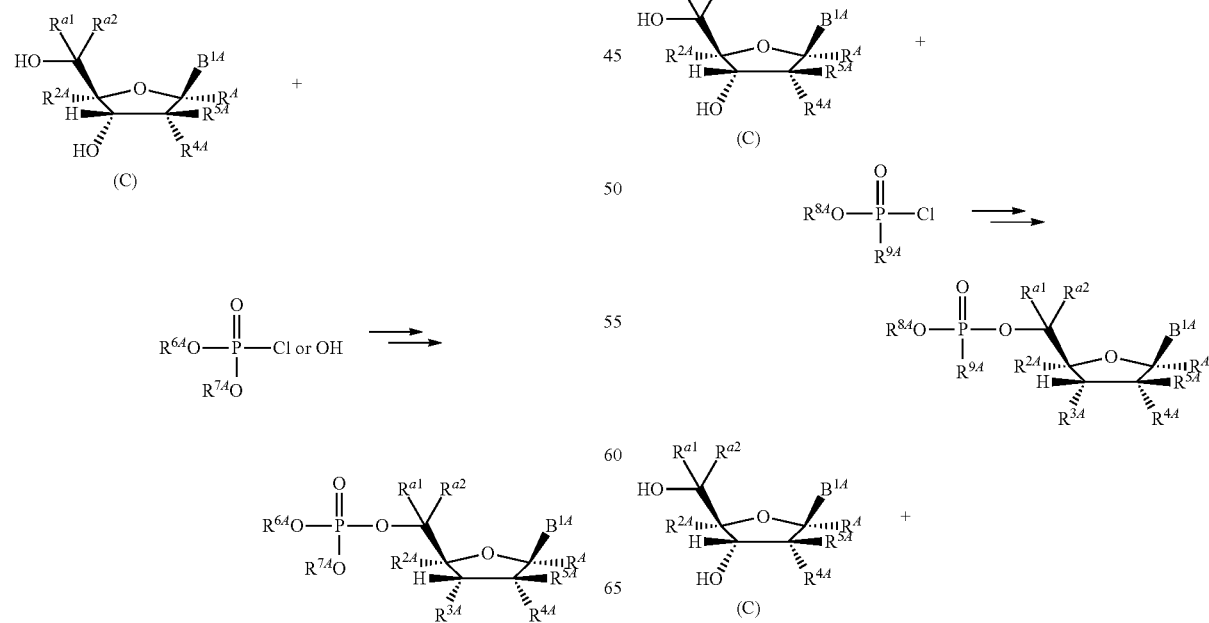

-continued

POCl₃
amino acid or amino acid ester ⟶

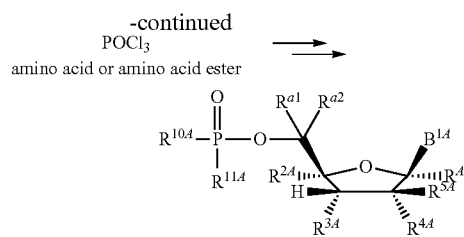

Compounds of Formula (I) having a phosphorus containing group attached to the 5'-position of the pentose ring can be prepared using various methods known to those skilled in the art. Examples of methods are shown in Schemes 3 and 4. In Schemes 3 and 4, $R^a$, $R^{2a}$, $R^{3a}$, $R^{4a}$, $R^{5a}$ and $B^{1a}$ can be the same as $R^A$, $R^{2A}$, $R^{3A}$, $R^{4A}$, $R^{5A}$ and $B^{1A}$ as described herein for Formula (I). A phosphorus containing precursor can be coupled to the nucleoside, for example, a compound of Formula (B). As shown in Scheme 3, following the coupling of the phosphorus containing precursor, any leaving groups can be cleaved under suitable conditions, such as hydrolysis. Further phosphorus containing groups can be added using methods known to those skilled in the art, for example using a pyrophosphate.

In some embodiments, an alkoxide can be generated from a compound of Formula (C) using an organometallic reagent, such as a Grignard reagent. The alkoxide can be coupled to the phosphorus containing precursor. Suitable Grignard reagents are known to those skilled in the art and include, but are not limited to, alkylmagnesium chlorides and alkylmagnesium bromides. In some embodiments, an appropriate base can be used. Examples of suitable bases include, but are not limited to, an amine base, such as an alkylamine (including mono-, di- and tri-alkylamines (e.g., triethylamine)), optionally substituted pyridines (e.g. collidine) and optionally substituted imidazoles (e.g., N-methylimidazole)). Alternatively, a phosphorus containing precursor can be added to the nucleoside and form a phosphite. The phosphite can be oxidized to a phosphate using conditions known to those skilled in the art. Suitable conditions include, but are not limited to, meta-chloroperoxybenzoic acid (MCPBA) and iodine as the oxidizing agent and water as the oxygen donor.

When compounds of Formula (I) have $Z^{1A}$, $Z^{2A}$ or $Z^{3A}$ being sulfur, the sulfur can be added in various manners known to those skilled in the art. In some embodiments, the sulfur can be part of the phosphorus containing precursor, for example,

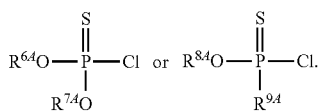

Alternatively, the sulfur can be added using a sulfurization reagent. Suitable sulfurization agents are known to those skilled in the art, and include, but are not limited to, elemental sulfur, Lawesson's reagent, cyclooctasulfur, 3H-1,2-Benzodithiole-3-one-1,1-dioxide (Beaucage's reagent), 3-((N,N-dimethylaminomethylidene)amino)-3H-1,2,4-dithiazole-5-thione (DDTT) and bis(3-triethoxysilyl)propyl-tetrasulfide (TEST).

Suitable phosphorus containing precursors can be commercially obtained or prepared by synthetic methods known to those skilled in the art. Examples of general structures of phosphorus containing precursors are shown in Schemes 3 and 4.

During the synthesis of any of the compounds described herein, if desired, any hydroxy groups attached to the pentose ring, and any —NH and/or NH₂ groups present on the $B^{1a}$, can be protected with one or more suitable protecting groups. Suitable protecting groups are described herein. For example, when $R^{3a}$ is a hydroxy group, $R^{3a}$ can be protected with a triarylmethyl group or a silyl group. Likewise, any —NH and/or NH₂ groups present on the $B^{1a}$ can be protected, such as with a triarylmethyl and a silyl group(s). Examples of triarylmethyl groups include but are not limited to, trityl, monomethoxytrityl (MMTr), 4,4'-dimethoxytrityl (DMTr), 4,4',4"-trimethoxytrityl (TMTr), 4,4',4"-tris-(benzoyloxy) trityl (TBTr), 4,4',4"-tris (4,5-dichlorophthalimido) trityl (CPTr), 4,4',4"-tris (levulinyloxy) trityl (TLTr), p-anisyl-1-naphthylphenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl) xanthen-9-yl (Mox), 4-decyloxytrityl, 4-hexadecyloxytrityl, 4,4'-dioctadecyltrityl, 9-(4-octadecyloxyphenyl) xanthen-9-yl, 1,1'-bis-(4-methoxyphenyl)-1'-pyrenylmethyl, 4,4',4"-tris-(tert-butylphenyl) methyl (TTTr) and 4,4'-di-3, 5-hexadienoxytrityl. Examples of silyl groups include, but are not limited to, trimethylsilyl (TMS), tert-butyldimethylsilyl (TBDMS), triisopropylsilyl (TIPS), tert-butyldiphenylsilyl (TBDPS), tri-iso-propylsilyloxymethyl and [2-(trimethylsilyl)ethoxy]methyl. Those skilled in the art will appreciate that groups attached to the pentose ring and any —NH and/or NH₂ groups present on the $B^{1a}$ can be protected with various protecting groups, and any protecting groups present can be exchanged for other protecting groups. The selection and exchange of the protecting groups is within the skill of those of ordinary skill in the art. Any protecting group(s) can be removed by methods known in the art, for example, with an acid (e.g., a mineral or an organic acid), a base or a fluoride source.

Pharmaceutical Compositions

Some embodiments described herein relates to a pharmaceutical composition, that can include an effective amount of one or more compounds described herein (e.g., a compound of Formula (I), or a pharmaceutically acceptable salt thereof) and a pharmaceutically acceptable carrier, diluent, excipient or combination thereof.

The term "pharmaceutical composition" refers to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, and salicylic acid. Pharmaceutical compositions will generally be tailored to the specific intended route of administration.

The term "physiologically acceptable" defines a carrier, diluent or excipient that does not abrogate the biological activity and properties of the compound.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes will be targeted to and taken up selectively by the organ.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

Methods of Use:

Some embodiments disclosed herein relate to a method of treating and/or ameliorating a Picornavirus infection that can include administering to a subject infected with the Picornavirus an effective amount of one or more compounds described herein (such as a compound of Formula (I), or a pharmaceutically acceptable salt thereof), or a pharmaceutical composition that includes a compound described herein (such as a compound of Formula (I), or a pharmaceutically acceptable salt thereof). Other embodiments disclosed herein relate to a method of treating and/or ameliorating a Picornavirus infection that can include administering to a subject identified as suffering from the viral infection an effective amount of one or more compounds described herein (such as a compound of Formula (I), or a pharmaceutically acceptable salt thereof), or a pharmaceutical composition that includes a compound described herein (such as a compound of Formula (I), or a pharmaceutically acceptable salt thereof).

Some embodiments described herein relate to using one or more compounds described herein (such as a compound of Formula (I), or a pharmaceutically acceptable salt thereof), in the manufacture of a medicament for ameliorating and/or treating a Picornavirus infection that can include administering to a subject infected with the Picornavirus an effective amount of one or more compounds described herein (such as a compound of Formula (I), or a pharmaceutically acceptable salt thereof). Still other embodiments described herein relate to one or more compounds described herein (such as a compound of Formula (I), or a pharmaceutically acceptable salt thereof) that can be used for ameliorating and/or treating a Picornavirus infection by administering to a subject infected with the Picornavirus an effective amount of one or more compounds described herein.

Some embodiments disclosed herein relate to methods of ameliorating and/or treating a Picornavirus infection that can include contacting a cell infected with the virus with an effective amount of one or more compounds described herein (such as a compound of Formula (I), or a pharmaceutically acceptable salt thereof), or a pharmaceutical composition that includes one or more compounds described herein (such as a compound of Formula (I), or a pharmaceutically acceptable salt thereof). Other embodiments described herein relate to using one or more compounds described herein (such as a compound of Formula (I), or a pharmaceutically acceptable salt thereof), in the manufacture of a medicament for ameliorating and/or treating a Picornavirus infection that can include contacting a cell infected with the virus with an effective amount of said compound(s). Still other embodiments described herein relate to one or more compounds described herein (such as a compound of Formula (I), or a pharmaceutically acceptable salt thereof), that can be used for ameliorating and/or treating a Picornavirus infection by contacting a cell infected with the virus with an effective amount of said compound(s).

Some embodiments disclosed herein relate to methods of inhibiting replication of a Picornavirus that can include contacting a cell infected with the virus with an effective amount of one or more compounds described herein (such as a compound of Formula (I), or a pharmaceutically acceptable salt thereof), or a pharmaceutical composition that includes one or more compounds described herein (such as a compound of Formula (I), or a pharmaceutically acceptable salt thereof). Other embodiments described herein relate to using one or more compounds described herein (such as a compound of Formula (I), or a pharmaceutically acceptable salt thereof), in the manufacture of a medicament for inhibiting replication of a Picornavirus that can include contacting a cell infected with the virus with an effective amount of said compound(s). Still other embodiments described herein relate to a compound described herein (such as a compound of Formula (I), or a pharmaceutically acceptable salt thereof), that can be used for inhibiting replication of a Picornavirus by contacting a cell infected with the virus with an effective amount of said compound(s). In some embodiments, a compound of Formula (I), or a pharmaceutically acceptable salt thereof, can inhibit a RNA dependent RNA polymerase of a picornavirus, and thus, inhibit the replication of RNA. In some embodiments, a polymerase of a picornavirus can be inhibited by contacting a cell infected with the picornavirus with a compound described herein (such as a compound of Formula (I), or a pharmaceutically acceptable salt thereof).

In some embodiments, the picornavirus can be selected from an Aphthovirus, an Enterovirus, a Rhinovirus, a Hepatovirus and a Parechovirus. Within the Enterovirus genus, there are several species of Enteroviruses including enterovirus A, enterovirus B, enterovirus C, enterovirus D, enterovirus E, enterovirus F, enterovirus G, enterovirus Henterovirus J. Each Enterovirus species includes several serotypes. Examples of Enterovirus serotypes include the following: poliovirus 1, poliovirus 2, poliovirus 3, echovirus 1, echovirus 2, echovirus 3, echovirus 4, echovirus 5, echovirus 6, echovirus 7, echovirus 9, echovirus 11, echovirus 12, echovirus 13, echovirus 14, echovirus 15, echovirus 16, echovirus 17, echovirus 18, echovirus 19, echovirus 20, echovirus 21, echovirus 24, echovirus 25, echovirus 26, echovirus 27, echovirus 29, echovirus 30, echovirus 31, echovirus 32, echovirus 33, enterovirus 68, enterovirus 69, enterovirus 70, enterovirus 71 and viluisk human encephalomyelitis virus. In some embodiments, a compound described herein (for example, a compound of Formula (I), or a pharmaceutically acceptable salt thereof) can ameliorate and/or treat an Enterovirus infection. For example, by administering an effective amount of a compound of Formula (I), or a pharmaceutically acceptable salt thereof, to a subject infected with the Enterovirus and/or by contacting a cell infected with the Enterovirus. In some embodiments, a compound described herein (for example, a compound of Formula (I), or a pharmaceutically acceptable salt thereof) can inhibit replication of an Enterovirus. In some embodiments, a compound of Formula (I), or a pharmaceutically acceptable salt thereof, can be effective against an Enterovirus, and thereby ameliorate one or more symptoms of an Enterovirus infection. In some embodiments, the Enterovirus can be Enterovirus A. In other embodiments, the Enterovirus can be Enterovirus B. In still other embodiments, the Enterovirus can be Enterovirus C. In yet still other embodiments, the Enterovirus can be Enterovirus D. In other embodiments, the Enterovirus can be Enterovirus E. In still other embodiments, the Enterovirus can be Enterovirus F. In yet still other embodiments, the Enterovirus can be Enterovirus G. In some embodiments, the Enterovirus can be Enterovirus H. In other embodiments, the Enterovirus can be Enterovirus J.

Coxsackieviruses are divided into group A and group B. Group A coxsackieviruses are noted to cause flaccid paralysis, while group B coxsackieviruses are noted to cause spastic paralysis. Over 20 serotypes of group A (CV-A1, CV-A2, CV-A3, CV-A4, CV-A5, CV-A6, CV-A7, CV-A8, CV-A9, CV-A10, CV-A11, CV-A12, CV-A13, CV-A14, CV-A15, CV-A16, CV-A17, CV-A18, CV-A19, CV-A20, CV-A21, CV-A22 and CV-A23) and 6 serotypes of group B (CV-B1, CV-B2, CV-B3, CV-B4, CV-B5 and CV-B6) are recognized. No specific treatment for coxsackievirus infections is currently approved. In some embodiments, a compound described herein (for example, a compound of Formula (I), or a pharmaceutically acceptable salt thereof) can ameliorate and/or treat a coxsackievirus infection. In some embodiments, a compound described herein (for example, a compound of Formula (I), or a pharmaceutically acceptable salt thereof) can inhibit replication of a coxsackievirus. In some embodiments, a compound of Formula (I), or a pharmaceutically acceptable salt thereof, can be effective against a coxsackievirus as demonstrated by the amelioration of one or more symptoms of a coxsackievirus infection. In some embodiments, a coxsackievirus infection can be ameliorated, treated and/or inhibited by administering an effective amount of a compound of Formula (I), or a pharmaceutically acceptable salt thereof, to a subject infected with the coxsackievirus and/or by contacting a cell infected with the coxsackievirus. In some embodiments, the coxsackievirus can be a coxsackievirus A. In other embodiments, the coxsackievirus can be a coxsackievirus B. In some embodiments, a compound described herein (one or more a compound of Formula (I), or a pharmaceutically acceptable salt thereof) can ameliorate and/or treat hand, food and mouth disease caused by a coxsackie A virus.

Additional species within the Enterovirus genus includes rhinovirus A, rhinovirus B and rhinovirus C. In some embodiments, a compound described herein (for example, a compound of Formula (I), or a pharmaceutically acceptable salt thereof) can ameliorate and/or treat a rhinovirus infection. In some embodiments, a compound described herein (for example, a compound of Formula (I), or a pharmaceutically acceptable salt thereof) can inhibit replication of a rhinovirus. In some embodiments, a compound described herein (for example, a compound of Formula (I), or a pharmaceutically acceptable salt thereof) can be effective against multiple serotypes of a rhinovirus. For example, a compound of Formula (I), or a pharmaceutically acceptable salt thereof, can be used to ameliorate and/or treat 2, 5, 10, 20, 40, 60, 80 or more serotypes of a rhinovirus. In some embodiments, a compound of Formula (I), or a pharmaceutically acceptable salt thereof, can be effective against rhinovirus, and thereby ameliorating one or more symptoms of a rhinovirus infection. In some embodiments, a rhinovirus infection can be ameliorated, treated and/or inhibited by administering an effective amount of a compound of Formula (I), or a pharmaceutically acceptable salt thereof, to a subject infected with the rhinovirus and/or by contacting a cell infected with the rhinovirus. In some embodiments, the rhinovirus can be rhinovirus A. In other embodiments, the rhinovirus can be rhinovirus B. In still other embodiments, the rhinovirus can be rhinovirus C.

Another species of Enterovirus is Hepatovirus. Hepatitis A is a serotype of Hepatovirus. Several human genotypes of Hepatitis A are known, IA, IB, IIA, IIB, IIIA and IIIB. Genotype I is the most common. To date, there is no specific therapy for treating a hepatitis A infection. Rather, treatment is supportive in nature. In some embodiments, a compound described herein (for example, a compound of Formula (I), or a pharmaceutically acceptable salt thereof) can ameliorate and/or treat a Hepatovirus infection, such as a hepatitis A virus infection. In some embodiments, a compound described herein (for example, a compound of Formula (I), or a pharmaceutically acceptable salt thereof) can inhibit replication of a Hepatovirus (for example, a hepatitis A virus). In some embodiment, a compound of Formula (I), or a pharmaceutically acceptable salt thereof, can treat and/or ameliorate a genotype I of hepatitis A. In some embodiments, a compound of Formula (I), or a pharmaceutically acceptable salt thereof, is effective against more than one genotype of hepatitis A, for example, 2, 3, 4, 5 or 6 genotypes of hepatitis A. In some embodiments, a Hepatovirus infection can be ameliorated, treated and/or inhibited by administering an effective amount of a compound of Formula (I), or a pharmaceutically acceptable salt thereof, to a subject infected with the Hepatovirus and/or by contacting a cell infected with the Hepatovirus.

Parechovirus is another species of Enterovirus. Serotypes of Parechovirus includes human parechovirus 1 (echovirus 22), human parechovirus 2 (echovirus 23), human parechovirus 3, human parechovirus 4, human parechovirus 5 and human parechovirus 6. In some embodiments, a compound described herein (for example, a compound of Formula (I), or a pharmaceutically acceptable salt thereof) can ameliorate and/or treat a parechovirus infection. In some embodiments, a compound described herein (for example, a compound of Formula (I), or a pharmaceutically acceptable salt thereof) can inhibit replication of a parechovirus. In some embodiments, a compound of Formula (I), or a pharmaceutically acceptable salt thereof, is effective against more than one serotype of a parechovirus. In some embodiments, a parechovirus infection can be ameliorated, treated and/or inhibited by administering an effective amount of a compound of Formula (I), or a pharmaceutically acceptable salt thereof, to a subject infected with the parechovirus and/or by contacting a cell infected with the parechovirus.

Other genera of Picornavirus include the following: Aquamavirus, Avihepatovirus, Cardiovirus, Cosavirus, Dicipivirus, Erbovirus, Kobuvirus, Megrivirus, Salivirus, Sapelovirus, Senecavirus, Teschovirus and Tremovirus. In some embodiments, a compound described herein (for example, a compound of Formula (I), or a pharmaceutically acceptable salt thereof) can ameliorate and/or treat a picornavirus infection caused by a virus selected from Aquamavirus, Avihepatovirus, Cardiovirus, Cosavirus, Dicipivirus, Erbovirus, Kobuvirus, Megrivirus, Salivirus, Sapelovirus, Senecavirus, Teschovirus and Tremovirus. In some embodiments, a compound described herein (for example, a compound of Formula (I), or a pharmaceutically acceptable salt thereof) can inhibit replication of a picornavirus selected from Aquamavirus, Avihepatovirus, Cardiovirus, Cosavirus, Dicipivirus, Erbovirus, Kobuvirus, Megrivirus, Salivirus, Sapelovirus, Senecavirus, Teschovirus and Tremovirus. A compound described herein (for example, a compound of Formula (I), or a pharmaceutically acceptable salt thereof) can ameliorate, treat and/or inhibit a virus selected from Aquamavirus, Avihepatovirus, Cardiovirus, Cosavirus, Dicipivirus, Erbovirus, Kobuvirus, Megrivirus, Salivirus, Sapelovirus, Senecavirus, Teschovirus and Tremovirus by administering an effective amount of a compound described herein to a subject infected by the virus and/or by contacting a cell infected with the virus with an effective amount of a compound described herein.

In some embodiments, an effective amount of a compound of Formula (I), or a pharmaceutically acceptable salt thereof, or a pharmaceutical composition that includes an effective amount of one or more compounds of Formula (I), or a pharmaceutically acceptable salt thereof, can be effective to treat more than one genera of Picornavirus. In some embodiments, a compound described herein (for example, a compound of Formula (I), or a pharmaceutically acceptable salt thereof) can be used to ameliorate and/or treat more than one species of a Picornavirus. As an example, a compound of Formula (I), or a pharmaceutically acceptable salt thereof, can be used to ameliorate and/or treat 2, 3, 4, 5, or more species of an Enterovirus. In some embodiments, a compound described herein (for example, a compound of Formula (I), or a pharmaceutically acceptable salt thereof) can be effective to treat multiple serotypes of a Picornavirus described herein. For example, a compound described herein (one or more a compound of Formula (I), or a pharmaceutically acceptable salt thereof) can be effective to treat 2, 5, 10, 15 or more serotypes of a coxsackie virus.

The one or more compounds of Formula (I), or a pharmaceutically acceptable salt thereof, that can be used to treat, ameliorate and/or prevent a picornavirus viral infection can be a compound of Formula (I), or pharmaceutically acceptable salt thereof, provided in any of the embodiments described in the paragraphs between the header "Compounds" to the header "Synthesis".

Various indicators for determining the effectiveness of a method for treating a Picornavirus viral infection are known to those skilled in the art. Example of suitable indicators include, but are not limited to, a reduction in viral load, a reduction in viral replication, a reduction in time to seroconversion (virus undetectable in patient serum), a reduction of morbidity or mortality in clinical outcomes, and/or other indicator(s) of disease response. Further indicators include one or more overall quality of life health indicators, such as reduced illness duration, reduced illness severity, reduced time to return to normal health and normal activity, and reduced time to alleviation of one or more symptoms. In some embodiments, a compound of Formula (I), or a pharmaceutically acceptable salt thereof, can result in the reduction, alleviation or positive indication of one or more of the aforementioned indicators compared to an untreated subject (picornavirus). Effects/symptoms of a Picornavirus infection are described herein, and include, but are not limited to, fever, blisters, rash, meningitis, conjunctivitis, acute hemorrhagic conjunctivitis (AHC), sore throat, nasal congestion, runny nose, sneezing, coughing, loss of appetite, muscle aches, headache, fatigue, nausea, jaundice, encephalitis, herpangina, myocarditis, pericarditis, meningitis, Bornholm disease, myalgia, nasal congestion, muscle weakness, loss of appetite, fever, vomiting, abdominal pain, abdominal discomfort, dark urine and muscle pain.

In some embodiments, a compound of Formula (I), or a pharmaceutically acceptable salt thereof, can result in a reduction in the length and/or severity of one or more symptoms associated with a Picornavirus virus infection compared to an untreated subject (picornavirus). Table 1 provides some embodiments of the percentage improvements obtained using a compound of Formula (I), or a pharmaceutically acceptable salt thereof, as compared to an untreated subject infected with a picornavirus. Examples include the following: in some embodiments, a compound of Formula (I), or a pharmaceutically acceptable salt thereof, results in a duration of illness that is in the range of about 10% to about 30% less than compared to the duration of illness experienced by an infected subject who is untreated; and in some embodiments, a compound of Formula (I), or a pharmaceutically acceptable salt thereof, results in a severity of a symptom (such as one of those described herein) that is 25% less than compared to the severity of the same symptom experienced by an infected subject who is untreated. Methods of quantifying the severity of a side effect and/or symptom are known to those skilled in the art.

TABLE 1

| Percentage of non-responders | Percentage of relapsers | Percentage of resistance | Percentage of viral load rebound | Number of side effects | Severity of side effect(s) |
|---|---|---|---|---|---|
| 10% less | 10% less | 10% less | 10% less | 10% less | 10% less |
| 25% less | 25% less | 25% less | 25% less | 25% less | 25% less |
| 40% less | 40% less | 40% less | 40% less | 40% less | 40% less |
| 50% less | 50% less | 50% less | 50% less | 50% less | 50% less |
| 60% less | 60% less | 60% less | 60% less | 60% less | 60% less |
| 70% less | 70% less | 70% less | 70% less | 70% less | 70% less |
| 80% less | 80% less | 80% less | 80% less | 80% less | 80% less |
| 90% less | 90% less | 90% less | 90% less | 90% less | 90% less |
| about 10% to about 30% less | about 10% to about 30% less | about 10% to about 30% less | about 10% to about 30% less | about 10% to about 30% less | about 10% to about 30% less |
| about 20% to about 50% less | about 20% to about 50% less | about 20% to about 50% less | about 20% to about 50% less | about 20% to about 50% less | about 20% to about 50% less |
| about 30% to about 70% less | about 30% to about 70% less | about 30% to about 70% less | about 30% to about 70% less | about 30% to about 70% less | about 30% to about 70% less |
| about 20% to about 80% less | about 20% to about 80% less | about 20% to about 80% less | about 20% to about 80% less | about 20% to about 80% less | about 20% to about 80% less |
| Duration of illness | Duration of illness | Duration of illness | Severity of symptom(s) | Severity of symptom(s) | Severity of symptom(s) |
| 10% less | 60% less | about 10% to about 30% less | 10% less | 60% less | about 10% to about 30% less |
| 25% less | 70% less | about 20% to about 50% less | 25% less | 70% less | about 20% to about 50% less |
| 40% less | 80% less | about 30% to about 70% less | 40% less | 80% less | about 30% to about 70% less |
| 50% less | 90% less | about 20% to about 80% less | 50% less | 90% less | about 20% to about 80% less |

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

As used herein, the terms "prevent" and "preventing," mean lowering the efficiency of viral replication and/or inhibiting viral replication to a greater degree in a subject who receives the compound compared to a subject who does not receive the compound. Examples of forms of prevention include prophylactic administration to a subject who has been or may be exposed to an infectious agent, such as a picornavirus (e.g., an enterovirus and/or a rhinovirus).

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the subject's overall feeling of well-being or appearance.

The terms "therapeutically effective amount" and "effective amount" are used to indicate an amount of an active compound, or pharmaceutical agent, that elicits the biological or medicinal response indicated. For example, an effective amount of compound can be the amount needed to prevent, alleviate or ameliorate symptoms of disease or prolong the survival of the subject being treated This response may occur in a tissue, system, animal or human and includes alleviation of the signs or symptoms of the disease being treated. Determination of an effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively dosages may be based and calculated upon the surface area of the patient, as understood by those of skill in the art. Although the exact dosage will be determined on a drugby-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject. In some embodiments, the compounds will be administered for a period of continuous therapy, for example for a week or more, or for months or years. In some embodiments, a compound of Formula (I), or a pharmaceutically acceptable salt thereof, can be administered less frequently compared to the frequency of administration of an agent within the standard of care. In some embodiments, a compound of Formula (I), or a pharmaceutically acceptable salt thereof, can be administered one time per day. For example, a compound of Formula (I), or a pharmaceutically acceptable salt thereof, can be administered one time per day to a subject suffering from a picornavirus viral infection. In some embodiments, the total time of the treatment regime with a compound of Formula (I), or a pharmaceutically acceptable salt thereof, can less compared to the total time of the treatment regime with the standard of care.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

As described herein, a compound of Formula (I), or a pharmaceutically acceptable salt thereof, can have a moiety(ies) that neutralize the charge of the phosphate or thiophosphate. By neutralizing the charge on the phosphate or thiophosphate, penetration of the cell membrane may be facilitated as a result of the increased lipophilicity of the compound. Once absorbed and taken inside the cell, the groups attached to the phosphorus can be easily removed by esterases, proteases and/or other enzymes. In some embodiments, the groups attached to the phosphorus can be removed by simple hydrolysis. Inside the cell, the phosphate thus released may then be metabolized by cellular enzymes to the diphosphate or the active triphosphate. Likewise, the thio-phosphate may be metabolized to the alpha-thiodiphosphate or the alpha-thiotriphosphate. Furthermore, in some embodiments, varying the substituents on a compound described herein, such as a compound of Formula (I), or a pharmaceutically acceptable salt thereof, can help maintain the efficacy of such the compound by reducing undesirable effects.

In some embodiments, varying the substituents on a compound described herein, such as a compound of Formula (I), or a pharmaceutically acceptable salt thereof, can result in the 5'-O-phosphorous being a chiral center. In some embodiments, the 5'-O-phosphorous can be in the (R)-configuration. In some embodiments, the 5'-O-phosphorous can be in the (S)-configuration. Examples of the two configurations are:

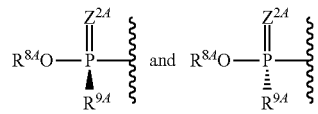

In some embodiments, a compound of Formula (I), or a pharmaceutically acceptable salt thereof, can be enriched in (R) or (S) configuration with respect to the 5'-O-phosphorous. For example, one of the (R) and (S) configuration with respect to the 5'-O-phosphorous atom can be present in an amount >50%, ≥75%, ≥90%, ≥95% or ≥99% compared to the amount of the other of the (R) or (S) configuration with respect to the 5'-O-phosphorous atom.

Additionally, the phosphorylation of a thio-monophosphate of a compound of Formula (I), or a pharmaceutically acceptable salt thereof, can be stereoselective. For example, a thio-monophosphate of a compound of Formula (I) can be phosphorylated to give an alpha-thiodiphosphate and/or an alpha-thiotriphosphate compound that can be enriched in the (R) or (S) configuration with respect to the 5'-O-phosphorous atom. For example, one of the (R) and (S) configuration with respect to the 5'-O-phosphorous atom of the alpha-thiodiphosphate and/or the alpha-thiotriphosphate compound can be present in an amount >50%, ≥75%, ≥90%, ≥95% or ≥99% compared to the amount of the other of the (R) or (S) configuration with respect to the 5'-O-phosphorous atom.

In some embodiments, a compound of Formula (I), or a pharmaceutically acceptable salt thereof, can act as a chain terminator of RNA synthesis. For example, compounds of Formula (I) can contain a moiety at the 2'-carbon position such that once the compound is incorporated into an RNA chain, no further elongation is observed to occur. For example, a compound of Formula (I), or a pharmaceutically acceptable salt thereof, can contain a non-hydrogen 2'-carbon modification such as a halogen, azido, an optionally substituted $C_{1-6}$ alkyl, an optionally substituted $C_{2-6}$ alkenyl or an optionally substituted $C_{2-6}$ alkynyl.

In some embodiments, a compound of Formula (I), or a pharmaceutically acceptable salt thereof, can have increased metabolic and/or plasma stability. In some embodiments, a compound of Formula (I), or a pharmaceutically acceptable salt thereof, can be more resistant to hydrolysis and/or more resistant to enzymatic transformations. For example, a compound of Formula (I), or a pharmaceutically acceptable salt thereof, can have increased metabolic stability, increased plasma stability, can be more resistant to hydrolysis and/or can be more resistant to enzymatic transformations compared to a compound that is identical in structure but for having $R^{1A}$ as H, $R^A$, $R^{2A}$, $R^{5A}$, $R^{a1}$ and $R^{a2}$ are each hydrogen and $R^{3A}$ and $R^{4A}$ are each OH. In some embodiments, a compound of Formula (I), or a pharmaceutically acceptable salt thereof, can have improved properties. A non-limiting list of example properties include, but are not limited to, increased biological half-life, increased bioavailability, increase potency, a sustained in vivo response, increased dosing intervals, decreased dosing amounts, decreased cytotoxicity, reduction in required amounts for treating disease conditions, reduction in viral load, reduction in time to seroconversion (i.e., the virus becomes undetectable in patient serum), increased sustained viral response, a reduction of morbidity or mortality in clinical outcomes, increased subject compliance, decreased liver conditions (such as liver fibrosis, liver cirrhosis and/or liver cancer), and compatibility with other medications. In some embodiments, a compound of Formula (I), or a pharmaceutically acceptable salt thereof, can have a biological half-life of greater than 24 hours. In some embodiments, a compound of Formula (I), or a pharmaceutically acceptable salt thereof, can have a biological half-life greater than a compound that is identical in structure but for having $R^{1A}$ as H, $R^A$, $R^{2A}$, $R^{5A}$, $R^{a1}$ and $R^{a2}$ are each hydrogen and $R^{3A}$ and $R^{4A}$ are each OH. In some embodiments, a compound of Formula (I), or a pharmaceutically acceptable salt thereof, can have more potent antiviral activity compared to a compound that is identical in structure but for having $R^{1A}$ as H, $R^A$, $R^{2A}$, $R^{5A}$, $R^{a1}$ and $R^{a2}$ are each hydrogen and $R^{3A}$ and $R^{4A}$ are each OH.

Additionally, in some embodiments, the presence of a moiety(ies) that neutralizes the charge of the phosphate or thiophosphate can increase the stability of the compound by inhibiting its degradation. Also, in some embodiments, the presence of a moiety(ies) that neutralizes the charge of the phosphate or thiophosphate can make the compound more resistant to cleavage in vivo and provide sustained, extended efficacy. In some embodiments, a moiety(ies) that neutralizes the charge of the phosphate or thiophosphate can facilitate the penetration of the cell membrane by a compound of Formula (I) by making the compound more lipophilic. In some embodiments, a moiety(ies) that neutralizes the charge of the phosphate or thiophosphate can have improved oral bioavailability, improved aqueous stability and/or reduced risk of byproduct-related toxicity. In some embodiments, for comparison purposes, a compound of Formula (I) can be compared to a compound that is identical in structure but for having $R^{1A}$ as H, $R^A$, $R^{2A}$, $R^{5A}$, $R^{a1}$ and $R^{a2}$ are each hydrogen and $R^{3A}$ and $R^{4A}$ are each OH.

Combination Therapies

In some embodiments, the compounds disclosed herein, such as a compound of Formula (I), or a pharmaceutically acceptable salt thereof, or a pharmaceutical composition that includes a compound described herein, or a pharmaceutically acceptable salt thereof, can be used in combination with one or more additional agent(s) for treating, ameliorating and/or inhibiting a Picornavirus viral infection.

In some embodiments, a compound of Formula (I), or a pharmaceutically acceptable salt thereof, can be administered with one or more additional agent(s) together in a single pharmaceutical composition. In some embodiments, a compound of Formula (I), or a pharmaceutically acceptable salt thereof, can be administered with one or more additional agent(s) as two or more separate pharmaceutical compositions. For example, a compound of Formula (I), or a pharmaceutically acceptable salt thereof, can be administered in one pharmaceutical composition, and at least one of the additional agents can be administered in a second pharmaceutical composition. If there are at least two additional agents, one or more of the additional agents can be in a first pharmaceutical composition that includes a compound of Formula (I), or a pharmaceutically acceptable salt thereof, and at least one of the other additional agent(s) can be in a second pharmaceutical composition.

The dosing amount(s) and dosing schedule(s) when using a compound of Formula (I), or a pharmaceutically acceptable salt thereof, or a pharmaceutical composition that includes a compound of Formula (I), or a pharmaceutically acceptable salt thereof, and one or more additional agents are within the knowledge of those skilled in the art. For example, when performing a conventional standard of care therapy using art-recognized dosing amounts and dosing schedules, a compound of Formula (I), or a pharmaceutically acceptable salt thereof, or a pharmaceutical composition that includes a compound of Formula (I), or a pharmaceutically acceptable salt thereof, can be administered in addition to that therapy, or in place of one of the agents of a combination therapy, using effective amounts and dosing protocols as described herein.

The order of administration of a compound of Formula (I), or a pharmaceutically acceptable salt thereof, with one or more additional agent(s) can vary. In some embodiments, a compound of Formula (I), or a pharmaceutically acceptable salt thereof, can be administered prior to all additional agents. In other embodiments, a compound of Formula (I), or a pharmaceutically acceptable salt thereof, can be administered prior to at least one additional agent. In still other embodiments, a compound of Formula (I), or a pharmaceutically acceptable salt thereof, can be administered concomitantly with one or more additional agent(s). In yet still other embodiments, a compound of Formula (I), or a pharmaceutically acceptable salt thereof, can be administered subsequent to the administration of at least one additional agent. In some embodiments, a compound of Formula (I), or a pharmaceutically acceptable salt thereof, can be administered subsequent to the administration of all additional agents.

In some embodiments, the combination of a compound of Formula (I), or a pharmaceutically acceptable salt thereof, in combination with one or more additional agent(s) can result in an additive effect. In some embodiments, the combination of a compound of Formula (I), or a pharmaceutically acceptable salt thereof, used in combination with one or more additional agent(s) can result in a synergistic effect. In some embodiments, the combination of a compound of Formula (I), or a pharmaceutically acceptable salt thereof, used in combination with one or more additional agent(s) can result in a strongly synergistic effect. In some embodiments, the combination of a compound of Formula (I), or a pharmaceutically acceptable salt thereof, in combination with one or more additional agent(s) is not antagonistic.

As used herein, the term "antagonistic" means that the activity of the combination of compounds is less compared to the sum of the activities of the compounds in combination when the activity of each compound is determined individually (i.e. as a single compound). As used herein, the term "synergistic effect" means that the activity of the combination of compounds is greater than the sum of the individual activities of the compounds in the combination when the activity of each compound is determined individually. As used herein, the term "additive effect" means that the activity of the combination of compounds is about equal to the sum of the individual activities of the compound in the combination when the activity of each compound is determined individually.

A potential advantage of utilizing a compound of Formula (I), or a pharmaceutically acceptable salt thereof, in combination with one or more additional agent(s) may be a reduction in the required amount(s) of one or more additional agent(s) that is effective in treating a disease condition disclosed herein (for example, picornavirus virus infection), as compared to the amount required to achieve same therapeutic result when one or more additional agent(s) are administered without a compound of Formula (I), or a pharmaceutically acceptable salt thereof. Another potential advantage of utilizing a compound of Formula (I), or a pharmaceutically acceptable salt thereof, in combination with one or more additional agent(s) is that the use of two or more compounds having different mechanism of actions can create a higher barrier to the development of resistant viral strains compared to the barrier when a compound is administered as monotherapy.

Additional advantages of utilizing a compound of Formula (I), or a pharmaceutically acceptable salt thereof, in combination with one or more additional agent(s) may include little to no cross resistance between a compound of Formula (I), or a pharmaceutically acceptable salt thereof, and one or more additional agent(s) thereof; different routes for elimination of a compound of Formula (I), or a pharmaceutically acceptable salt thereof, and one or more additional agent(s); little to no overlapping toxicities between a compound of Formula (I), or a pharmaceutically acceptable salt thereof, and one or more additional agent(s); little to no significant effects on cytochrome P450; little to no pharmacokinetic interactions between a compound of Formula (I), or a pharmaceutically acceptable salt thereof, and one or more additional agent(s); greater percentage of subjects achieving a sustained viral response compared to when a compound is administered as monotherapy and/or a decrease in treatment time to achieve a sustained viral response compared to when a compound is administered as monotherapy.

For treating of a picornavirus virus infection, examples of additional agents that can be used in combination with a compound of Formula (I), or a pharmaceutically acceptable salt thereof, or a pharmaceutical composition that includes a compound of Formula (I), or a pharmaceutically acceptable salt thereof, include, but are not limited to, ribavirin and an interferon (including those described herein).

EXAMPLES

Additional embodiments are disclosed in further detail in the following examples, which are not in any way intended to limit the scope of the claims.

Example 1

Preparation of Compound 14

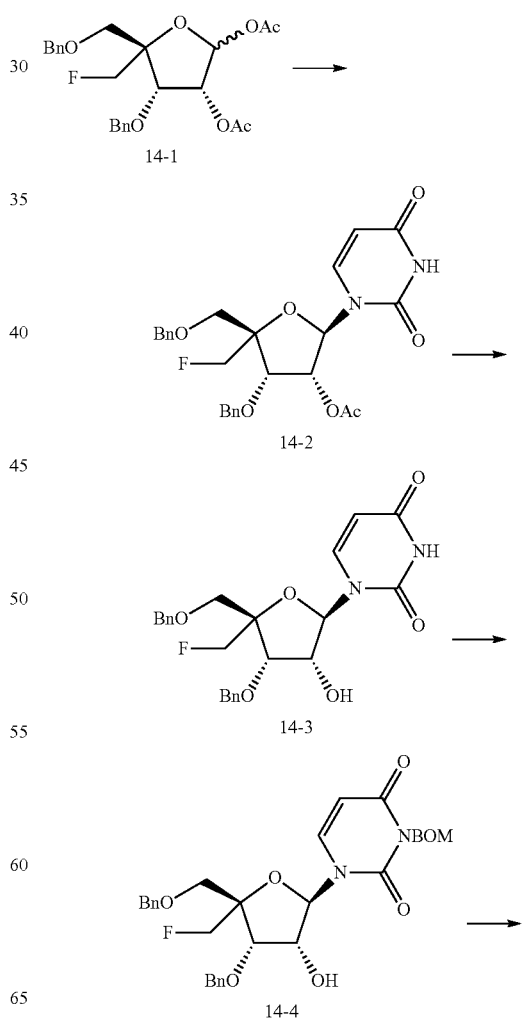

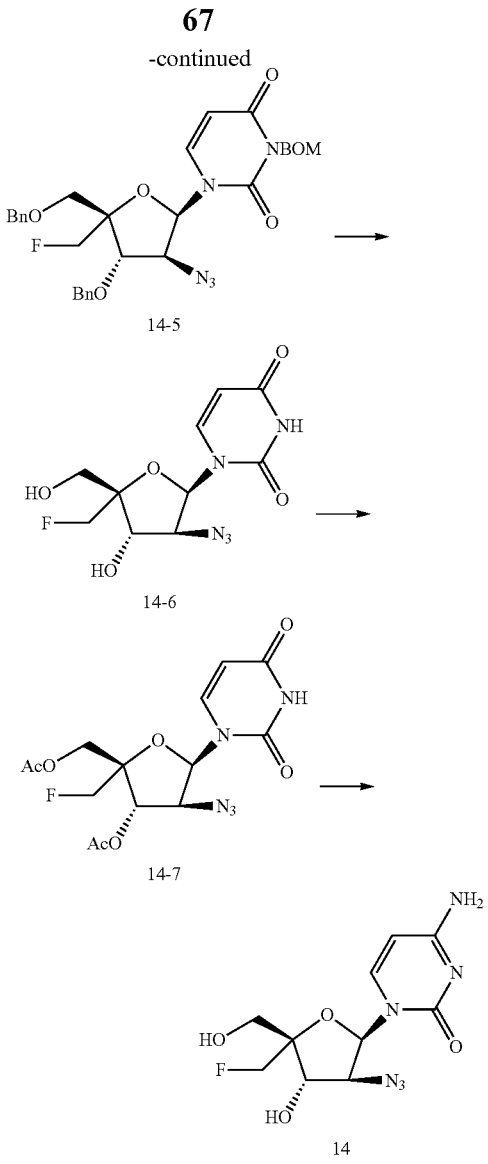

Into a 250-mL 3-necked round-bottom flask purged and maintained with an inert atmosphere of N₂, was placed a solution of uracil (500 mg, 4.46 mmol, 1.99 eq.) in MeCN (15 mL). N,O-Bis(trimethylsilyl)acetamide (2.7 g, 13.27 mmol, 5.93 eq.) added. The solution was stirred for 0.5 h at 80° C. in an oil bath. A solution of 14-1 (1 g, 2.24 mmol, 1.00 eq.) in MeCN (5 mL) was added dropwise with stirring at RT (room temperature). Tin tetrachloride (1.2 g, 4.62 mmol, 2.06 eq.) was added dropwise with stirring at RT. The solution was stirred for 0.5 h at 80° C. in an oil bath. The reaction was quenched by the addition of aq. sodium bicarbonate (200 mL) and extracted with EA (ethyl acetate) (2×200 mL). The combined organic layers were dried over anhydrous sodium sulfate. After concentrated under reduced pressure, the crude product was purified by a silica gel column with EA:PE (2:1). Compound 14-2 (1.1 g, 99%) was obtained as a white solid. MS (ESI): m/z 499 [M+H]⁺.

Into a 100-mL round-bottom flask, was placed a solution of 14-2 (3.7 g, 7.42 mmol, 1.00 eq.) in CH₃OH (30 mL). Sodium methoxide (30% in CH₃OH, 1 mL) was added. The solution was stirred for 6 h at 30° C. The pH value was adjusted to 7 with acetic acid. After concentrated under reduced pressure, the crude product was purified by a silica gel column with CH₂Cl₂:CH₃OH (20:1). Compound 14-3 (3.2 g, 94%) was obtained as a white solid. MS (ESI): m/z: 457 [M+H]⁺.

Into a 100-mL 3-necked round-bottom flask purged and maintained with an inert atmosphere of Ar, was placed a solution of 14-3 (4.16 g, 9.11 mmol, 1.00 eq.) in DMF (40 mL). 1,8-Diazabicyclo[5.4.0]undec-7-ene (4.16 g, 27.33 mmol, 2.00 eq.) was added followed by the dropwise addition of benzyloxymethyl chloride (2.14 g, 13.66 mmol, 1.50 eq.) with stirring at 0° C. The solution was stirred for 2 h at 0° C. in an ice bath. The reaction was quenched by the addition of CH₃OH (5 mL). The solution was diluted with CH₂Cl₂ (200 mL), washed with water (2×50 mL) and aq. NaCl (1×50 mL), dried over anhydrous sodium sulfate, filtered and concentrated under reduced pressure. The crude product was purified by a silica gel column with EA:PE (1:3). Compound 14-4 (4.05 g, 76%) was obtained as a light yellow oil. MS (ESI): m/z: 577 [M+H]⁺.

Into a 100-mL 2-necked round-bottom flask purged and maintained with an inert atmosphere of Ar, was placed a solution of 14-4 (1 g, 1.73 mmol, 1.00 eq.) and 4-dimethylaminopyridine (1.06 g, 8.68 mmol, 5.00 eq.) in CH₂Cl₂ (20 mL). Trifluoromethanesulfonyl chloride (1.06 g, 3.76 mmol, 2.00 eq.) was added dropwise with stirring at 0° C. The solution was stirred for 3 h at 25° C. The reaction was quenched with cooled aq. sodium bicarbonate, extracted with CH₂Cl₂ (2×50 mL). The combined organic layers were washed with aq. NaCl (5 mL) dried over anhydrous sodium sulfate and filtered. The solution was concentrated under reduced pressure. The crude triflate (~600 mg) was obtained. Into another 50-mL round-bottom flask purged and maintained with an inert atmosphere of Ar, was placed a solution of the triflate (600 mg, 0.85 mmol, 1.00 eq.) in DMF (6 mL). 15-Crown-5 (600 mg, 3.00 eq.) and sodium azide (330 mg, 5.08 mmol, 5.00 eq.) were added. The solution was stirred for 16 h at 25° C. The solution was then diluted with CH₂Cl₂ (50 mL), washed with water (25 mL) and aq. NaCl (25 mL), dried over anhydrous sodium sulfate and filtered. After concentrated under reduced pressure, the crude product was purified by a silica gel column with EA:PE (3:1). Compound 14-5 (230 mg, 21%) was obtained as an oil. MS (ESI): m/z: 602 [M+H]⁺.

Into a 25-mL round-bottom flask purged and maintained with an inert atmosphere of Ar, was placed a solution of 14-5 (400 mg, 0.66 mmol, 1.00 eq.) in CH₂Cl₂ (4 mL). Trichloroborane (1M in dichloromethane, 4 mL) was added dropwise with stirring at −78° C. The solution was stirred for 2 h at 25° C. The reaction was quenched by the addition of CH₃OH (4 mL). The solution was concentrated under reduced pressure. The crude product (200 mg) was purified by prep-HPLC with the following conditions: Column, X Bridge C18, 19*150 mm, 5 um; mobile phase, A: water/ammonium bicarbonate (10 mmol/L), Mobile Phase B: MeCN; Gradient: 5% B to 25% B in 10 min; Detector, 254 nm. Compound 14-6 (52.6 mg, 26%) was obtained as a white solid. MS (ESI): m/z: 302 [M+H]⁺.

Into a 50-mL round-bottom flask purged and maintained with an inert atmosphere of Ar, was placed a solution of 14-6 (300 mg, 1.00 mmol, 1.00 eq.) in pyridine (3 mL). Acetyl acetate (300 mg, 2.94 mmol, 3.00 eq.) was added. The solution was stirred for 16 h at 25° C. After concentrated under reduced pressure, the residue was diluted with CH₂Cl₂ (50 mL), washed with 1N aq. HCl (25 mL) and aq. NaCl (25 mL), dried over anhydrous sodium sulfate and filtered. After concentrated under reduced pressure, the crude product was purified by a silica gel column with EA:PE (1:1). Compound 14-7 (305 mg, 78%) was obtained as a white solid. MS (ESI): m/z: 386 [M+H]+.

Into a 50-mL round-bottom flask purged and maintained with an inert atmosphere of Ar, was placed a solution of 14-7 (350 mg, 0.91 mmol, 1.00 eq.) in MeCN (7 mL). N,N-dimethylpyridin-4-amine (150 mg, 1.23 mmol, 1.00 eq.), triethylamine (275 mg, 2.72 mmol, 3.00 eq.) and 2,4,6-triisopropylbenzenesulfonyl chloride (826 mg, 2.73 mmol, 3.00 eq.) were added. The solution was stirred for 2 h at 25° C. Ammonium hydroxide (7 mL, 28%) was added, and the solution was stirred for 2 h at 25° C. After concentrated under reduced pressure, the crude product (1.3 g) was purified by prep-HPLC with the following conditions: Column, X Bridge C18, 19*150 mm, 5 um; mobile phase, A: Water/ammonium bicarbonate (10 mmol/L), Mobile Phase B: MeCN; Gradient: 5% B to 15% B in 10 min; Detector, 254 nm. Compound 14 (60.4 mg, 22%) was obtained as a white solid. MS (ESI): m/z: 301 [M+H]+.

Example 2

Preparation of Compound 2

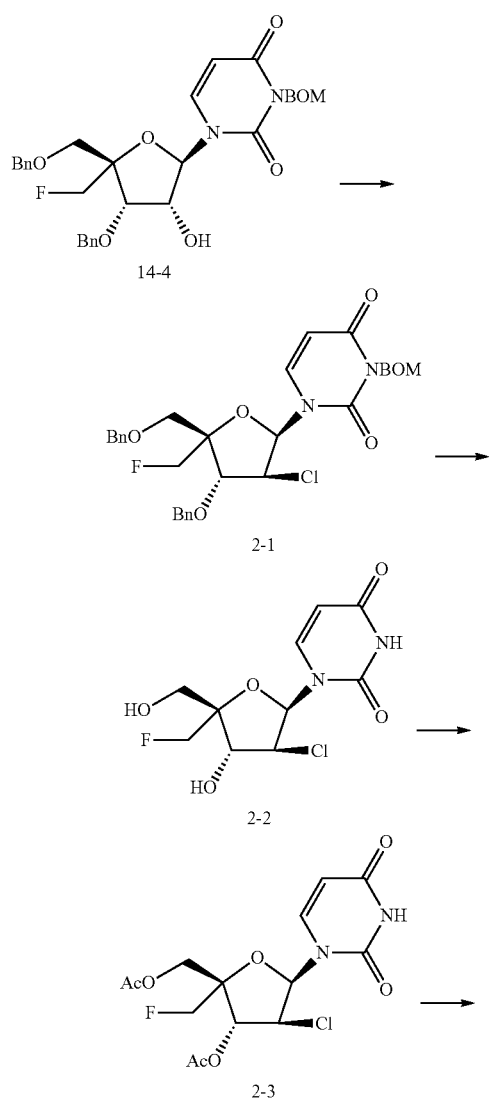

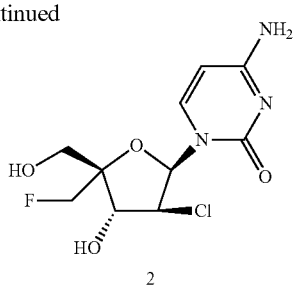

Into a 100-mL round-bottom flask purged and maintained with an inert atmosphere of Ar, was placed a solution of 14-4 (2 g, 3.47 mmol, 1.00 eq.) in THF (60 mL). 4-dimethylaminopyridine (2.12 g, 17.35 mmol, 5.00 eq.) was added. A solution of trifluoromethanesulfonyl chloride (1.17 g, 6.94 mmol, 2.00 eq.) in THF (5 mL) was then added dropwise with stirring at 0° C. The solution was stirred for 2 h at 25° C. The reaction was quenched with aq. sodium bicarbonate (20 mL) and extracted with CH$_2$Cl$_2$ (2×100 mL). The combined organic layers were washed with 1 N aq. HCl (50 mL) and aq. NaCl (50 mL), dried over anhydrous sodium sulfate and filtered. After concentrated under reduced pressure, the crude product was purified by a silica gel column with EA:PE (1:3). Compound 2-1 (630 mg, 31%) was obtained as a white solid. MS (ESI): m/z: 595 [M+H]+.

Into a 25-mL round-bottom flask, was placed a solution of 2-1 (350 mg, 0.59 mmol, 1.00 eq.) in CH$_2$Cl$_2$:CH$_3$OH (10 mL, 1:1). Palladium hydroxide on carbon (350 mg) was added. The mixture was stirred for 16 h at 25° C. under H$_2$. The solids were filtered off. The solution was concentrated under reduced pressure. The crude product (175 mg) was purified by prep-HPLC with the following conditions: Column, X Bridge C18, 19*150 mm, 5 um; mobile phase, A: water/ammonium bicarbonate (10 mmol/L), Mobile Phase B: MeCN; Gradient: 5% B to 25% B in 15 min; Detector, 254 nm. Compound 2-2 (58.9 mg, 34%) was obtained as a white solid. MS (ESI): m/z: 295 [M+H]+.

Into a 25-mL round-bottom flask purged and maintained with an inert atmosphere of Ar, was placed a solution of 2-2 (300 mg, 1.02 mmol, 1.00 eq.) in pyridine (5 mL). Acetic anhydride (322 mg, 3.15 mmol, 3.00 eq.) was added. The solution was stirred for 3 h at 25° C. The reaction was quenched by CH$_3$OH (1 mL). The solution was diluted with CH$_2$Cl$_2$ (100 mL), washed with 1 N aq. HCl (20 mL) and aq. NaCl (20 mL), dried over anhydrous sodium sulfate and filtered. The solution was concentrated under reduced pressure to give 2-3 (300 mg, 78%) as a white solid. MS (ESI): m/z: 379 [M+H]+.

Into a 50-mL round-bottom flask purged and maintained with an inert atmosphere of Ar, was placed a solution of 2-3 (300 mg, 0.79 mmol, 1.00 eq.) in MeCN (5 mL). 4-dimethylaminopyridine (96.8 mg, 0.79 mmol, 1.00 eq.) and triethylamine (240 mg, 2.37 mmol, 3.00 eq.) were added. 2,4,6-Triisopropylbenzenesulfonyl chloride (721 mg, 2.38 mmol, 3.00 eq.) was then added. The solution was stirred for 2 h at 25° C. and then ammonium hydroxide (5 mL, 28%) was added. The solution was stirred for 2 h at 25° C. The solution was concentrated under reduced pressure. The crude product (1.1 g) was purified by prep-HPLC with the following conditions: Column, X Bridge C18, 19*150 mm, 5 um; mobile phase, A: water/ammonium hydroxide (10 mmol/L), Mobile Phase B: MeCN; Gradient: 5% B to 15% B in 10 min; Detector, 254 nm. Compound 2 (51.8 mg, 22%) was obtained as a white solid. MS (ESI): m/z: 294 [M+H]$^+$.
Example 3
Preparation of Compound 3
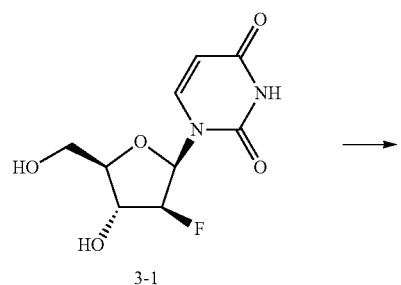
3-1
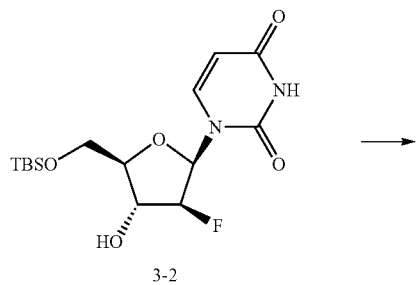
3-2
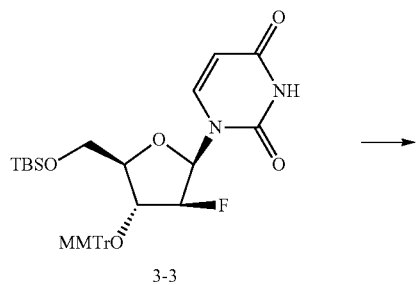
3-3
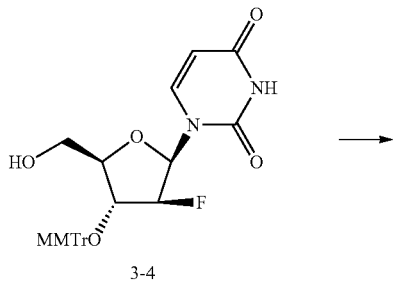
3-4
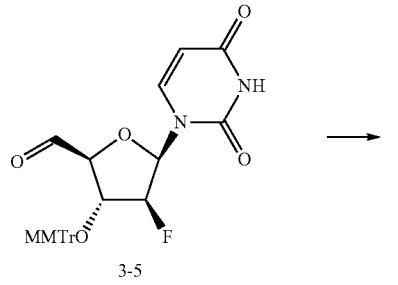
3-5
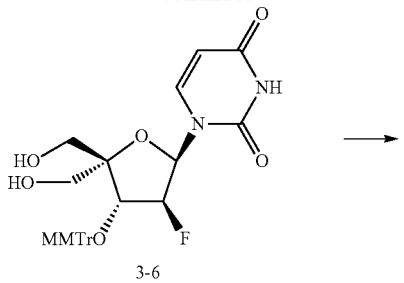
3-6
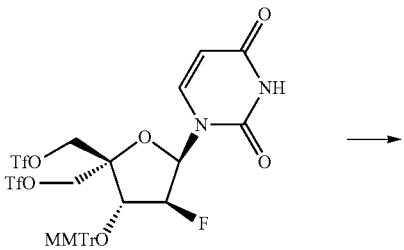
3-7
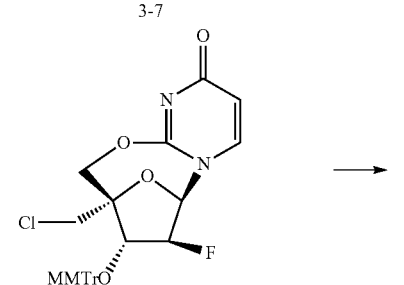
3-8
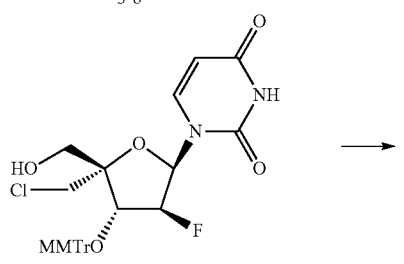
3-9
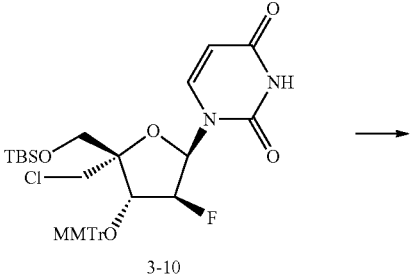
3-10
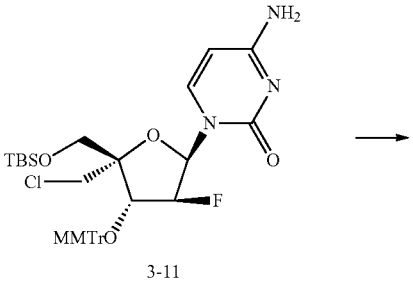
3-11

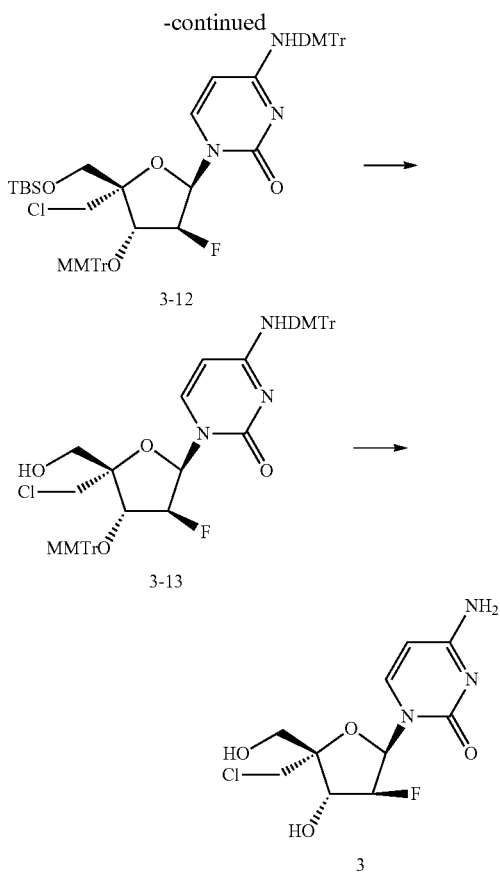

3-12

3-13

3

To a solution of 3-1 (8.67 g, 35.2 mmol) in anhydrous pyridine (50 mL) was added TBSCl (5.84 g, 38.7 mmol). The reaction was stirred over 18 h. at 20° C. The solution was concentrated under reduced pressure, and the residue was partitioned between EA and water. The organic layer was separated, washed with brine, and dried over anhydrous sodium sulfate. The solution was concentrated under reduced pressure to give 3-2 (12 g, 95%) as white foam.

To a solution of the 3-2 (12 g, 33.3 mmol) in anhydrous DCM (100 mL) were added AgNO$_3$ (11.8 g, 69.4 mmol) and collidine (12.6 g, 0.1 mol), and the mixture was stirred at 20° C. The mixture was cooled to 0° C. and MMTrCl (11.8 g, 38.2 mmol) was added. After being stirred 18 h at RT, the solid was filtered. The filtrate was washed with HCl solution (0.1 N) and brine. The organic solution was dried over anhydrous MgSO$_4$ and concentrated under vacuum to give 3-3, which was used directly for next step.

Crude 3-3 was dissolved in THF (150 mL) and TBAF (10.8 g, 42 mmol) was added. The reaction was stirred at 20° C. for 12 h. The mixture was evaporated at low pressure, and the residue was purified by silica gel directly to give 3-4 (13.8 g, 81%, over 2 steps) as a slightly yellow solid.

To a solution of 3-4 (13 g, 25 mmol) in DCM (100 mL) was added pyridine (6.9 g, 87 mmol). The solution was cooled to 0° C., and then Dess-Martin periodinane (13.5 g, 32 mmol) was added as a single portion. The reaction was stirred at RT over 18 h. The reaction was quenched with 4% Na$_2$S$_2$O$_3$/4% Na$_2$CO$_3$ aqueous solution (adjusted pH to ~6). The mixture was stirred for 15 mins. The organic layer was separated and washed with brine. The solution was concentrated under reduced pressure, and the residue was purified by silica gel to afford 3-5 (9.5 g, 73%) as a yellow oil.

To a solution of 3-5 (9.5 g, 18.4 mmol) in dioxane (50 mL) was added 37% aq. formaldehyde (10 mL) and aq. NaOH (2 N, 20 mL), and the mixture was stirred at RT overnight. The mixture was then cooled to 0° C. and treated with sodium borohydride (3.5 g, 84 mmol). After stirring for 30 mins at RT, the reaction was quenched by sat. aq. NH$_4$Cl. The residue was dissolved in EA (60 mL). The solution was washed brine and dried over anhydrous MgSO$_4$. The organic solvent was concentrated under reduced pressure. The residue was purified by silica gel to afford 3-6 (8.0 g, 83%) as a yellow oil.

Compound 3-6 (5.0 g, 9.1 mmol) was co-evaporated with toluene (2×). The residue was dissolved in anhydrous DCM (30 mL) and pyridine (3.6 g, 45.5 mmol). The solution was cooled to −35° C., and then triflic anhydride (5.66 g, 20.1 mmol) was added dropwise over 10 mins. The mixture was slowly warmed to RT and then stirred at RT for 1.5 h. The reaction was quenched with water, and the mixture was washed with sodium bicarbonate. The organic layer was dried over anhydrous MgSO$_4$ and concentrated at low pressure. The residue was purified by silica gel to afford 3-7 (5.5 g, 75%) as a yellow foam.

Compound 3-7 (5.5 g, 6.77 mmol) was dissolved in anhydrous DMF (20 mL). The solution was cooled to 0° C. and then treated with NaH (60% in mineral oil, 0.3 g, 7.44 mmol). The mixture was stirred at RT for 1 h. LiCl (0.86 g, 20.3 mmol) was added, and the mixture was stirred for 2 h. The mixture was evaporated by vacuum to afford crude 3-8, which was used directly for next step.

To a solution of 3-8 in THF (40 mL) was added NaOH (2.0 N, 5.5 mL), and the mixture stirred at RT for 2 h. After the solvent was evaporated at low pressure, the residue was dissolved in DCM (40 mL). The solution was washed with sat. aq. NH$_4$Cl and brine. The organic layer was dried over anhydrous MgSO$_4$ and concentrated at low pressure. The residue was purified by silica gel to afford 3-9 (3.75 g, 83%).

To a solution of 3-9 (3.75 g, 6.6 mmol) and imidazole (0.676 g, 9.9 mmol) in DCM (30 mL) was added TBSCl (1.1 g, 7.3 mmol) and AgNO$_3$ (1.68 g, 9.9 mmol), and the mixture stirred at RT overnight. After the solid was filtered off, the filtrate was washed with sat. aq. Na$_2$CO$_3$. The organic layer was washed with sat. aq. NH$_4$Cl, dried over anhydrous MgSO$_4$ and concentrated at low pressure. The residue was purified by silica gel to afford 3-10 (2.7 g, 60%) as a yellow solid.

To a solution of 3-10 (2.25 g, 3.3 mmol) in MeCN was added DMAP (0.8 g, 6.6 mmol) and TEA (0.67 g, 6.6 mmol), and the mixture stirred at RT for 10 mins. The mixture was treated with TPSCl (2.0 g, 6.6 mmol) and then stirred for 30 mins. NH$_3$—H$_2$O (20 mL) was added, and the solution was stirred for 1 h. The mixture was evaporated at low pressure, and the residue was purified by silica gel to afford 3-11 (2.0 g, 88%).

To a solution of 3-11 (2.6 g, 3.82 mmol) and collidine (1.4 g, 11.5 mmol) in anhydrous DCM (40 mL) was added DMTrCl (3.88 g, 11.5 mmol) and AgNO$_3$ (1.95 g, 11.5 mmol) at 0° C. The mixture was stirred at RT under N$_2$ for 2 h. The mixture was filtered, and the filtrate was evaporated at low pressure. The residue was purified by silica gel to afford 3-12 (2.8 g, 75%) as a slightly yellow oil.

A mixture of 3-12 (2.5 g, 2.54 mmol) and TBAF (0.73 g, 2.8 mmol) in THF was stirred at RT for 2 h. The mixture was evaporated at low pressure, and the residue was purified by silica gel to afford 3-13 (1.9 g, 86%).

Compound 3-13 (1.5 g, 1.53 mmol) was dissolved in CH$_3$COOH (80%, 20 mL). The mixture was stirred at 60-70° C. for 2 h. The reaction was quenched with CH$_3$OH, and the mixture was concentrated at low pressure. The residue was purified by silica gel to afford 3 (0.32 g, 70%) as a white solid. MS (ESI): m/z: 293.9 [M+H]⁺.

Example 4

Preparation of Compound 4

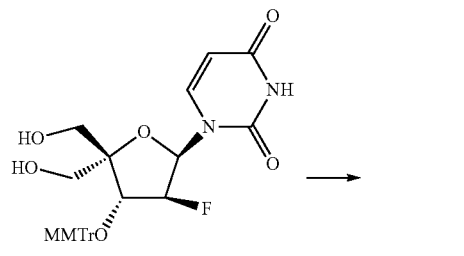
4-1

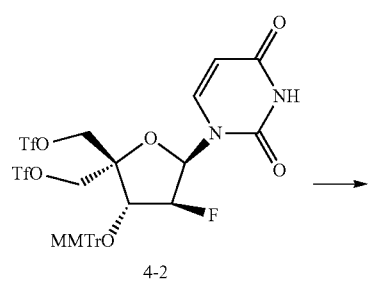
4-2

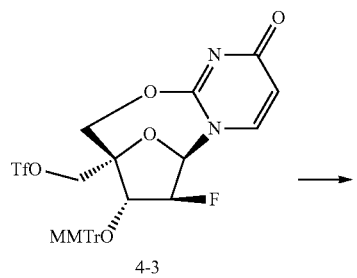
4-3

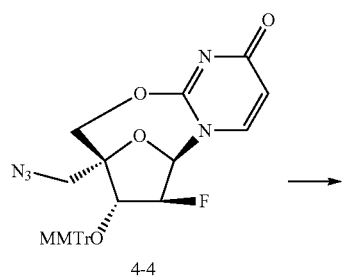
4-4

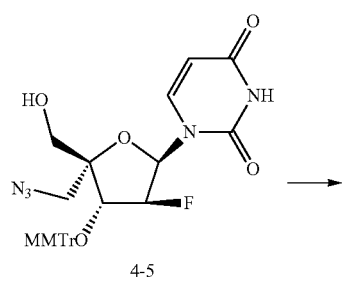
4-5

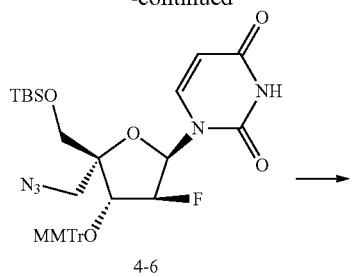
4-6

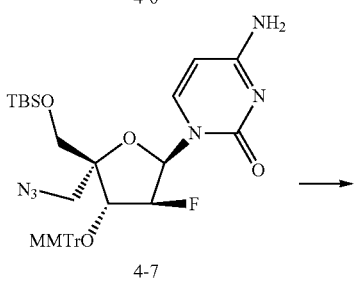
4-7

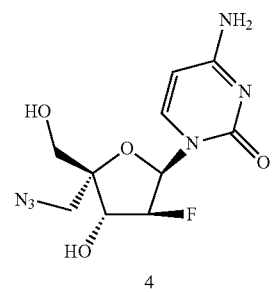
4

To a stirred solution of 4-1 (2.8 g, 5.21 mmol) in DCM (25 mL) was added pyridine (2.1 g, 26.07 mmol) at 25° C. The solution was cooled to −35° C., and then Tf₂O (3.2 g, 11.47 mmol) was added dropwise. The mixture was stirred at −35° C.~25° C. for 2 h. The reaction was quenched with H₂O at 25° C. The mixture was extracted with DCM. The organic layer was washed with a sat. sodium bicarbonate solution, dried over anhydrous MgSO₄, and concentrated at low pressure. The residue was purified by column chromatography PE:EA=10:1 to 0:1). Compound 4-2 (3.0 g, 71.5%) was obtained as a black brown solid.

To a solution of 4-2 (3.0 g, 3.72 mmol) in DCM (30 mL) was added TEA (755 mg, 7.45 mmol). The mixture was stirred at 25° C. for 6 h. The mixture was concentrated under reduced pressure, and the residue was purified by column chromatography (PE:EA=5:1 to 1:1). Compound 4-3 (2.2 g, 69%) was obtained as a black brown solid.

To a solution of 4-3 (2 g, 3.02 mmol) in DMF (20 mL) was added NaN₃ (785 mg, 12.08 mmol). The mixture was stirred at 25° C. for 1 h. The mixture was diluted with EA (40 mL). The solution was washed with brine and dried over anhydrous MgSO₄. The organic layer was concentrated under reduced pressure. Crude 4-4 (1.7 g) was used for the next step without further purification.

To a solution of 4-4 (1.7 g, crude) in THF (17 mL) was added NaOH (2 M, 2 mL). The mixture was stirred at 25° C. for 5 h. The mixture was diluted with H₂O and extracted with EA (3×40 mL). The combined organic layers were washed with NH₄Cl, filtered and concentrated under reduced pressure to give a residue. The residue was purified by column chromatography (PE:EA=8:1 to 2:1). Compound 4-5 (719 mg, 41.1%) was obtained as a light brown solid.

To a solution of 4-5 (719 mg, 1.25 mmol) in CH$_2$Cl$_2$ (5 mL) was added imidazole (299 mg, 4.38 mmol) and TBSCl (472 mg, 3.13 mmol). The mixture was stirred at 25° C. for 4 h. The reaction mixture was diluted with water and extracted with CH$_2$Cl$_2$ (3×20 mL). The organic layer was dried over anhydrous MgSO$_4$ and concentrated at low pressure. The residue was purified by column chromatography (PE:EA=8:1 to 3:1). Compound 4-6 (640 mg, 74.2%) was obtained as a light yellow solid.

To a solution of 4-6 (640 mg, 0.93 mmol) in MeCN (6 mL) was added DMAP (284 mg, 2.32 mmol), TEA (235 mg, 2.32 mmol) and 2,4,6-triisopropylbenzenesulfonyl chloride (704 mg, 2.32 mmol). The mixture was stirred at 25° C. for 1 h. NH$_3$.H$_2$O (5 mL) was added, and the mixture was stirred at 25° C. for 1 h. The mixture was diluted with H$_2$O and extracted with EA (3×20 mL). The organic layer was dried over anhydrous MgSO$_4$, and concentrated at low pressure. The residue was purified by column chromatography (PE: EA=5:1 to 1:1). Compound 4-7 (461 mg, 72.1%) was obtained as a light yellow solid.

A solution of 4-7 (250 mg, 363.98 μmol) in HCOOH (4 mL) was stirred at 50° C. for 16 h. The mixture was concentrated under reduced pressure, and the residue was dissolved in CH$_3$OH (3 mL). NH$_3$/CH$_3$OH (7 M, 1 mL) was added, and the mixture was stirred at 25° C. for 4 h. The mixture was concentrated under reduced pressure, and the residue was purified by column chromatography (DCM: CH$_3$OH=50:1 to 10:1). Compound 4 (85 mg, 77%) was obtained as a white solid. MS (ESI): m/z: 301.1 [M+H]$^+$.

Example 5

Preparation of Compound 5

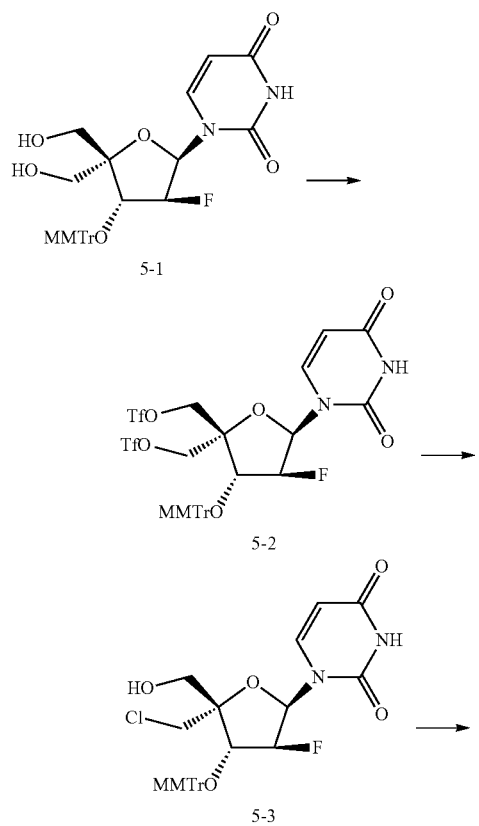

5-1

5-2

5-3

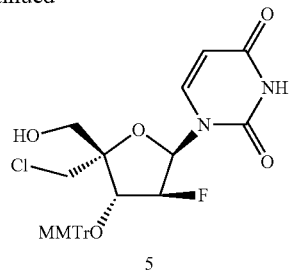

5

To an ice-cold solution of 5-1 (2.00 g, 1.82 mmol, 1.00 eq.) in anhydrous DCM (10.00 mL) was added pyridine (1.44 g, 18.23 mmol, 10.00 eq.). A solution of trifluoromethylsulfonyl trifluoromethanesulfonate (1.18 g, 4.19 mmol, 2.30 eq.) in DCM (3.50 mL) was added by dropwise at 0° C. The mixture was stirred at 0° C. for 0.5 h. The mixture was concentrated under reduced pressure to give a residue. The residue was purified by column chromatography (20% EA in PE) to give 5-2 (2.00 g, 67.61%) as a white solid.

To a solution of 5-2 (2.00 g, 1.23 mmol, 1.00 eq.) in anhydrous DMF (10.00 mL) was added NaH (59 mg, 1.48 mmol, 1.20 eq.) at 0° C. under N$_2$. The mixture was stirred at 20° C. for 1 h. The mixture was treated with LiCl (156 mg, 3.69 mmol, 3.00 eq.) at 0° C. The reaction was stirred at 20° C. for 2 h. The mixture was diluted with EA (50 mL), and washed with sat. NH$_4$Cl solution. The solution was dried over anhydrous Na$_2$SO$_4$, filtered and concentrated under reduced pressure. The residue was used for the next step without further purification.

The residue was dissolved in THF (10.00 mL). The mixture was treated with NaOH solution (1 M, 1.35 mL, 1.10 eq.) at 20° C. The mixture was stirred at the same temperature for 1 h. The reaction was diluted with EA (30 mL), and washed with a sat. NH$_4$Cl solution. The organic layer was dried over anhydrous MgSO$_4$, filtered and concentrated under reduced pressure. The residue was purified by column chromatography (30% EA in PE) to give 5-3 (740 mg, 53.05%) as a white solid.

Compound 5-3 (300 mg, 529.10 μmol, 1.00 eq.) was dissolved in 80% CHOOH (10.00 mL), and the mixture was stirred at 20° C. for 16 h. The mixture was concentrated under reduced pressure. The residue was purified by column chromatography (5% CH$_3$OH in DCM) to give the crude product. The crude product was purified by prep-HPLC (neutral condition) to give 5 (71 mg, 45.54%) as a white solid. MS (ESI): m/z: 295 [M+H]$^+$.

Example 6

Preparation of Compound 6

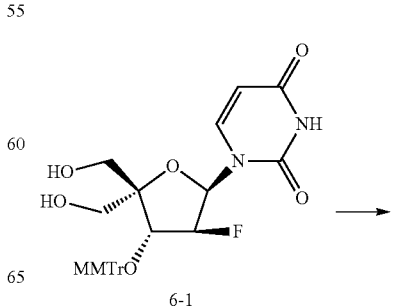

6-1

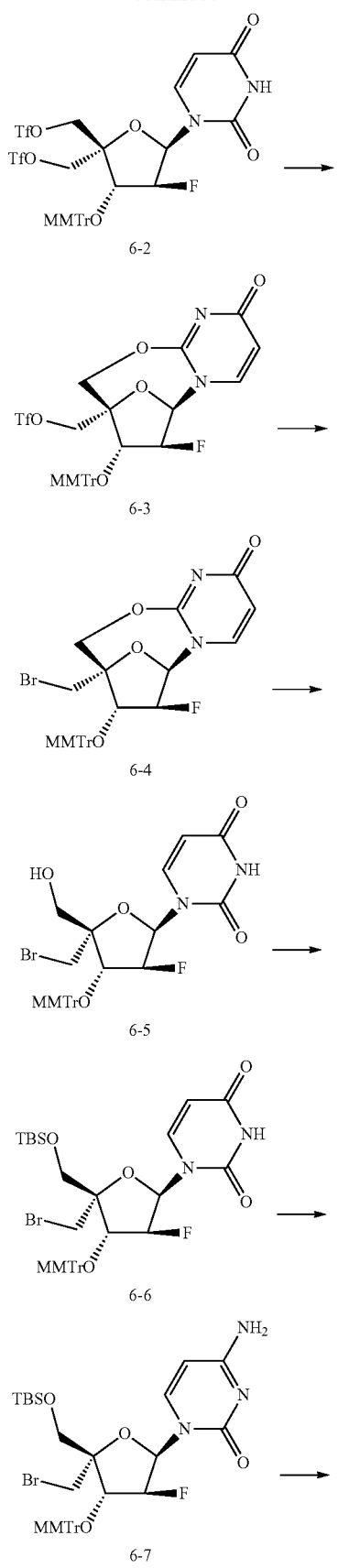

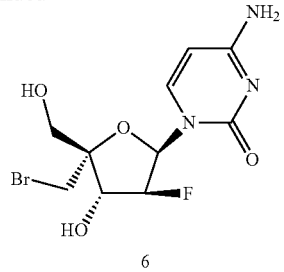

To a solution of 6-1 (2.9 g, 5.21 mmol) in DCM (25 mL) was added Pyridine (2.1 g, 26.07 mmol) at 25° C. The solution was cooled to −35° C., and then Tf$_2$O (3.2 g, 11.47 mmol) was added dropwise. The mixture was stirred at −35° C.∼25° C. for 2 h. The reaction was quenched with H$_2$O and extracted with DCM (3×50 mL). The solution was washed with sat. sodium bicarbonate solution and brine. The organic layer was dried over anhydrous MgSO$_4$, and concentrated at low pressure. The residue was purified by column chromatography (PE:EA=10:1 to 0:1). Compound 6-2 (3.0, 71.5%) was obtained as a black brown solid.

To a solution of 6-2 (3.0 g, 3.72 mmol) in DCM (30 mL) was added TEA (755 mg, 7.45 mmol). The mixture was stirred at 25° C. for 6 h. The mixture was concentrated under reduced pressure, and the residue was purified by column chromatography (PE:EA=5:1 to 1:1). Compound 6-3 (2.2 g, 69%) was obtained as a black brown solid.

To a solution of 6-3 (730 mg, 1.10 mmol) in DMF (7 mL) was added LiBr (287 mg, 3.30 mmol). The mixture was stirred at 25° C. for 16 h. The mixture was concentrated under reduced pressure. Crude 6-4 (653 mg) was used for the next step without further purification.

To a solution of 6-4 (653 mg, 1.10 mmol) in THF (6 mL) was added NaOH solution (2 M, 600 µL). The mixture was stirred at 25° C. for 6 h. After the solvent was evaporated at low pressure, the residue was dissolved in EA (40 mL) and washed with sat. NH$_4$Cl solution and brine. The organic layer was dried over anhydrous MgSO$_4$, and concentrated at low pressure. The residue was purified by column chromatography (PE:EA=10:1 to 2.5:1). Compound 6-5 (281 mg, 41.7%) was obtained as a light yellow solid.

To a solution of 6-5 (281 mg, 459 µmol) in pyridine (2.5 mL) was added TBSCl (121 mg, 804 µmol) and imidazole (78 mg, 1.15 mmol) at 25° C. The mixture was stirred at 60° C. for 4 h. The mixture was diluted with water and extracted with CH$_2$Cl$_2$ (20 mL). The organic layer was washed with brine, dried over anhydrous Na$_2$SO$_4$ and concentrated under reduced pressure. The residue was purified by column chromatography (PE:EA=5:1 to 1:1). Compound 6-6 (204 mg, 61.1%) was obtained as light yellow solid.

To a solution of 6-6 (204 mg, 281 µmol) in anhydrous MeCN (1.5 mL) were added 2,4,6-triisopropylbenzenesulfonyl chloride (213 mg, 702 µmol), DMAP (85 mg, 702 µmol) and TEA (71 mg, 702 µmol) at 25° C. The mixture was stirred at 25° C. for 2 h. NH$_3$.H$_2$O (3 mL) was added, and the mixture was stirred for 1 h. The mixture was diluted with EA and washed with water. The organic layer was dried over anhydrous MgSO$_4$, and concentrated at low pressure. The residue was purified by column chromatography (PE:EA=10:1 to 0:1). Compound 6-7 (180 mg, 88.3%) was obtained as a light yellow solid.

A solution of 6-7 (180 mg, 248.36 µmol) in HCOOH (1 mL) was stirred at 25∼50° C. for 17 h. The mixture was concentrated under reduced pressure. The residue was dissolved in CH$_3$OH (2 mL) and NH$_3$/CH$_3$OH (7 M, 800 μL). The mixture was stirred at 25° C. for 1 h. The =mixture was concentrated under reduced pressure. The residue was purified by column chromatography (DCM:CH$_3$OH=30:1 to 10:1). Compound 6 (76 mg, 90.2%) was obtained as a white solid. MS (ESI): m/z: 677.1 [2M+H]$^+$.

Example 7

Preparation of Compound 7

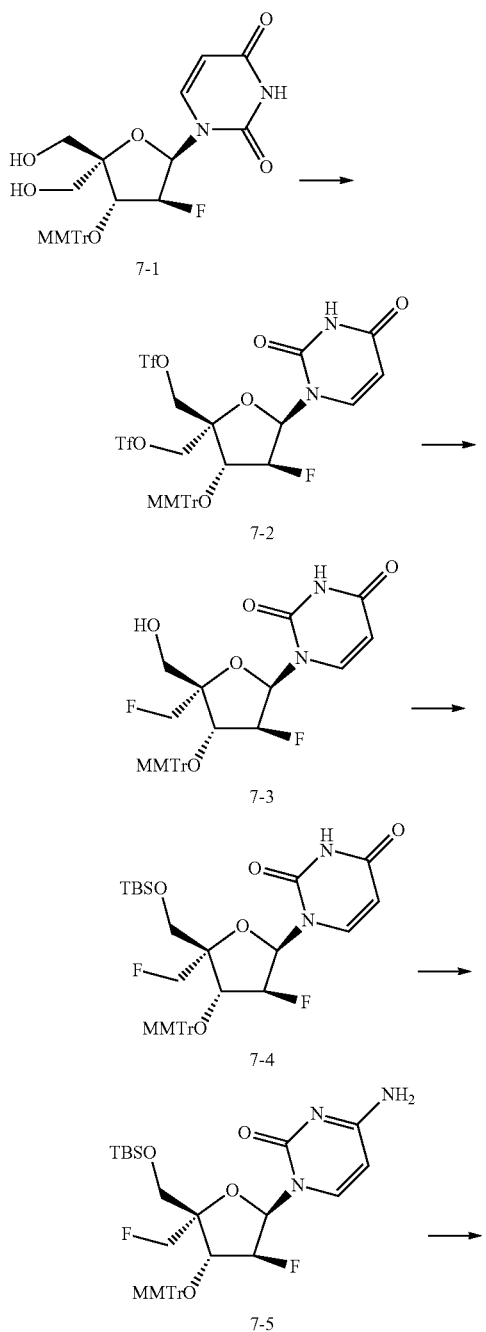

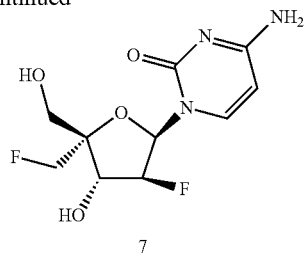

To a solution of 7-1 (1.0 g, 1.8 mmol) in DCM (10 mL) was added pyridine (1.4 g, 18.2 mmol) and Tf$_2$O (1.1 g, 4.0 mmol) dropwise at 0° C. The mixture was stirred at 0° C. for 1 h. The reaction was quenched with H$_2$O (30 mL) at 0° C. The mixture was extracted with DCM (2×20 mL). The combined organic layers were dried over Na$_2$SO$_4$, filtered and concentrated under reduced pressure to give a residue. The residue was purified by column chromatography (10% EA in PE) to give 7-2 (1.2 g, 1.4 mmol, 77%) as a yellow solid.

To a solution of 7-2 (1.2 g, 1.4 mmol) in MeCN (5 mL) was added TBAF (1 M, 7 mL). The mixture was stirred at 20° C. for 12 h. NaOH (aq.) (1 M, 3 mL) was added, and the mixture was stirred at 20° C. for 1 h. The reaction was quenched with a sat. NH$_4$Cl solution (40 mL) at 0° C. The mixture was extracted with EtOAc (2×30 mL). The combined organic layers were washed with brine (75 mL), dried over anhydrous Na$_2$SO$_4$, filtered and concentrated under reduced pressure to give a residue. The residue was purified by column chromatography (10% EA in PE) to give 7-3 (500 mg, 908 μmol, 63%) as a white solid.

To a solution of 7-3 in DMF (8 mL) was added imidazole (99 mg, 1.5 mmol) and TBSCl (219 mg, 1.5 mmol). The mixture was stirred at 20° C. for 3 h. The reaction was quenched with sat. aq. NaHCO$_3$ (30 mL) at 20° C. The mixture was extracted with EtOAc (2×30 mL). The combined organic layers were washed with brine (50 mL), dried over anhydrous Na$_2$SO$_4$, filtered and concentrated under reduced pressure to give a residue. The residue was purified by column chromatography (10% EA in PE) to give 7-4 (370 mg, 556 μmol, 77%) as a white solid.

To a solution of 7-4 (370 mg, 557 μmol) in MeCN (2.6 mL) was added DMAP (170 mg, 1.4 mmol), TEA (141 mg, 1.4 mmol) and TPSCl (410 mg, 1.4 mmol). The mixture was stirred at 20° C. for 2 h. NH$_3$.H$_2$O (2.3 mL) was added, and the mixture was stirred at 20° C. for 1 h. The reaction was quenched with sat. aq. NaHCO$_3$ (20 mL) at 20° C. The mixture was diluted with H$_2$O (10 mL) and extracted with EtOAc (2×20 mL). The combined organic layers were washed with brine (30 mL), dried over anhydrous Na$_2$SO$_4$, filtered and concentrated under reduced pressure to give a residue. The residue was purified by column chromatography (10% CH$_3$OH in DCM) to give 7-5 (300 mg, 452 μmol, 81%) as a white solid.

Compound 7-5 was dissolved in HCOOH (80%), and the mixture was stirred at 12° C. for 20 h. The mixture was concentrated under reduced pressure. The residue was purified by prep-HPLC (0.1% NH$_4$HCO$_3$ in water and MeCN) to give 7 (71 mg, 45%) as a white solid. MS (ESI): m/z: 278 [M+H]$^+$.

Example 8

Preparation of Compound 8

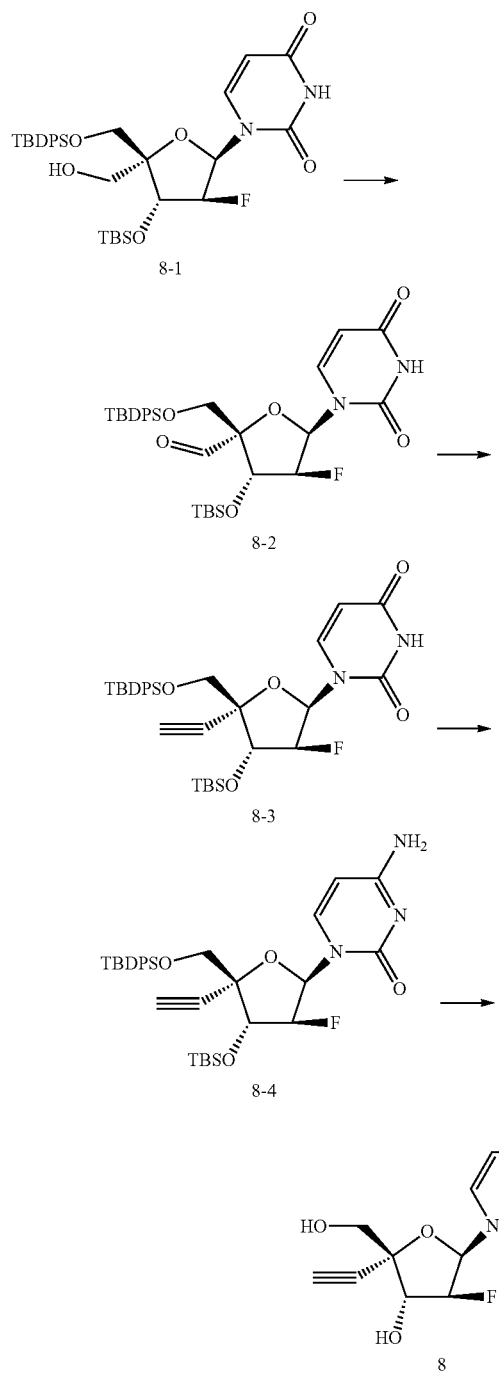

To a solution of 8-1 (1.5 g, 2.4 mmol) in DCM (12 mL) was added Dess-Martin (1.5 g, 3.6 mmol) at 0° C. The mixture was stirred at 20° C. for 1.5 h. The reaction was quenched with sat. aq. NaHCO$_3$:sat. aq. NaS$_2$O$_3$ (30 mL:30 mL) at 20° C. The mixture was extracted with EtOAc (2×50 mL). The combined organic layers were washed with brine (80 mL), dried over Na$_2$SO$_4$, filtered and concentrated under reduced pressure to give crude 8-2 (1.50 g), which was used for the next step without further purification.

To a solution of K$_2$CO$_3$ (1.7 g, 12.0 mmol) and TsN$_3$ (943 mg, 4.9 mmol) in MeCN (10 mL) was added CH$_3$COCH$_2$PO(OMe)$_2$ (793 mg, 4.9 mmol). The mixture was stirred at 20° C. for 2 h. A solution of 8-2 (1.5 g, 2.4 mmol) in CH$_3$OH (10 mL) was added, and the mixture was stirred at 20° C. for 12 h. The reaction was quenched with H$_2$O (70 mL) at 20° C. The mixture was extracted with EtOAc (2×70 mL). The combined organic layers were washed with brine (100 mL), dried over anhydrous Na$_2$SO$_4$, filtered and concentrated under reduced pressure to give a residue. The residue was purified by column chromatography (15% EA in PE) to give 8-3 (1.1 g, 1.8 mmol, 73%) as a white solid.

To a solution of 8-3 (500 mg, 802 µmol) in MeCN (4 mL) was added TEA (203 mg, 2.0 mmol), DMAP (245 mg, 2.0 mmol) and TPSCl (592 mg, 2.0 mmol). The mixture was stirred at 20° C. for 12 h. NH$_3$.H$_2$O (3 mL) was added, and the mixture was stirred at 20° C. for 2 h. The reaction was quenched with sat. aq. NaHCO$_3$ (30 mL) at 20° C. The mixture was extracted with EtOAc (2×30 mL). The combined organic layers were washed with brine (50 mL), dried over Na$_2$SO$_4$, filtered and concentrated under reduced pressure to give a residue. The residue was purified by column chromatography (10% CH$_3$OH in DCM) to give 8-4 (450 mg, 90%) as a white solid.

To a solution of 8-4 (450 mg, 722 µmol) in CH$_3$OH (20 mL) was added NH$_4$F (535 mg, 14.5 mmol). The mixture was stirred at 80° C. for 12 h. The mixture was concentrated under reduced pressure. The residue was purified by prep-HPLC (0.1% NH$_4$HCO$_3$ in water and MeCN) to give 8 (65 mg, 241 µmol, 33%) as a white solid. MS (ESI): m/z: 270 [M+H]$^+$.

Example 9

Preparation of Compound 9

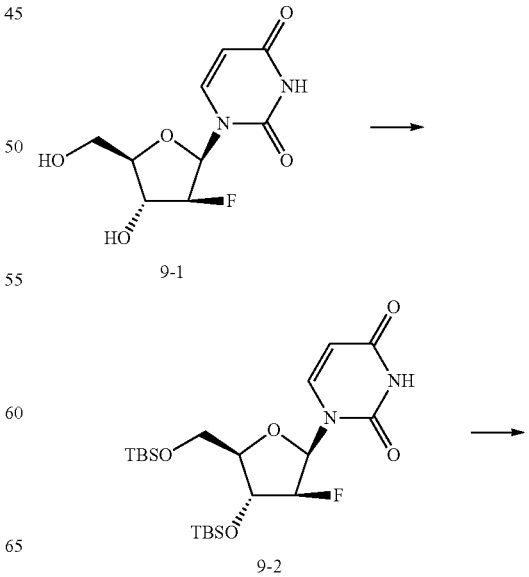

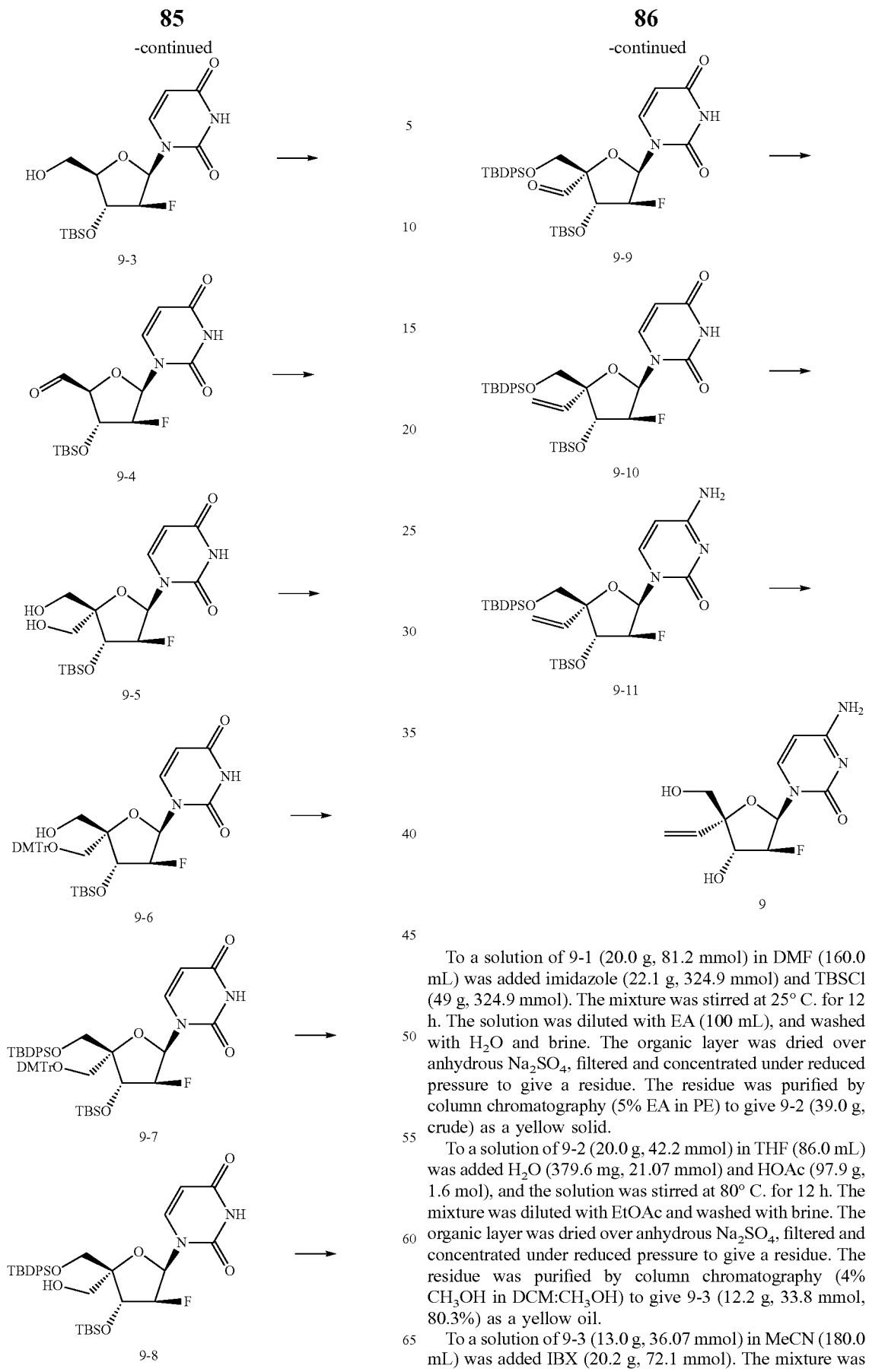

To a solution of 9-1 (20.0 g, 81.2 mmol) in DMF (160.0 mL) was added imidazole (22.1 g, 324.9 mmol) and TBSCl (49 g, 324.9 mmol). The mixture was stirred at 25° C. for 12 h. The solution was diluted with EA (100 mL), and washed with H$_2$O and brine. The organic layer was dried over anhydrous Na$_2$SO$_4$, filtered and concentrated under reduced pressure to give a residue. The residue was purified by column chromatography (5% EA in PE) to give 9-2 (39.0 g, crude) as a yellow solid.

To a solution of 9-2 (20.0 g, 42.2 mmol) in THF (86.0 mL) was added H$_2$O (379.6 mg, 21.07 mmol) and HOAc (97.9 g, 1.6 mol), and the solution was stirred at 80° C. for 12 h. The mixture was diluted with EtOAc and washed with brine. The organic layer was dried over anhydrous Na$_2$SO$_4$, filtered and concentrated under reduced pressure to give a residue. The residue was purified by column chromatography (4% CH$_3$OH in DCM:CH$_3$OH) to give 9-3 (12.2 g, 33.8 mmol, 80.3%) as a yellow oil.

To a solution of 9-3 (13.0 g, 36.07 mmol) in MeCN (180.0 mL) was added IBX (20.2 g, 72.1 mmol). The mixture was stirred at 80° C. for 1 h. The precipitate was filtered-off, and the filtrate was concentrated to give the crude product. The crude product was used for the next step directly without purification to give 9-4 (13.0 g, crude).

To a solution of 9-4 (13.0 g, 36.3 mmol) in 1,4-dioxane (140.0 mL) was added HCHO (11.8 g, 145.1 mmol) and NaOH (2 M, 27.2 mL). The mixture was stirred at 25° C. for 2 h and then neutralized with AcOH to pH=7. The mixture was treated with EtOH (90.0 mL) and NaBH$_4$ (8.2 g, 217.6 mmol), and then stirred at 25° C. for 1 h. The reaction was quenched with sat. NH$_4$Cl solution at 0° C., and then diluted with EtOAc. The combined organic layers were washed with brine, dried over anhydrous Na$_2$SO$_4$, filtered and concentrated under reduced pressure to give a residue. The residue was purified by column chromatography (4% CH$_3$OH in DCM) to give 9-5 (7.9 g, 20.2 mmol, 55.8%) as a white solid.

To a solution of 9-5 (7.0 g, 17.9 mmol) in pyridine (11.0 mL) was added DCM (45.0 mL) and DMTrCl (7.3 g, 21.5 mmol). The mixture was stirred at 0° C. for 40 mins. The reaction was quenched with CH$_3$OH (50 mL) at 0° C. The mixture was concentrated under reduced pressure to give a residue. The residue was purified by column chromatography (50% EA in PE) to give 9-6 (8.0 g, 64.4%) as a white solid.

To a solution of 9-6 (9.0 g, 13.0 mmol) in DCM (150.0 mL) was added imidazole (3.5 g, 51.9 mmol), AgNO$_3$ (6.6 g, 38.9 mmol) and TBDPSCl (27.0 g, 38.9 mmol). The mixture was stirred at 25° C. for 4 h. The mixture was filtered, and the filtrate was washed with brine, dried over anhydrous MgSO$_4$ and concentrated at low pressure. The residue was purified by column chromatography (33% EA in PE) to give 9-7 (10.1 g, 83.5%) as a white solid.

To a solution of 9-7 (12.0 g, 12.9 mmol) in DCM (40.0 mL) was added TFA (1.5 g, 12.9 mmol) and Et$_3$SiH (5.8 g, 50.2 mmol). The mixture was stirred at 25° C. for 30 mins. The reaction was quenched with sat. aq. NaHCO$_3$ at 25° C., and then diluted with DCM. The combined organic layers were washed with brine, dried over Na$_2$SO$_4$, filtered and concentrated under reduced pressure. The residue was purified to give 9-8 (7.5 g, 92.5%) as a white solid.

To a solution of 9-8 (1.1 g, 1.7 mmol) in DCM (8.0 mL) was added Dess-Martin (1.5 g, 3.5 mmol). The mixture was stirred at 0° C. for 1 h. The reaction was quenched with sat. aq. Na$_2$S$_2$O$_3$ and sat. aq. NaHCO$_3$ at 25° C., and then extracted with EtOAc (3×40 mL). The combined organic layers were washed with brine, dried over anhydrous Na$_2$SO$_4$, filtered and concentrated under reduced pressure to give a residue. Compound 9-9 (1.1 g, crude) was used for the next step without further purification.

To a solution of PPh$_3$Br (2.5 g, 7.1 mmol) in THF (5.0 mL) was added n-BuLi (2.5 M, 2.8 mL) at −78° C. under N$_2$. The mixture was stirred at 0° C. for 30 mins. A solution of 9-9 (1.1 g, 1.8 mmol) in THF (5.0 mL) was added dropwise at 0° C. under N$_2$. The mixture was stirred at 25° C. for 1 h. The reaction was quenched with sat. aq. NH$_4$Cl at 25° C., and then diluted with EtOAc. The combined organic layers were washed with brine, dried over anhydrous Na$_2$SO$_4$, filtered and concentrated under reduced pressure to give a residue. The residue was purified by column chromatography (20% EA in PE) to give 9-10 (700 mg, 63.3%) as a white solid.

To a solution of 9-10 (350 mg, 0.56 mmol) in MeCN (3.0 mL) was added TPSCl (363 mg, 1.2 mmol), Et$_3$N (124 mg, 1.2 mmol) and DMAP (150.5 mg, 1.2 mmol). The mixture was stirred at 25° C. for 3 h. The mixture was treated with NH$_3$.H$_2$O (9.1 g, 259.6 mmol) at 25° C., and then stirred for 2 h. The reaction was quenched with sat. aq. NH$_4$Cl at 25° C., and then diluted with EtOAc. The combined organic layers were washed with brine, dried over anhydrous Na$_2$SO$_4$, filtered and concentrated under reduced pressure to give a residue. The residue was purified by column chromatography (20% EA in PE) to give 9-11 (270.0 mg, 77.3%) as a white solid.

To a solution of 9-11 (270 mg, 0.4 mmol) in CH$_3$OH (10.0 mL) was added NH$_4$F (320 mg, 8.6 mmol). The mixture was stirred at 80° C. for 10 h. The reaction mixture was filtered, and the filtrate was concentrated under reduced pressure. The residue was purified by prep-HPLC (neutral condition) to give 9 (54 mg, 46.0%) as a white solid. MS (ESI): m/z: 272.1 [M+H]$^+$.

Example 10

Preparation of Compound 10

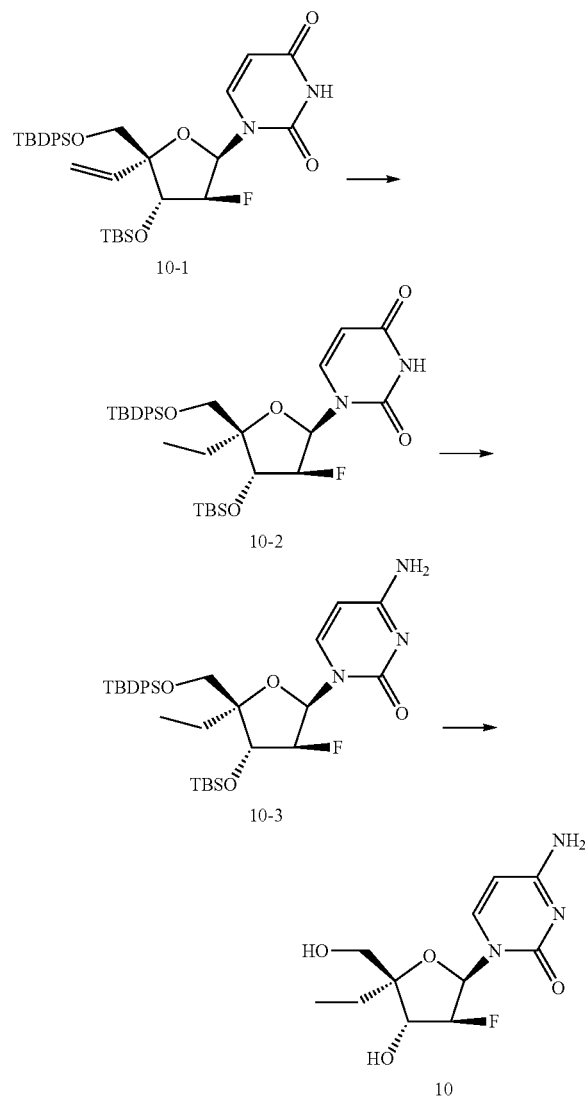

To a solution of 10-1 (350 mg, 0.56 mmol) in CH$_3$OH (10.0 mL) was added Pd/C (0.1 g) under N$_2$. The suspension was degassed and purged with H$_2$ (3×). The mixture was stirred under H$_2$ at 25° C. for 2 h. The mixture was filtered, and the filtrate was concentrated under reduced pressure. The crude product was used for next step directly without purification. Compound 10-2 (340 mg, 96.8%) was obtained as a white solid.

To a solution of 10-2 (340 mg, 0.54 mmol) in MeCN (5.0 mL) was added TPSCl (361 mg, 1.2 mmol), DMAP (146 mg, 1.2 mmol) and Et$_3$N (121 mg, 1.2 mmol). The mixture was stirred at 25° C. for 3 h. The mixture was treated with NH$_3$.H$_2$O (4.5 g, 129.8 mmol) at 25° C., and then stirred for 2 h. The reaction was quenched with sat. aq. NH$_4$Cl at 25° C. The mixture was diluted with EtOAc. The combined organic layers were washed with brine, dried over anhydrous Na$_2$SO$_4$, filtered and concentrated under reduced pressure. The residue was purified by column chromatography (20% EA in PE) to give 10-3 (270 mg, 79.5%) as a white solid.

To a solution of 10-3 (270 mg, 0.43 mmol) in CH$_3$OH (10.0 mL) was added NH$_4$F (319 mg, 8.6 mmol). The mixture was stirred at 80° C. for 10 h, and then concentrated under reduced pressure. The residue was purified by prep-HPLC (neutral condition) to give 10 (78 mg, 66.2%) as a white solid. MS (ESI): m/z: 274.1 [M+H]$^+$.

Example 11

Preparation of Compound 11

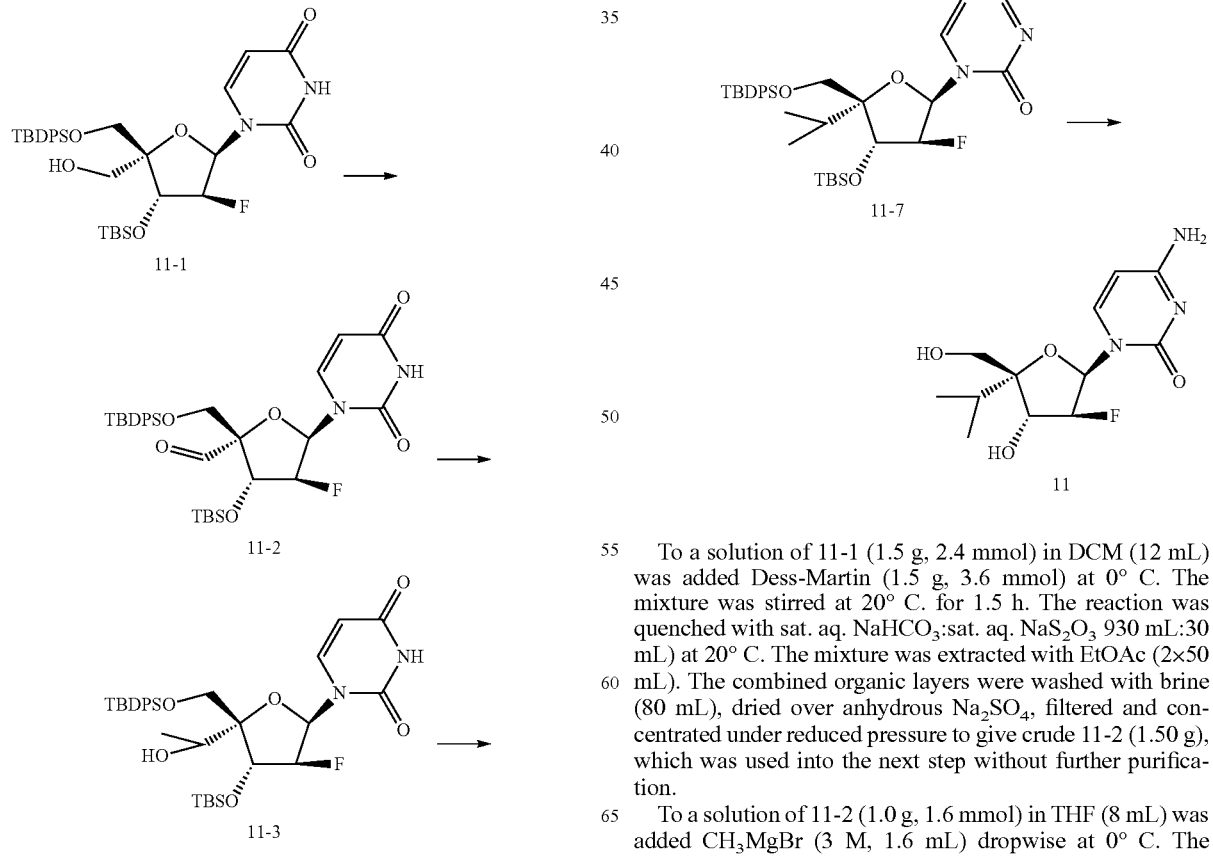

To a solution of 11-1 (1.5 g, 2.4 mmol) in DCM (12 mL) was added Dess-Martin (1.5 g, 3.6 mmol) at 0° C. The mixture was stirred at 20° C. for 1.5 h. The reaction was quenched with sat. aq. NaHCO$_3$:sat. aq. NaS$_2$O$_3$ 930 mL:30 mL) at 20° C. The mixture was extracted with EtOAc (2×50 mL). The combined organic layers were washed with brine (80 mL), dried over anhydrous Na$_2$SO$_4$, filtered and concentrated under reduced pressure to give crude 11-2 (1.50 g), which was used into the next step without further purification.

To a solution of 11-2 (1.0 g, 1.6 mmol) in THF (8 mL) was added CH$_3$MgBr (3 M, 1.6 mL) dropwise at 0° C. The mixture was stirred at 0° C. for 0.5 h. The reaction was quenched with sat. aq. NH₄Cl at 0° C. The mixture was extracted with EtOAc (2×70 mL). The combined organic layers were washed with brine (100 mL), dried over anhydrous Na₂SO₄, filtered and concentrated under reduced pressure. The residue was purified by column chromatography (15% EA in PE) to give 11-3 (900 mg, 88%) as a white solid.

To a solution of 11-3 (900 mg, 1.4 mmol) in DCM (10 mL) was added Dess-Martin (1.1 g, 2.8 mmol). The mixture was stirred at 20° C. for 2 h. The reaction was quenched with sat. aq. Na₂S₂O₃:sat. aq. NaHCO₃ (30 mL:30 mL) at 20° C. The mixture was extracted with EtOAc (2×40 mL). The combined organic layers were washed with brine (70 mL), dried over anhydrous Na₂SO₄, filtered and concentrated under reduced pressure to give crude 11-4 (850.00 mg), which was used for the next step without further purification.

To a solution of Methyl-triphenyl-phosphonium bromide (3.4 g, 9.4 mmol) in THF (2.7 mL) was added t-BuOK (1 M, 9.3 mL) dropwise at 0° C. The mixture was stirred at 20° C. for 1 h. A solution of 11-4 (850 mg, 1.3 mmol) in THF (3 mL) was added at 20° C. The mixture was stirred at 20° C. for 12 h. The reaction was quenched with sat. aq. NH₄Cl (35 mL) at 20° C. The mixture was extracted with EtOAc (2×30 mL). The combined organic layers were washed with brine (70 mL), dried over anhydrous Na₂SO₄, filtered and concentrated under reduced pressure. The residue was purified by column chromatography (20% EA in PE) to give 11-5 (650 mg, 76%) as a white solid.

A mixture of 11-5 (500 mg, 782 μmol) and Pd/C (270 mg) in EtOAc (20 mL) was degassed and purged with H₂ (3×), and then the mixture was stirred at 20° C. for 2 h under H₂. The mixture was filtrated under reduced pressure. The filtrate was concentrated under reduced pressure to give crude 11-6 (500.00 mg), which was used into the next step without further purification.

To a solution of 11-6 (500 mg, 780 μmol) in MeCN (7 mL) was added TEA (197 mg, 1.9 mmol), DMAP (238 mg, 1.9 mmol) and TPSCl (575 mg, 1.9 mmol) at 20° C. The mixture was stirred at 20° C. for 12 h. NH₃.H₂O (7 mL) was added, and the mixture was stirred at 20° C. for 1 h. The reaction was quenched with sat. aq. NaHCO₃ (30 mL) at 20° C. The mixture was extracted with EtOAc (2×30 mL). The combined organic layers were washed with brine (50 mL), dried over anhydrous Na₂SO₄, filtered and concentrated under reduced pressure. The residue was purified by column chromatography (20% CH₃OH in DCM) to give 11-7 (400 mg, 80%) as a white solid.

To a solution of 11-7 (400 mg, 625 μmol) in CH₃OH (10 mL) was added NH₄F (695 mg, 18.8 mmol) at 80° C. The mixture was stirred at 80° C. for 12 h. The mixture was filtrated and concentrated under reduced pressure. The residue was purified by prep-HPLC (0.1% NH₄HCO₃ in water and MeCN) to give 11 (55 mg, 191 μmol, 21%) as a white solid. MS (ESI): m/z: 288 [M+H]⁺.

Example 12

Preparation of Compound 12

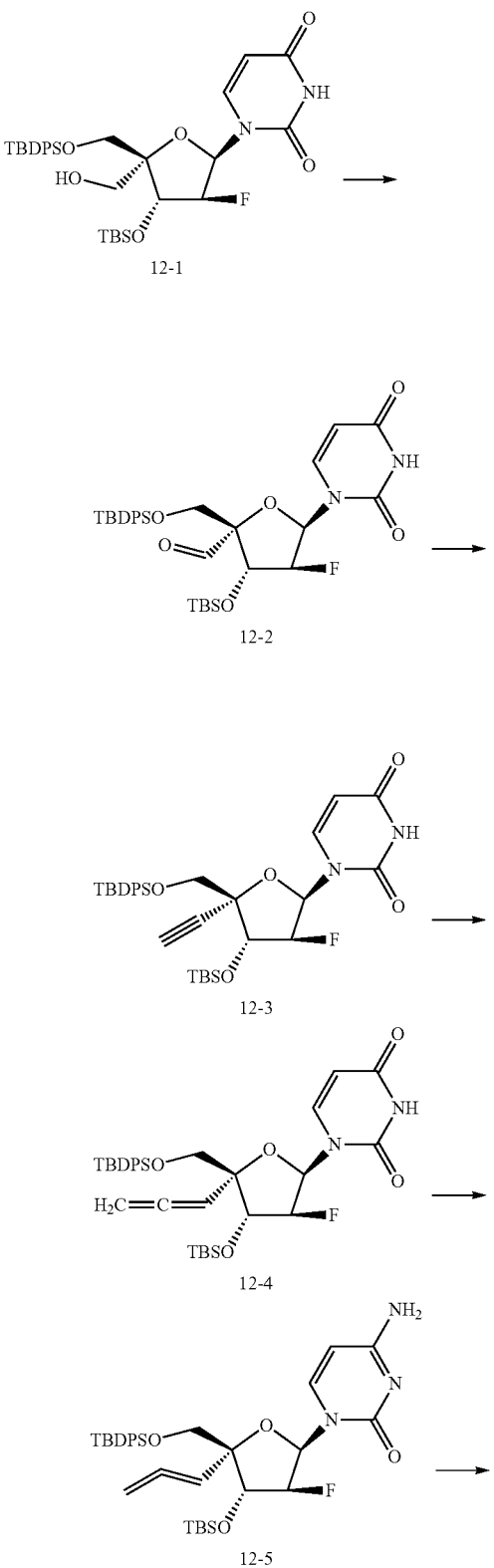

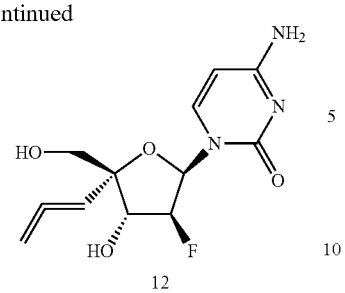

To a solution of 12-1 (1.5 g, 2.4 mmol) in DCM (12 mL) was added Dess-Martin (1.5 g, 3.6 mmol) at 0° C. The mixture was stirred at 20° C. for 1.5 h. The reaction was quenched with sat. aq. NaHCO$_3$:sat. aq. NaS$_2$O$_3$ (30 mL:30 mL) at 20° C. The mixture was extracted with EtOAc (2×50 mL). The combined organic layers were washed with brine (80 mL), dried over anhydrous Na$_2$SO$_4$, filtered and concentrated under reduced pressure to give crude 12-2 (1.50 g), which was used for the next step without further purification.

To a solution of K$_2$CO$_3$ (1.7 g, 12.0 mmol) and TsN$_3$ (943 mg, 4.9 mmol) in MeCN (10 mL) was added CH$_3$COCH$_2$PO (OMe)$_2$ (793 mg, 4.9 mmol). The mixture was stirred at 20° C. for 2 h. A solution of 12-2 (1.5 g, 2.4 mmol) in CH$_3$OH (10 mL) was added, and the mixture was stirred at 20° C. for 12 h. The reaction was quenched with H$_2$O (70 mL) at 20° C. The mixture was extracted with EtOAc (70 mL). The combined organic layers were washed with brine (100 mL), dried over anhydrous Na$_2$SO$_4$, filtered and concentrated under reduced pressure. The residue was purified by column chromatography (15% EA in PE) to give 12-3 (1.1 g, 73%) as a white solid.

To a solution of 12-3 (500 mg, 802 μmol) in dioxane (4 mL) was added CuBr (57 mg, 401 μmol), (CH$_2$O)$_n$ (48 mg, 1.6 mmol) and diisopropylamine (203 mg, 2.0 mmol). The mixture was stirred at 140° C. for 2.5 h. The reaction was quenched with sat. aq. NH$_4$Cl (30 mL) at 15° C. The mixture was extracted with EtOAc (2×30 mL). The combined organic layers were washed with brine (50 mL), dried over anhydride Na$_2$SO$_4$, filtered and concentrated under reduced pressure. The residue was purified by column chromatography (15% EA in PE) to give 12-4 (350 mg, 68%) as a yellow solid.

To a solution of 12-4 (350 mg, 549 μmol) in MeCN (3 mL) was added TEA (139 mg, 1.4 mmol), DMAP (167 mg, 1.4 mmol) and TPSCl (405 mg, 1.4 mmol). The mixture was stirred at 15° C. for 2 h. NH$_3$.H$_2$O (3 mL) was added, and the mixture was stirred at 15° C. for 1 h. The reaction was quenched with sat. aq. NaHCO$_3$ (20 mL) at 15° C. The mixture was extracted with EtOAc (2×20 mL). The combined organic layers were washed with brine (30 mL), dried over anhydride Na$_2$SO$_4$, filtered and concentrated under reduced pressure. The residue was purified by column chromatography (15% CH$_3$OH in DCM) to give 12-5 (200 mg, 57%) as a white solid.

To a solution of 12-5 (200 mg, 316 μmol) in CH$_3$OH (15 mL) was added NH$_4$F (350 mg, 9.5 mmol) at 80° C. The mixture was stirred at 80° C. for 12 h. The mixture was filtrated and concentrated under reduced pressure. The residue was purified by prep-HPLC (0.1% NH$_4$HCO$_3$ in water and MeCN) to give 12 (40 mg, 44%) as a white solid. MS (ESI): m/z: 284 [M+H]$^+$.

Example 13

Preparation of Compound 37

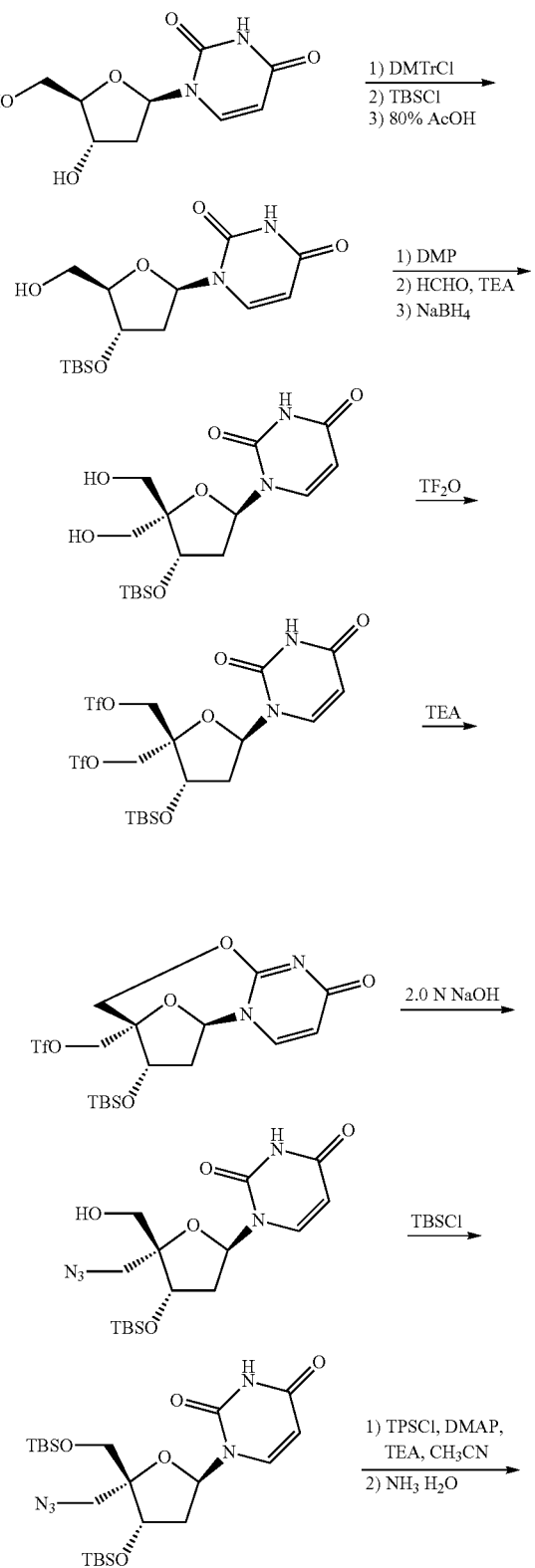

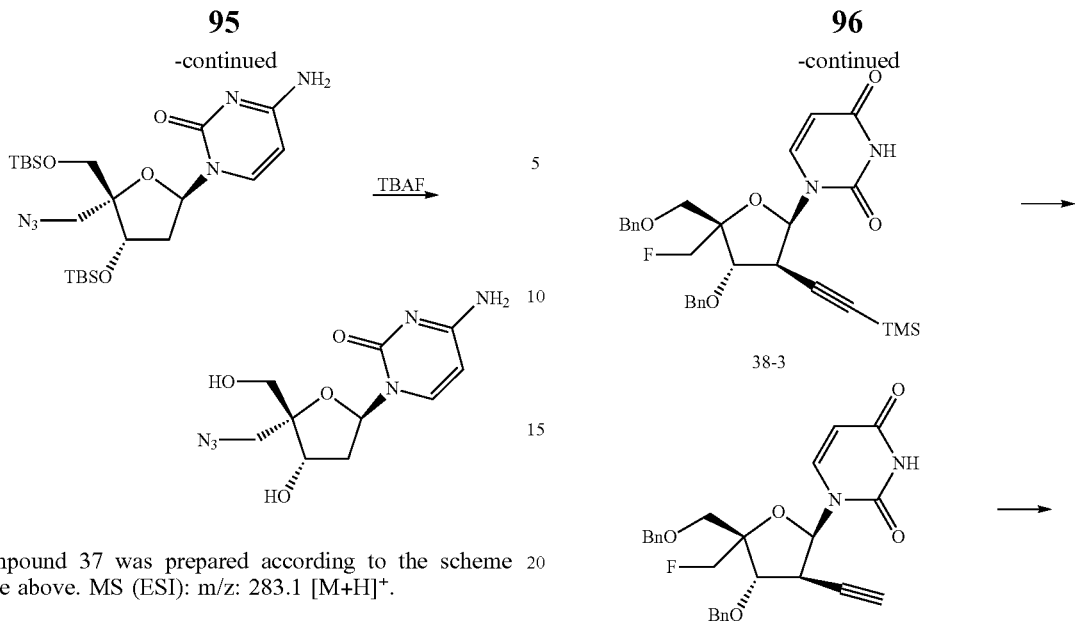

Compound 37 was prepared according to the scheme provide above. MS (ESI): m/z: 283.1 [M+H]⁺.

Example 14

Preparation of Compounds 38 and 39

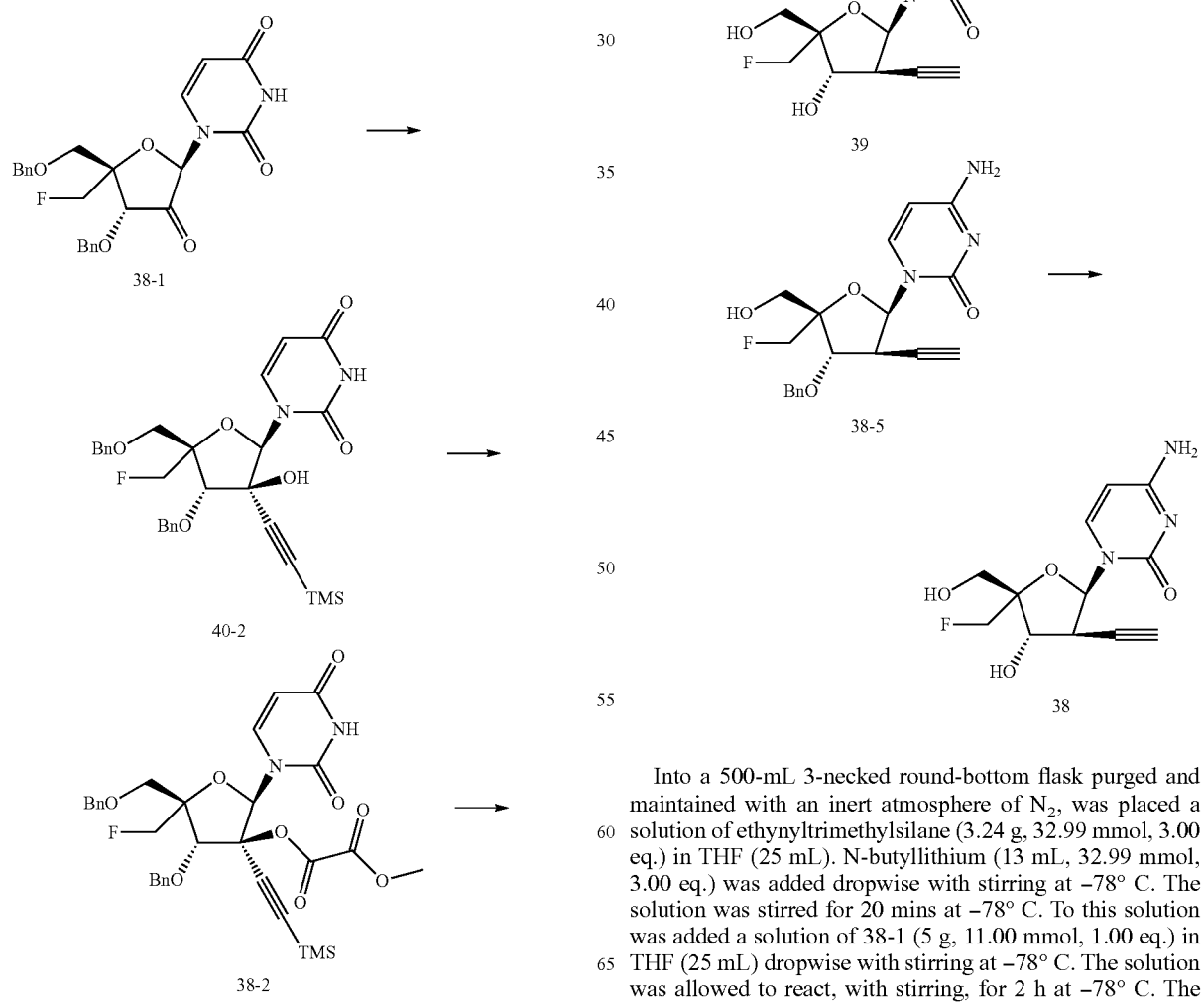

Into a 500-mL 3-necked round-bottom flask purged and maintained with an inert atmosphere of N₂, was placed a solution of ethynyltrimethylsilane (3.24 g, 32.99 mmol, 3.00 eq.) in THF (25 mL). N-butyllithium (13 mL, 32.99 mmol, 3.00 eq.) was added dropwise with stirring at −78° C. The solution was stirred for 20 mins at −78° C. To this solution was added a solution of 38-1 (5 g, 11.00 mmol, 1.00 eq.) in THF (25 mL) dropwise with stirring at −78° C. The solution was allowed to react, with stirring, for 2 h at −78° C. The reaction was quenched by adding sat. NH₄Cl, extracted with EA. The organic layers were combined, dried over anhydrous sodium sulfate, filtered, and concentrated under reduced pressure. The residue was applied onto a silica gel column with EA/PE (1:5-1:2) to give 40-2 (2.5 g, 41%) as a yellow solid. MS (ESI): m/z: 553 [M+H]$^+$.

Into a 100-mL round-bottom flask purged and maintained with an inert atmosphere of $N_2$, was placed a solution of 40-2 (400 mg, 0.72 mmol, 1.00 eq.) in $CH_2Cl_2$ (5 mL). 4-dimethylaminopyridine (176.8 mg, 1.45 mmol, 1.99 eq.) was added at RT. Methyl 2-chloro-2-oxoacetate (132.6 mg, 1.08 mmol, and 1.49 eq.) was then added at RT. The solution was stirred for 1 h at RT, and then diluted with $CH_2Cl_2$. The solution was washed with water, dried over anhydrous sodium sulfate, filtered and concentrated under reduced pressure. The residue was applied onto a silica gel column with $CH_2Cl_2/CH_3OH$ (50:1-30:1) to give 38-2 (200 mg, 43%) as a white solid. MS (ESI): m/z: 639 [M+H]$^+$.

Into a 250-mL round-bottom flask purged and maintained with an inert atmosphere of $N_2$, was placed a solution of 38-2 (4.2 g, 6.58 mmol, 1.00 eq.) in toluene (50 mL). 2, 2'-azobisisobutyronitrile (2.16 g, 13.15 mmol, 2.02 eq.) and tributyl-3-stannyl (38.2 g, 131.70 mmol, 20.04 eq.) were added at RT. The solution was stirred for 1 h at 110° C., and then concentrated under reduced pressure. The residue was applied onto a silica gel column with $CH_2Cl_2/CH_3OH$ (100:1-50:1) to give 38-3 (2.7 g, 77%) as a yellow solid. MS (ESI): m/z: 537 [M+H]$^+$.

Into a 250-mL round-bottom flask purged and maintained with an inert atmosphere of $N_2$, was placed a solution of 38-3 (2.7 g, 5.03 mmol, 1.00 eq.) in $CH_3OH$ (30 mL). Potassium carbonate (1.39 g, 9.98 mmol, 1.99 eq.) was added at RT. The solution was stirred for 1 h at RT, and the solids were filtered off. The solution was concentrated under reduced pressure. The residue was applied onto a silica gel column with EA/PE (1:10-1:1) to give 38-4 (1.0 g, 43%) as a white solid. MS (ESI): m/z: 465 [M+H]$^+$.

Into a 25-mL round-bottom flask purged and maintained with an inert atmosphere of $N_2$, was placed a solution of 38-4 (200 mg, 0.43 mmol, 1.00 eq.) in $CH_2Cl_2$ (1 mL). Trichloroborane (0.12 mL, 5.00 eq.) was added dropwise with stirring at −78° C. The solution was stirred for 1 h at RT. The reaction was quenched by the addition of $CH_2Cl_2$ (0.5 mL). The mixture was concentrated under reduced pressure. The crude product (200 mg) was purified by prep-HPLC (Column, X Bridge C18, 19*150 mm, 5 um; mobile phase, A: Water/0.05% TFA, Mobile Phase B: ACN; Flow rate: 20 mL/min; Gradient: 30% B to 70% B in 10 min; Detector, 254 nm) to give 39 (48.8 mg, 40%) as a white solid. MS (ESI): m/z: 285 [M+H]$^+$.

Into a 25-mL round-bottom flask purged and maintained with an inert atmosphere of $N_2$, was placed a solution of 38-4 (300 mg, 0.65 mmol, 1.00 eq.) in MeCN (5 mL). 4-dimethylaminopyridine (157 mg, 1.29 mmol, 1.99 eq.) and triethylamine (196 mg, 1.94 mmol, 3.00 eq.) were added at RT. 2,4,6-triisopropylbenzenesulfonyl chloride (587 mg, 1.94 mmol, 3.00 eq.) was then added at RT. The solution was stirred for 1 h at RT. Ammonium hydroxide (3 mL, 28%) as added at RT, and then stirred for 1 h at RT. The mixture was concentrated under reduced pressure. The residue was applied onto a silica gel column with $CH_2Cl_2/CH_3OH$ (100:1-20:1) to give 38-5 (205 mg, 68%) as a yellow solid. MS (ESI): m/z: 464 [M+H]$^+$.

Into a 25-mL round-bottom flask purged and maintained with an inert atmosphere of $N_2$, was placed a solution of 38-5 (200 mg, 0.43 mmol, 1.00 eq.) in $CH_2Cl_2$ (2 mL). Trichloroborane (0.12 mL, 5.00 eq.) was dropwise with stirring at −78° C. The solution was stirred for 1 h at RT. The reaction was quenched with $CH_3OH$. The mixture was concentrated under reduced pressure. The crude product (200 mg) was purified by prep-HPLC (Column, X Bridge C18, 19*250 mm, 5 um; mobile phase, A: Water/10 mM $NH_4HCO_3$, Mobile Phase B: ACN; Flow rate: 30 mL/min; Gradient: 3% B to 9.5% B in 6.5 min; Detector) to give 38 (40.4 mg, 33%) as a white solid. MS (ESI): m/z: 284 [M+H]$^+$.

Example 15

Preparation of Compounds 40 and 41

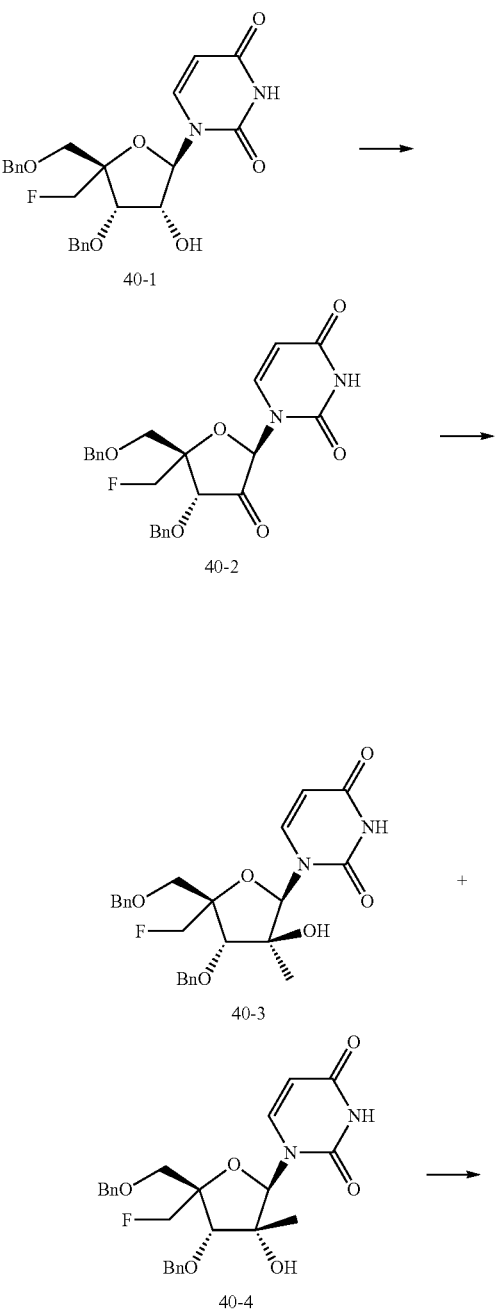

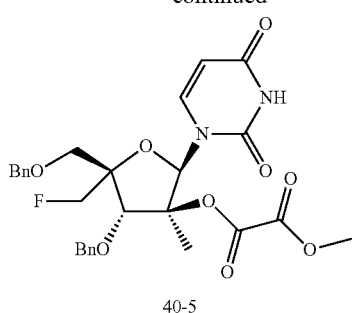

40-5

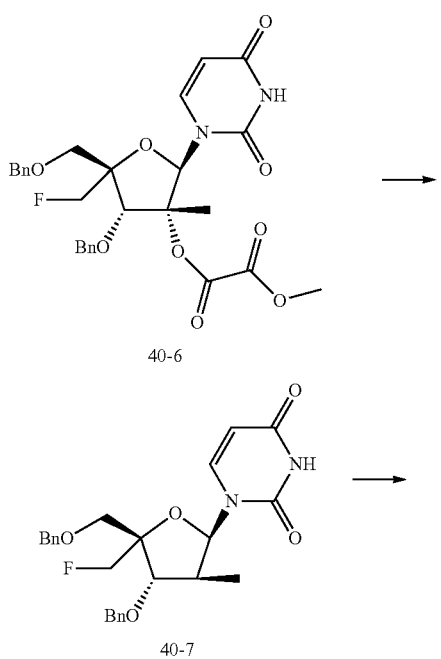

40-6

40-7

40-7 →

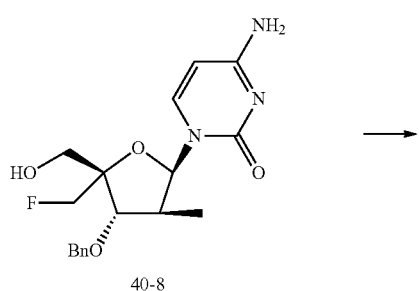

40-8

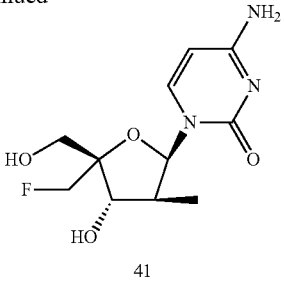

41

Into a 250-mL round-bottom flask purged and maintained with an inert atmosphere of N$_2$, was placed a solution of 40-1 (13 g, 28.48 mmol, 1.00 eq. 40-1 was prepared as provided in Kitano et al., *Tetrahedron* (1997) 53(39):13315-13322) in MeCN (130 mL). 2-iodoxybenzoic acid (16 g, 57.14 mmol, 2.00 eq.) was added at RT, and then stirred for 2 h at 80° C. The mixture was cooled, and the solid was filtered off. The solution was concentrated under reduced pressure to give 40-2 (11 g, 85%) as a yellow solid. MS (ESI): m/z: 455 [M+H]$^+$.

Into a 100-mL 3-necked round-bottom flask purged and maintained with an inert atmosphere of Ar, was placed a solution of 40-2 (1.8 g, 3.96 mmol, 1.00 eq.) in THF (20 mL). Methylmagnesium bromide (1M in THF, 25 mL, 5.00 eq.) was added dropwise with stirring at −78° C. The solution was then stirred at −30° C. for 4 h. The reaction was quenched by adding aq. NH$_4$Cl (50 mL). The solution was extracted with EA (2×50 mL). The organic layers were combined, washed with aq. NaCl (1×25 mL), dried over anhydrous sodium sulfate, filtered and concentrated under reduced pressure. The residue was applied onto a silica gel column with PE/EA (1:1) to give 40-3 and 40-4 (1.2 g, 64%, mixture, ratio 1:1) as a white solid. MS (ESI): m/z: 471 [M+H]$^+$.

Into a 50-mL round-bottom flask purged and maintained with an inert atmosphere of Ar, was placed a solution of 40-3 and 40-4 (mixture, ratio 1:1, 1.2 g, 2.55 mmol, 1.00 eq.) in MeCN (20 mL). 4-dimethylaminopyridine (930 mg, 7.61 mmol, 3.00 eq.) was added. Methyl 2-chloro-2-oxoacetate (635 mg, 5.18 mmol, 2.00 eq.) was then added dropwise with stirring at RT. The solution was then stirred for 1 h at RT. The solution was diluted with EA (50 mL), and the solution was then washed with aq. sodium bicarbonate (1×25 mL) and NaCl (1×25 mL). The solution was dried over anhydrous sodium sulfate, filtered and concentrated under reduced pressure to give 40-5 and 40-6 (1.2 g, 85%, mixture, ratio 1:1) as a yellow solid. MS (ESI): m/z: 557 [M+H]$^+$.

Into a 100-mL round-bottom flask purged and maintained with an inert atmosphere of Ar, was placed a solution of 40-5 and 40-6 (mixture, ratio 1:1, 1.2 g, 2.16 mmol, 1.00 eq.) in toluene (12 mL). Tri-n-butyl-tin hydride (12.1 g, 41.72 mmol, 20.00 eq.) was added followed by 2,2'-azobisisobutyronitrile (708 mg, 4.31 mmol, 2.00 eq.). The solution was stirred for 1 h at 110° C., and then concentrated under reduced pressure. The residue was applied onto a silica gel column with CH$_2$Cl$_2$/CH$_3$OH (50:1). The crude product (1.2 g) was purified by flash-HPLC (Column, XB-C18, 250*50 mm, 10 um; mobile phase, A: Water/10 mmol/L trifluoroacetic acid, Mobile Phase B: acetonitrile; Gradient: 5% B to 40% B in 45 min; Detector, 254 nm) to 40-7 (600 mg, 61%) as a white solid. MS (ESI): m/z: 455 [M+H]$^+$.

Into a 10-mL round-bottom flask purged and maintained with an inert atmosphere of Ar, was placed a solution of 40-7 (500 mg, 1.10 mmol, 1.00 eq.) in CH₂Cl₂ (5 mL). Trichloroborane (1M in CH₂Cl₂, 5 mL) was added at −78° C. The solution was stirred at −30° C. for 1 h. The reaction was quenched with CH₃OH (2 mL). The solution was concentrated under reduced pressure. The crude product (250 mg) was purified by prep-HPLC (Column, X Bridge C18, 19*150 mm, 5 um; mobile phase, A: Water/10 mmol/L ammonium bicarbonate, Mobile Phase B: acetonitrile; Gradient: 5% B to 15% B in 15 min; Detector, 254 nm) to give 40 (76 mg, 25%) as a white solid. MS (ESI): m/z: 275 [M+H]⁺.

Into a 100-mL round-bottom flask purged and maintained with an inert atmosphere of Ar, was placed a solution of 40-7 (1 g, 2.20 mmol, 1.00 eq.) in MeCN (20 mL). 4-dimethylaminopyridine (270 mg, 2.21 mmol, 1.00 eq.), triethylamine (670 mg, 6.62 mmol, 3.00 eq.) and 2,4,6-triisopropylbenzenesulfonyl chloride (2 g, 3.00 eq.) were added, and the solution was stirred for 2 h at RT. NH₄OH hydroxide (20 mL, 28%) was added. The resulting solution was allowed to react with stirring for an additional 2 h at 25° C. The solution was diluted with EA (50 mL), washed with water (1×25 mL) and aq. NaCl (1×25 mL), dried over anhydrous sodium sulfate, filtered and concentrated under reduced pressure. The residue was applied onto a silica gel column with CH₂Cl₂/CH₃OH (50:1) to give 40-8 (600 mg, 60%) as a white solid. MS (ESI): m/z: 454 [M+H]⁺.

Into a 50-mL round-bottom flask purged and maintained with an inert atmosphere of Ar, was placed a solution of 40-8 (450 mg, 0.99 mmol, 1.00 eq.) in CH₂Cl₂ (5 mL). Trichloroborane (1M in CH₂Cl₂, 4.5 mL) was added dropwise with stirring at −78° C. The solution was then stirred at −30° C. for 1 h. The reaction was quenched with CH₃OH (1 mL), and then concentrated under reduced pressure. The crude product (150 mg) was purified by prep-HPLC (Column, X Bridge C18, 19*150 mm, 5 um; mobile phase, A: Water/10 mmol/L ammonium bicarbonate, Mobile Phase B: acetonitrile; Gradient: 5% B to 85% B in 10 min; Detector, 254 nm) to give 41 (73.5 mg, 27%) as a white solid. MS (ESI): m/z: 274 [M+H]⁺.

Example 16

Preparation of Compounds 42 and 43

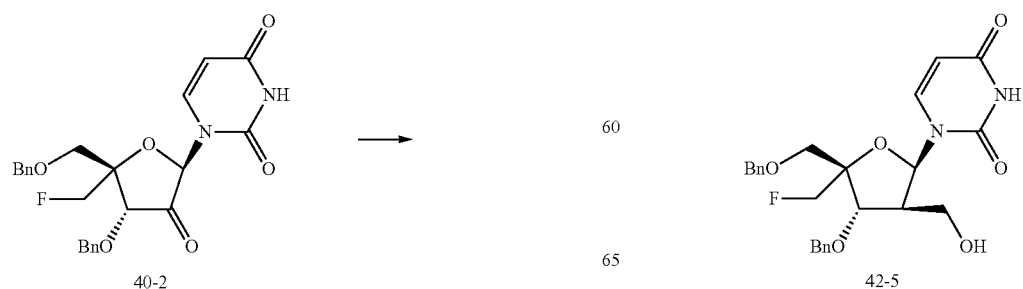

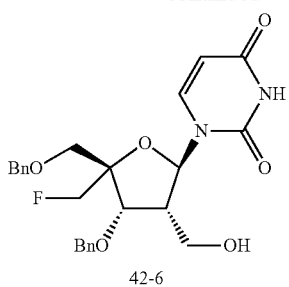

42-6

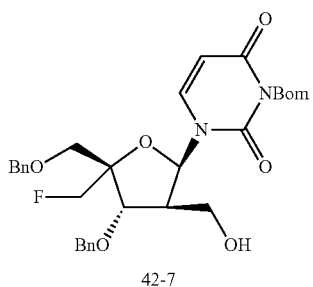

42-7

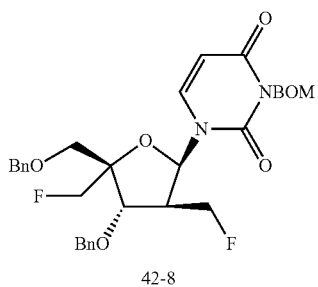

42-8

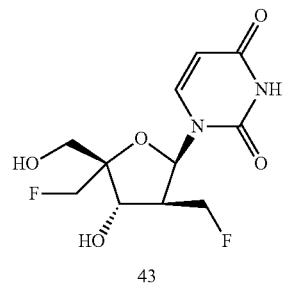

43

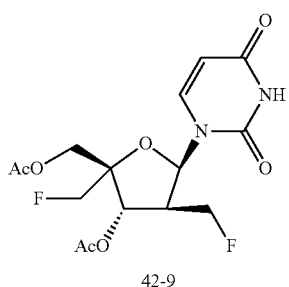

42-9

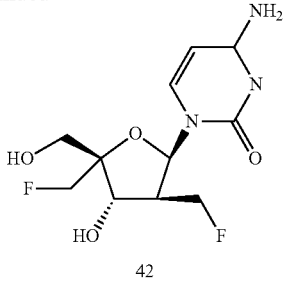

42

Into a 2000-mL 3-necked round-bottom flask purged and maintained with an inert atmosphere of $N_2$, was placed DMSO (600 mL), THF (20 mL) and trimethyloxosulfonium iodide (43.5 g, 197.66 mmol, 3.00 eq.). NaH (5.41 g, 225.42 mmol, 2.00 eq.) was added at 10° C. The solution was stirred for 1 h at RT. A solution of 40-2 (30 g, 66.01 mmol, 1.00 eq.) in THF (200 mL) was added dropwise with stirring at 0° C. The solution was allowed to react with stirring for 1 h at 0° C. The reaction was quenched with aq. $NH_4Cl$. The solution was extracted with EA (2×1000 mL). The organic layers were combined, washed with aq. NaCl (1×1000 mL), dried over anhydrous sodium sulfate, filtered and concentrated under reduced pressure. The residue was applied onto a silica gel column with $CH_2Cl_2/CH_3OH$ (30:1) to give 42-1 (21.8 g, 70%) as yellow oil. MS (ESI): m/z: 469 $[M+H]^+$.

Into a 1000-mL round-bottom flask purged and maintained with an inert atmosphere of $N_2$, was placed a solution of 42-1 (21.8 g, 46.53 mmol, 1.00 eq.) in acetic acid (300 mL). Sodium acetate (35 g, 426.65 mmol, 2.00 eq.) was added at RT. The solution was stirred for 3 h at 120° C., and then concentrated under reduced pressure. The residue was diluted with $CH_2Cl_2$ (1000 mL), washed with aq. sodium bicarbonate (1×500 mL) and aq. NaCl (1×500 mL), dried over anhydrous sodium sulfate, filtered and concentrated under reduced pressure. The residue was applied onto a silica gel column with $CH_2Cl_2/CH_3OH$ (20:1) to give 42-2 (14.8 g, 60%) as a yellow solid. MS (ESI): m/z: 529 $[M+H]^+$.

Into a 500-mL round-bottom flask purged and maintained with an inert atmosphere of $N_2$, was placed a solution of 42-2 (20 g, 37.84 mmol, 1.00 eq.) in $CH_3OH$ (200 mL). Sodium methylate (30% in $CH_3OH$, 4 mL) was added. The solution was stirred for 4 h at RT. The reaction was quenched with acetic acid. The mixture was concentrated under reduced pressure. The residue was applied onto a silica gel column with $CH_2Cl_2/CH_3OH$ (20:1) to give 42-3 (17.2 g, 93%) as a yellow solid. MS (ESI): m/z: 487 $[M+H]^+$.

Into a 500-mL 3-necked round-bottom flask purged and maintained with an inert atmosphere of Ar, was placed a solution of 42-3 (17 g, 34.94 mmol, 1.00 eq.) in MeCN (200 mL). 1,1'-thiocarbonyldiimidazole (10.45 g, 58.64 mmol, 3.00 eq.) was added. The solution was stirred for 3 h at 40° C., and then concentrated under reduced pressure. The residue was applied onto a silica gel column with PE/EA (1:1) to give 42-4 (13 g, 70%) as a white solid. MS (ESI): m/z: 529 $[M+H]^+$.

Into a 500-mL round-bottom flask purged and maintained with an inert atmosphere of Ar, was placed a solution of 42-4 (13 g, 24.60 mmol, 1.00 eq.) in toluene (130 mL). 2,2'-azobisisobutyronitrile (8 g, 48.72 mmol, 2.00 eq.) and tributyl-3-stannyl (143 g, 493.02 mmol, 20.00 eq.) were added. The solution was stirred for 3 h at 110° C., and then concentrated under reduced pressure. The residue was applied onto a silica gel column with CH$_2$Cl$_2$/CH$_3$OH (20:1) to give 42-5 (8 g, 69%) and 42-6 (1 g, 8.6%) as a white solid. MS (ESI): m/z: 471 [M+H]$^+$.

Into a 500-mL 3-necked round-bottom flask purged and maintained with an inert atmosphere of Ar, was placed a solution of 42-5 (7.8 g, 16.58 mmol, 1.00 eq.) and 1,8-diazabicyclo[5.4.0]undec-7-ene (5 g, 32.84 mmol, 2.00 eq.) in THF (80 mL). Benzyl chloromethyl ether (3.9 g, 24.90 mmol, 1.50 eq.) was added dropwise with stirring at 0° C. The solution was stirred for 2 h at 0° C. The reaction was quenched with CH$_3$OH, and then concentrated under reduced pressure. The residue was diluted with CH$_2$Cl$_2$ (500 mL), washed with water (1×100 mL) and aq. NaCl (1×100 mL), dried over anhydrous sodium sulfate, filtered and concentrated under reduced pressure. The residue was applied onto a silica gel column with CH$_2$Cl$_2$/CH$_3$OH (20:1) to give 42-7 (8.4 g, 86%) as yellow oil. MS (ESI): m/z: 591 [M+H]$^+$.

Into a 100-mL round-bottom flask purged and maintained with an inert atmosphere of Ar, was placed a solution of 42-7 (4 g, 6.77 mmol, 1.00 eq.) in toluene (40 mL). Diethylaminosulfur trifluoride (3.8 g, 23.57 mmol, 2.00 eq.) was added dropwise with stirring at 0° C. The solution was stirred for 4 h at 60° C. The reaction was quenched with chilled aq. sodium bicarbonate. The solution was extracted with EA (2×100 mL). The organic layers were combined, washed with aq. NaCl (1×50 mL), dried over anhydrous sodium sulfate, filtered and concentrated under reduced pressure. The residue was applied onto a silica gel column with PE/EA (1:1) to give 42-8 (1.2 g, 30%) as yellow oil. MS (ESI): m/z: 593 [M+H]$^+$.

Into a 25-mL round-bottom flask purged and maintained with an inert atmosphere of Ar, was placed a solution of 42-8 (500 mg, 0.84 mmol, 1.00 eq.) in CH$_2$Cl$_2$ (5 mL). Boron trichloride (1 M in CH$_2$Cl$_2$, 5 mL) was added dropwise with stirring at −78° C. The solution was then stirred for 3 h at −78° C.--30° C. The reaction was quenched with CH$_3$OH. The mixture was concentrated under reduced pressure. The crude product (220 mg) was purified by prep-HPLC (Column, X Bridge C18, 19*150 mm, 5 um; mobile phase, A: Water/10 mmol/L ammonium bicarbonate, Mobile Phase B: acetonitrile; Gradient: 5% B to 15% B in 15 min; Detector, 254 nm) to give 43 (42.2 mg, 17%) as a white solid. MS (ESI): m/z: 293 [M+H]$^+$.

Into a 100-mL round-bottom flask purged and maintained with an inert atmosphere of Ar, was placed a solution of 43 (500 mg, 1.71 mmol, 1.00 eq.) in pyridine (5 mL). Acetyl acetate (2 mL) was added, and the solution was stirred for 2 h at RT. The solution was concentrated under reduced pressure. The residue was diluted with CH$_2$Cl$_2$ (100 mL), washed with water (1×50 mL) and aq. NaCl (1×50 mL), dried over anhydrous sodium sulfate, filtered and concentrated under reduced pressure. The residue was applied onto a silica gel column with EA/PE (1:1) to give 42-9 (500 mg, 78%) as a white solid. MS (ESI): m/z: 377 [M+H]$^+$.

Into a 25-mL round-bottom flask purged and maintained with an inert atmosphere of Ar, was placed a solution of 42-9 (500 mg, 1.00 eq.), 4-dimethylaminopyridine (162 mg, 1.33 mmol, 1.00 eq.) and triethylamine (482 mg, 4.76 mmol, 3.00 eq.) in MeCN (5 mL). 2,4,6-triisopropylbenzenesulfonyl chloride (1.2 g, 3.96 mmol, 3.00 eq.) was added, and the solution stirred for 2 h at RT. NH$_4$OH (5 mL, 28%) was added, and the solution was stirred for 2 h at RT. The mixture was concentrated under reduced pressure. The crude product (200 mg) was purified by prep-HPLC (Column, X Bridge C18, 19*150 mm, 5 um; mobile phase, A: Water/10 mmol/L ammonium hydroxide, Mobile Phase B: acetonitrile; Gradient: 5% B to 10% B in 15 min; Detector, 254 nm) to give 42 (63.2 mg, 16%) as a white solid. MS (ESI): m/z: 292 [M+H]$^+$.

Example 17

Preparation of Compound 44

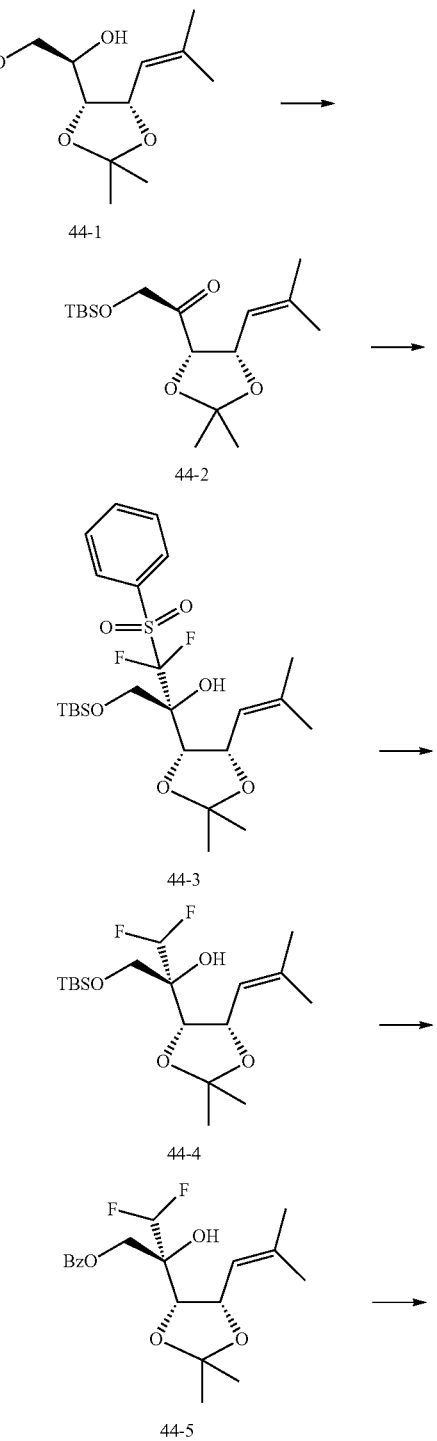

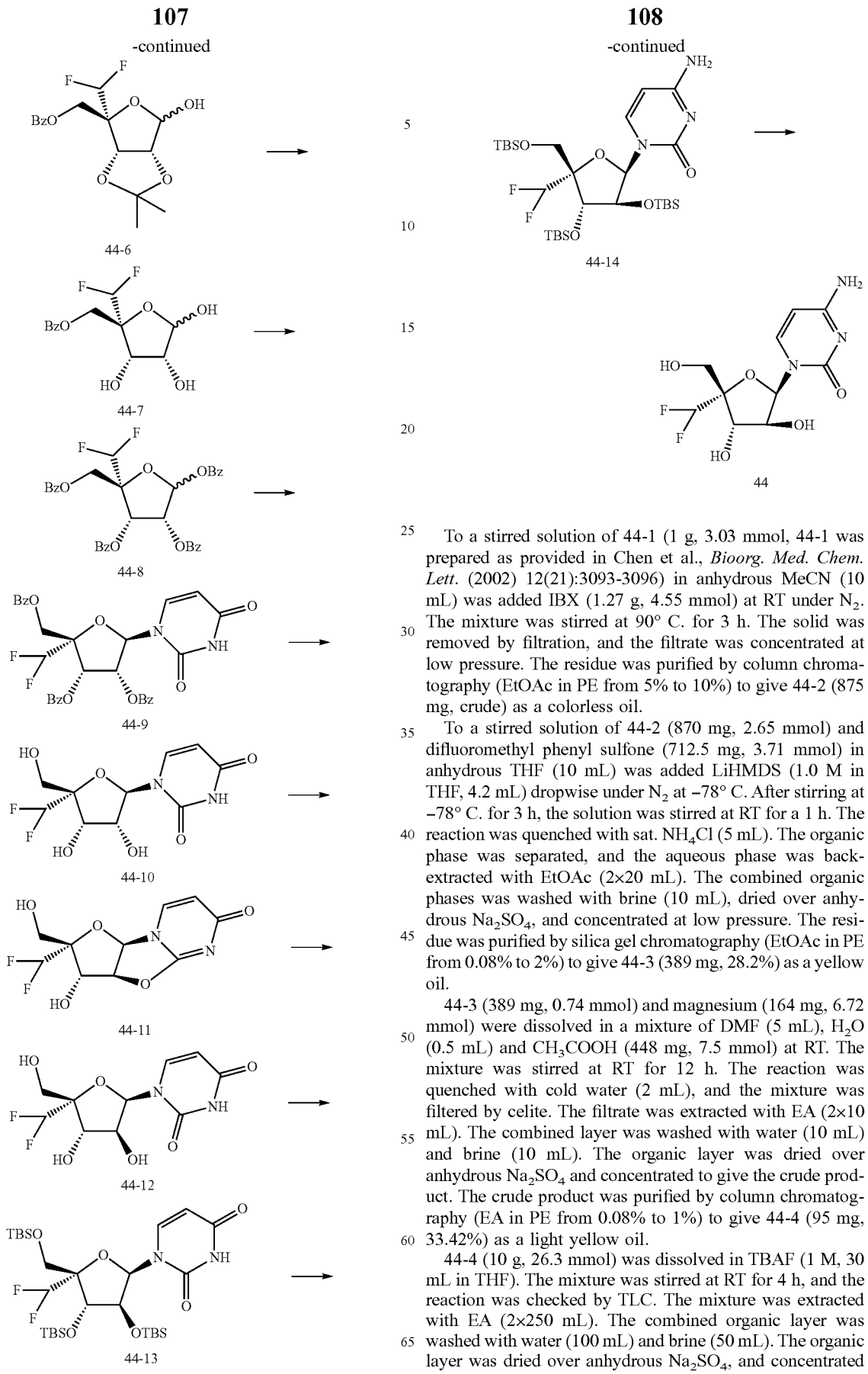

To a stirred solution of 44-1 (1 g, 3.03 mmol, 44-1 was prepared as provided in Chen et al., *Bioorg. Med. Chem. Lett.* (2002) 12(21):3093-3096) in anhydrous MeCN (10 mL) was added IBX (1.27 g, 4.55 mmol) at RT under $N_2$. The mixture was stirred at 90° C. for 3 h. The solid was removed by filtration, and the filtrate was concentrated at low pressure. The residue was purified by column chromatography (EtOAc in PE from 5% to 10%) to give 44-2 (875 mg, crude) as a colorless oil.

To a stirred solution of 44-2 (870 mg, 2.65 mmol) and difluoromethyl phenyl sulfone (712.5 mg, 3.71 mmol) in anhydrous THF (10 mL) was added LiHMDS (1.0 M in THF, 4.2 mL) dropwise under $N_2$ at −78° C. After stirring at −78° C. for 3 h, the solution was stirred at RT for a 1 h. The reaction was quenched with sat. $NH_4Cl$ (5 mL). The organic phase was separated, and the aqueous phase was back-extracted with EtOAc (2×20 mL). The combined organic phases was washed with brine (10 mL), dried over anhydrous $Na_2SO_4$, and concentrated at low pressure. The residue was purified by silica gel chromatography (EtOAc in PE from 0.08% to 2%) to give 44-3 (389 mg, 28.2%) as a yellow oil.

44-3 (389 mg, 0.74 mmol) and magnesium (164 mg, 6.72 mmol) were dissolved in a mixture of DMF (5 mL), $H_2O$ (0.5 mL) and $CH_3COOH$ (448 mg, 7.5 mmol) at RT. The mixture was stirred at RT for 12 h. The reaction was quenched with cold water (2 mL), and the mixture was filtered by celite. The filtrate was extracted with EA (2×10 mL). The combined layer was washed with water (10 mL) and brine (10 mL). The organic layer was dried over anhydrous $Na_2SO_4$ and concentrated to give the crude product. The crude product was purified by column chromatography (EA in PE from 0.08% to 1%) to give 44-4 (95 mg, 33.42%) as a light yellow oil.

44-4 (10 g, 26.3 mmol) was dissolved in TBAF (1 M, 30 mL in THF). The mixture was stirred at RT for 4 h, and the reaction was checked by TLC. The mixture was extracted with EA (2×250 mL). The combined organic layer was washed with water (100 mL) and brine (50 mL). The organic layer was dried over anhydrous $Na_2SO_4$, and concentrated under reduced pressure. The crude product was purified by silica gel column chromatography (PE in EA from 2.5% to 10%) to give the crude product (5.1 g, 75.3%) as a yellow oil.

To a solution of the crude product (5 g, 18.78 mmol) in dry DCM (50 mL) was added TEA (5.7 g, 56.34 mmol), DMAP (46 mg, 0.375 mmol) and BzCl (5.28 g, 37.6 mmol) at 0° C. The mixture was stirred at 0° C. for 1 h and then at 25° C. for 2 h. The reaction was quenched with $H_2O$ (10 mL) at 0° C., and the mixture was extracted with $CH_2Cl_2$ (2×50 mL). The combined organic layers were washed with brine (2×50 mL), dried over anhydrous $Na_2SO_4$, filtered and concentrated under reduced pressure. The residue was purified by silica gel column chromatography (EtOAc in PE from 2% to 5%) to give 44-5 (5.1 g, 73.3%) as a yellow oil.

A stirred solution of 44-5 (5.1 g, 13.77 mmol) in anhydrous DCM (80 mL) was bubbled with $O_3$ (15 psi) at −78° C. for 10 mins until the mixture turned blue. The mixture was then bubbled with $O_2$ until the solution turned colorless. The organic layer was evaporated to give crude 44-6 (4.66 g, crude) as a yellow oil.

To a stirred solution of 44-6 (4.6 g, 13.36 mmol) in DCM (50 mL) was added 90% TFA solution (25 mL) at 0° C., and the mixture was then warmed to RT. The mixture was stirred for 12 h, and the reaction was checked by TLC. After the reaction was completed, the mixture was co-evaporated with toluene (3×) to give crude 44-7 (4 g crude) as a solid.

To a solution of 44-7 (4 g, 13.15 mmol) in anhydrous DCM (60 mL) was added TEA (6.15 g, 65.7 mmol, 9.1 mL), DMAP (8.03 g, 65.75 mmol) and BzCl (9.24 g, 65.7 mmol) at 0° C. The mixture was stirred at RT for 12 h, and then the reaction was quenched with $CH_3OH$ (10 mL) and water (30 mL) at RT. The mixture was extracted with DCM (2×50 mL). The combined organic layers were washed with sat. $NH_4Cl$ (3×30 mL) and brine, dried over $Na_2SO_4$, filtered and concentrated under reduced pressure. The residue was purified by silica gel column chromatography (EtOAc in PE from 2% to 5%) to give 44-8 (4.6 g, 56.7%) as a solid.

A stirred suspension of uracil (0.4 g, 3.57 mmol) and $(NH_4)_2SO_4$ (5 mg) in HMDS (6 mL, 28.55 mmol) was heated to 120° C. for 2 h. After the solid was dissolved, the mixture was cooled to RT and concentrated to give a residue (840 mg, 91.9%). The residue was dissolved in anhydrous MeCN (10 mL), and the solution was treated with 44-8 (1.0 g, 1.6 mmol) and TMSOTf (3.6 g, 16.2 mmol) at RT. The mixture was stirred at 90° C. for 12 h. The reaction was quenched with sat. $NaHCO_3$ (10 mL) and extracted with EtOAc (2×25 mL). The organic layer was dried over anhydrous $Na_2SO_4$ and filtered. The filtrate was evaporated at low pressure. The residue was purified by column chromatography (EtOAc in PE from 10% to 25%) to give 44-9 (0.83 g, 84.6%) as a solid.

44-9 (1 g, 1.65 mmol) was treated with $NH_3/CH_3OH$ (20 mL, 7 M) at RT. The mixture was stirred at RT for 12 h, and then concentrated at low pressure. The residue was purified by column chromatography ($CH_3OH$ in DCM from 2% to 5%) to give 44-10 (395 mg, 81.2%) as a white solid.

To a stirred solution of 44-10 (800 mg, 2.72 mmol) in anhydrous DMF (12 mL) was added diphenyl carbonate (640 mg, 3 mmol) and $NaHCO_3$ (57 mg, 680 mol) at RT under $N_2$. The mixture was stirred at 140° C. under microwave for 1 h. The solvent was removed under reduced pressure. The residue was purified by column chromatography ($CH_3OH$ in DCM from 1% to 10%) to give 44-11 (540 mg, 72%) as a brown solid.

44-11 (540 mg, 1.96 mmol) was treated with a mixture of HCl-dioxane (15 mL, 4 M) and $H_2O$ (15 mL). The mixture was stirred at 80° C. for 2 h. The solvent was removed under reduced pressure. The residue was purified by column chromatography ($CH_3OH$ in DCM from 1% to 10%) to give 44-12 (545 mg, 94.5%) as a yellow solid.

To a solution of 44-12 (545 mg, 1.85 mmol) in DMF (11 mL) was added imidazole (3.27 g, 48.15 mmol), $AgNO_3$ (3.46 g, 20.3 mmol) and TBSCl (3.3 g, 22.2 mmol) at RT under $N_2$. The mixture was stirred at 100° C. for 6 h. The mixture was cooled to RT, and then diluted with EA (50 mL). The mixture was filtered with celite. The filtrate was diluted with EA (60 mL) and washed with water (2×40 mL). The organic layer was concentrated under reduced pressure. The residue was purified by silica gel chromatography (EA in PE from 3% to 20%) to give 44-13 (575 mg, 52.2%) as a white solid.

To a stirred solution of 44-13 (575 mg, 901 μmol) in anhydrous MeCN (8 mL) was added DMAP (220 mg, 1.80 mmol), TEA (182 mg, 1.80 mol) and TPSCl (416 mg, 1.37 mmol) at RT. The mixture was stirred at RT for 2 h. The mixture was treated with $NH_3.H_2O$ (10 mL), and then the mixture was stirred for 2 h. The mixture was concentrated under reduced pressure. The residue was dissolved in EA (30 mL). The solution was washed with brine (10 mL), dried over anhydrous $Na_2SO_4$, filtered and concentrated under reduced pressure. The residue was purified by column chromatography ($CH_3OH$ in DCM from 1% to 2%) to give 44-14 (514 mg, 78%) as a light yellow oil.

To a solution of 44-14 (514 mg, 807 μmol) in $CH_3OH$ (9 mL) was added $NH_4F$ (898 mg, 24.2 mmol) at RT under $N_2$. The mixture was stirred at 90° C. for 12 h. The mixture was cooled to RT, and the solid was filtered off. The filtrate was removed under reduced pressure. The residue was purified by silica gel chromatography ($CH_3OH$ in DCM from 5% to 20%) to give crude 44. Crude 44 was purified by prep-HPLC (neutral) to give purified 44 (175 mg, 74%) as a white solid. MS (ESI): m/z: 294 $[M+H]^+$ and 587 $[2M+H]^+$.

Example 18

Preparation of Compound 45

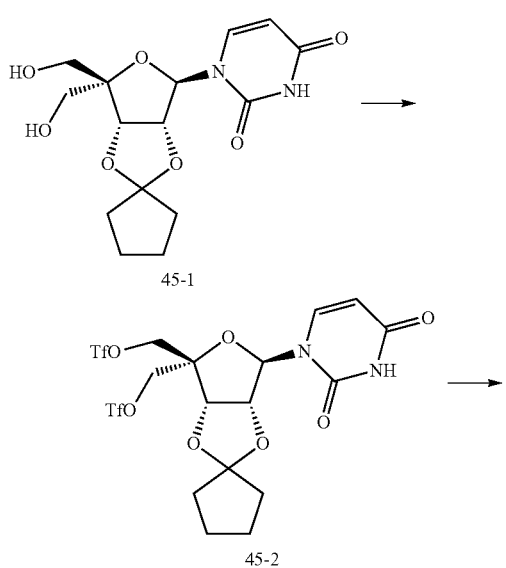

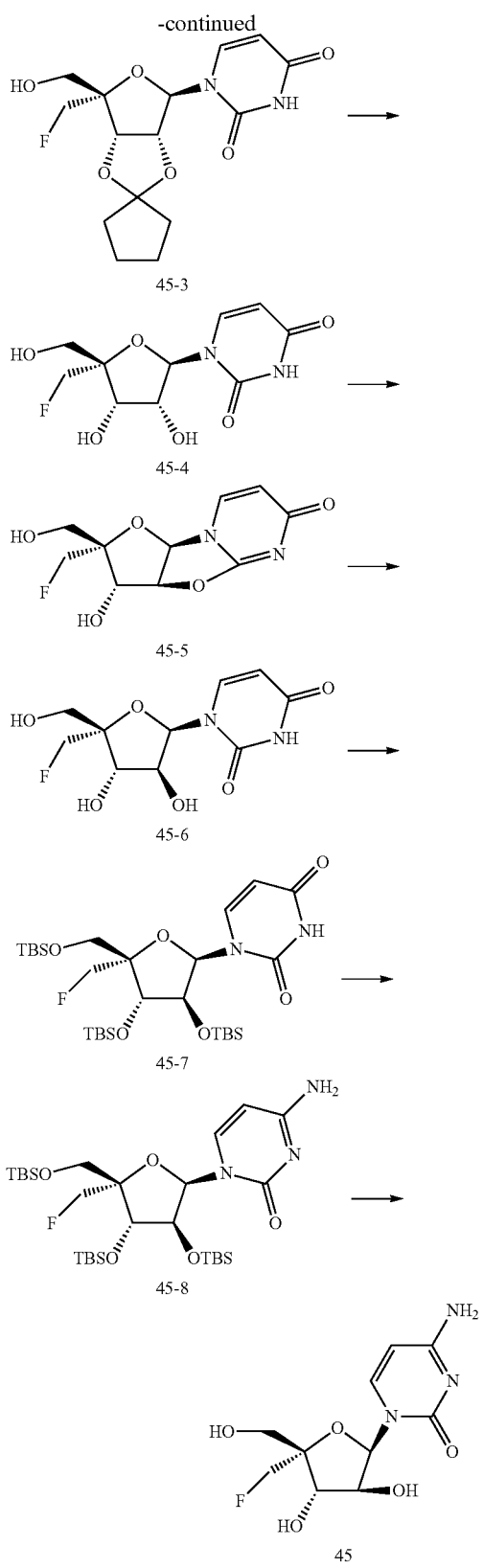

To a solution of 45-1 (5.0 g, 14.7 mmol, 45-1 was prepared as provided in Rolland de Ravel et al., *J. Med. Chem.* (2015) 58(4):1862-1878) in DCM (100.0 mL) was added pyridine (4.1 g, 51.4 mmol) and Tf$_2$O (9.1 g, 32.3 mmol) at 0° C. The mixture was stirred at 0° C. for 1 h. The reaction was quenched with H$_2$O (200 mL) at 15° C. The mixture was extracted with DCM (2×220.0 mL). The combined organic layers were washed with brine (400 mL), dried over anhydrous Na$_2$SO$_4$, filtered and concentrated under reduced pressure to give a residue. The residue was purified by column chromatography (20% EA in PE) to give 45-2 (4.9 g, 55%) as a yellow solid.

The 45-2 (4.9 g, 8.2 mmol) was dissolved in TBAF (1 M in THF, 81.1 mL), and the mixture was stirred at 15° C. for 30 h under N$_2$. The reaction was quenched with H$_2$O (100 mL) at 15° C. The mixture was extracted with EtOAc (3×100 mL). The combined organic layers were washed with brine (300 mL), dried over anhydrous Na$_2$SO$_4$, filtered and concentrated under reduced pressure. The residue was purified by column chromatography (10% CH$_3$OH in DCM) to give 45-3 (2.2 g, 79%) as a white solid.

45-3 (1.0 g, 2.9 mmol) was dissolved in HCOOH (80% in H$_2$O, 30.0 mL). The mixture was stirred at 15° C. for 12 h. The mixture was concentrated under reduced pressure. The residue was dissolved in CH$_3$OH (80 mL), and stirred for 30 mins. The mixture was concentrated under reduced pressure. The residue was purified by column chromatography (12% CH$_3$OH in DCM) to give 45-4 (600 mg, 74%) as a white solid.

To a solution of 45-4 (500 mg, 1.8 mmol) in DMF (6.0 mL) was added diphenyl carbonate (465 mg, 2.2 mmol) and NaHCO$_3$ (76 mg, 905 μmol). The mixture was stirred at 140° C. for 1.5 h. The mixture was concentrated under reduced pressure to remove the DMF. The residue was purified by column chromatography (12% CH$_3$OH in DCM) to give 45-5 (260 mg, 55%) as a white solid.

To a solution of 45-5 (500 mg, 1.9 mmol) in EtOH (9.0 mL) and H$_2$O (1.0 mL) was added NaOH (232 mg, 5.8 mmol). The mixture was stirred at 15° C. for 2 h. The mixture was concentrated under reduced pressure to remove EtOH and H$_2$O. The residue was purified by column chromatography (12% CH$_3$OH in DCM) to give 45-6 (450 mg, 83%) as a white solid.

To a solution of 45-6 (450 mg, 1.6 mmol) in DMF (1.0 mL) was added AgNO$_3$ (3.5 g, 19.7 mmol), imidazole (2.8 g, 40.7 mmol) and TBSCl (3.0 g, 19.7 mmol). The mixture was stirred at 100° C. for 5 h. The reaction was quenched with H$_2$O (30 mL) at 20° C. The mixture was extracted with EtOAc (2×30 mL). The combined organic layers were washed with brine (60 mL), dried over anhydrous Na$_2$SO$_4$, filtered and concentrated under reduced pressure. The residue was purified by column chromatography (30% EA in PE) to give 45-7 (550 mg, 54%) as a white solid.

To a solution of 45-7 (550 mg, 888 μmol) in MeCN (7.0 mL) was added TEA (224 mg, 2.2 mmol), DMAP (271 mg, 2.2 mmol) and TPSCl (670 mg, 2.22 mmol). The mixture was stirred at 20° C. for 12 h. The mixture was treated with NH$_3$.H$_2$O (3.5 mL, 28% purity), and then stirred at 20° C. for 1 h. The reaction was quenched with sat.NH$_4$Cl aq. (30 mL) at 15° C. The mixture was diluted with H$_2$O (30 mL) and extracted with EtOAc (2×30 mL). The combined organic layers were washed with brine (60 mL), dried over anhydrous Na$_2$SO$_4$, filtered and concentrated under reduced pressure. The residue was purified by column chromatography (10% CH$_3$OH in DCM) to give 45-8 (500 mg, 91%) as a white solid.

To a solution of 45-8 (200 mg, 324 μmol) in CH$_3$OH (10 mL) was added NH$_4$F (370 mg, 9.7 mmol). The mixture was stirred at 80° C. for 12 h. The solid was removed by filtration. The filtrate was concentrated under reduced pressure. The residue was purified by prep-HPLC (0.1%

NH$_4$HCO$_3$ in water and MeCN) to give 45 (35 mg, 40%) as a white solid. MS (ESI): m/z: 551.1 [2M+H]$^+$.

Example 19

Preparation of Compound 46

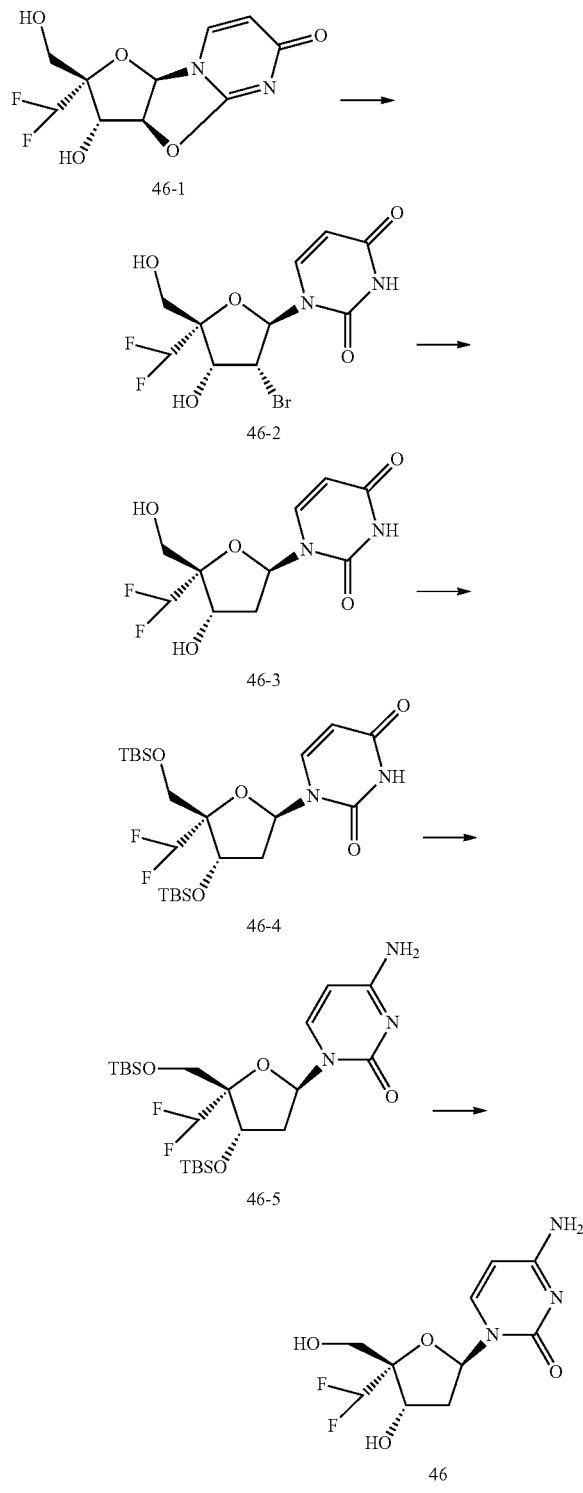

To a solution of 46-1 (600 mg, 2.17 mmol) in dioxane (20 mL) was added BF$_3$.Et$_2$O (338.79 mg, 2.39 mmol) and LiBr (245 mg, 2.82 mmol). The mixture was stirred at 60° C. for 2 h. The mixture was concentrated at low pressure, and the residue was purified by column chromatography (10% CH$_3$OH in DCM) to give 46-2 (720 mg, 93.09%) as a yellow solid.

To a solution of 46-2 (700 mg, 1.96 mmol) in EA (5 mL) and EtOH (5.00 mL) was added Pd/C (300 mg, 10% purity) and NaOAc (234.76 mg, 2.86 mmol) under N$_2$. The suspension was degassed under vacuum and purged with H$_2$ (3×). The mixture was stirred under a H$_2$ (15 psi) balloon at RT for 2 h. The solid was filtered off, and the filtrate was concentrated at low pressure. The residue was purified by column chromatography (5% CH$_3$OH in DCM) to give 46-3 (420 mg, 77.02%) as a white solid.

To a solution of 46-3 (400 mg, 1.44 mmol) in DMF (8 mL) was added imidazole (978.83 mg, 14.38 mmol) and AgNO$_3$ (488.47 mg, 2.88 mmol), followed by TBSCl (2.17 g, 14.38 mmol). The mixture was stirred at 80° C. for 2 h. The solid was filtered off, and the filtrate was concentrated at low pressure. The residue was dissolved in EA (20 mL). The solution was washed with brine and water (1:1, 20 mL). The organic layer was dried over anhydrous Na$_2$SO$_4$ and concentrated at low pressure. The residue was purified by column chromatography (EA:PA=2:1) to give 46-4 (610 mg, 83.60%) as a white solid.

To a solution of 46-4 (600 mg, 1.18 mmol) in MeCN (1.00 mL) was added 2,4,6-triisopropylbenzene-1-sulfonyl chloride (714.75 mg, 2.36 mmol), DMAP (288.32 mg, 2.36 mmol) and TEA (238.81 mg, 2.36 mmol). The mixture was stirred at RT for 2 h. The mixture was treated with NH$_3$.H$_2$O (2 mL, 28% purity), and stirred for 1 h. The mixture was diluted with EA (30 mL). The solution was washed with sat. NH$_4$Cl solution. The organic layer was dried over anhydrous Na$_2$SO$_4$ and concentrated at low pressure. The residue was purified by column chromatography (5% CH$_3$OH in DCM) to give 46-5 (420 mg, 70.38%) as a white solid.

To a solution of 46-5 (420 mg, 830.47 μmol) in CH$_3$OH (20 mL) was added NH$_4$F (153.80 mg, 4.15 mmol). The mixture was stirred at 80-100° C. for 24 h., and then cooled to RT. The solid was removed by filtration. The filtrate was concentrated at low pressure. The residue was purified by column chromatography (5% CH$_3$OH in DCM) to give the crude product. The crude product was purified by prep-HPLC (neutral system) to give purified 46 (81 mg, 35.18%) as a white solid. MS (ESI): m/z: 555.3 [2M+H]$^+$.

Example 20

Triphosphates

Dry nucleoside (0.05 mmol) was dissolved in the mixture of PO(OMe)$_3$ (0.7 mL) and pyridine (0.3 mL). The mixture was evaporated in vacuum for 15 mins at bath temperature (42° C.), than cooled down to RT. N-Methylimidazole (0.009 mL, 0.11 mmol) was added followed by POCl$_3$ (9 μL, 0.11 mmol), and the mixture was kept at RT for 20-40 mins. The reaction was controlled by LCMS and monitored by the appearance of corresponding nucleoside 5'-monophosphate. After completion, tetrabutylammonium salt of pyrophosphate (150 mg) was added, followed by DMF (0.5 mL) to get a homogeneous solution. After 1.5 h at ambient temperature, the reaction was diluted with water (10 mL) and loaded on the column HiLoad 16/10 with Q Sepharose High Performance. Separation was done in a linear gradient of NaCl from 0 to 1N in 50 mM TRIS-buffer (pH 7.5).

Triphosphate is eluted at 75-80% B. Corresponding fractions were concentrated. Desalting was achieved by RP HPLC on Synergy 4 micron Hydro-RP column (Phenominex). A linear gradient of methanol from 0 to 30% in 50 mM triethylammonium acetate buffer (pH 7.5) was used for elution. The corresponding fractions were combined, concentrated and lyophilized 3 times to remove excess of buffer.

| Structure | MS [M − 1] | P(α) | P(β) | P(γ) |
|---|---|---|---|---|
| 15 | 533.1 | −7.23(d) | −22.50(t) | −11.70(d) |
| 16 | 532.4 | −10.75(d) | −23.18(t) | −11.76(d) |
| 18 | 539.6 | −9.69(d) | −23.15(t) | −11.91(d) |
| 19 | 533.3 | −11.02(d) | −23.43(t) | −12.00(d) |
| 20 | 576.1 | −7.39(s) | −22.50(br.s) | −11.86(s) |

-continued

| Structure | MS [M − 1] | P(α) | P(β) | P(γ) |
|---|---|---|---|---|
| 21 | 516.1 | −7.39(s) | −22.49(br.s) | −11.74(s) |
| 22 | 508.4 | −10.15(br.s) | −23.01(br.s) | −12.09(d) |
| 23 | 510.1 | −9.09(d) | −22.86(t) | −11.82(d) |
| 24 | 512.1 | −10.67(br.s) | −23.06(br.s) | −11.51(d) |
| 25 | 526.2 | −10.28(br.s) | −22.82(br.s) | −11.48(d) |

|  | Structure | MS [M − 1] | P(α) | P(β) | P(γ) |
|---|---|---|---|---|---|
| 27 | (structure: triphosphate-5'-O-sugar with 4'-CH2F, 3'-OH, 2'-N3, uracil base) | 540.6 | −8.21(d) | −22.69(t) | −11.75(d) |
| 47 | (structure: triphosphate-5'-O-sugar with 4'-CH2F, 3'-OH, 2'-CH3, cytosine base) | 512.2 | −10.01(d) | −22.23(br.s) | −11.48(s) |
| 48 | (structure: triphosphate-5'-O-sugar with 4'-CH2F, 3'-OH, 2'-C≡CH, cytosine base) | 522.3 | −11.50(br.s) | −21.68(br.s) | −11.50(br.s) |
| 49 | (structure: triphosphate-5'-O-sugar with 4'-CH2F, 3'-OH, 2'-CH3, uracil base) | 513.0 | −9.70(s) | −22.68(s) | −11.65(s) |
| 50 | (structure: triphosphate-5'-O-sugar with 4'-CH2F, 3'-OH, 2'-CH2F, cytosine base) | 529.8 | −10.55(br.s) | −22.90(br.s) | −11.72(br.s) |

| Structure | MS [M − 1] | P(α) | P(β) | P(γ) |
|---|---|---|---|---|
| 51 | 531.2 | −11.49(br.s) | −22.66(br.s) | −11.49(br.s) |
| 52 | 532.3 | −10.63(br.s) | −22.95(t) | −11.92(d) |
| 53 | 514.1 | −10.78(br.s) | −23.16(t) | −11.78(d) |
| 54 | 516.1 | −10.87(d) | −23.17(t) | −11.83(d) |
| 55 | 523.5 | −10.79(s) | −23.09(s) | −11.87(d) |

Example A

Picornavirus Assay

HeLa-OHIO cells (Sigma-Aldrich, St. Louis, Mo.) were plated in 96 well plates at a density of $1.5 \times 10^5$ cells per well in assay media (MEM without phenol red or L-glutamine, supplemented with 1% FBS, 1% penicillin/streptomycin, 2 mM GlutaGro, and 1×MEM nonessential amino acids, all from Cellgro, Manassas, Va.). Assay setup took place after allowing cells to adhere for 24 h. Compounds dissolved in DMSO were serially diluted in assay media to 2× final concentration. Media was aspirated from the cells, and 100 μl media with compound was added in triplicate. Human rhinovirus 1B (ATCC, Manassas, Va.) was diluted in assay media, and 100 µL was added to cells and compound. The virus inoculum was selected to cause 80-90% cytopathic effect in 4 d. Infected cells were incubated for 4 d at 33° C., 5% $CO_2$. To develop the assay, 100 µL media was replaced with 100 µL CellTiter-Glo® reagent (Promega, Madison, Wis.), and incubated for 10 mins at RT. Luminescence was measured on a Victor X3 multi-label plate reader.

Compounds of Formula (I) are active in this assay. The antiviral activity of exemplary compounds is shown in Table 2, where 'A' indicates an $EC_{50}$<1 µM, 'B' indicates an $EC_{50}$≥1 µM and <10 µM, and 'C' indicates an $EC_{50}$≥10 µM and <100 µM.

TABLE 2

| Compound # | $EC_{50}$ |
|---|---|
| 2 | B |
| 3 | A |
| 4 | A |
| 7 | A |
| 9 | A |
| 10 | B |
| 37 | A |

HeLa-OHIO cells (Sigma-Aldrich, St. Louis, Mo.) were plated in 96 well plates at a density of 1.5×10$^5$ cells per well in assay media (MEM without phenol red or L-glutamine, supplemented with 1% FBS, 1% penicillin/streptomycin, 2 mM GlutaGro, and 1×MEM nonessential amino acids, all from Cellgro, Manassas, Va.). Assay setup took place after allowing cells to adhere for 24 h. Compounds dissolved in DMSO were serially diluted in assay media to 2× final concentration. Media was aspirated from the cells, and 100 µl media with compound was added in triplicate. Cells were pre-incubated with the diluted compounds for 24 h before infection. Human rhinovirus 1B (ATCC, Manassas, Va.) was diluted in assay media, and 100 µL was added to cells and compound. The virus inoculum was selected to cause 80-90% cytopathic effect in 4 d. Infected cells were incubated for 4 d at 33° C., 5% $CO_2$. To develop the assay, 100 µL media was replaced with 100 µL CellTiter-Glo® reagent (Promega, Madison, Wis.), and incubated for 10 mins at RT. Luminescence was measured on a Victor X3 multi-label plate reader.

Compounds of Formula (I) are active in this assay. The antiviral activity of exemplary compounds is shown in Table 3, where 'A' indicates an $EC_{50}$<1 µM, 'B' indicates an $EC_{50}$≥1 µM and <10 µM, and 'C' indicates an $EC_{50}$≥10 µM and <100 µM.

TABLE 3

| Compound # | $EC_{50}$ |
|---|---|
| 41 | B |
| 42 | C |
| 44 | C |
| 45 | B |

Example B

Picornavirus Polymerase Inhibition Assay

The enzyme activity of human rhinovirus 16 polymerase (HRV16pol) was measured as an incorporation of tritiated NMP into acid-insoluble RNA products. HRV16pol assay reactions contained 30 Nm recombinant enzyme, 50 Nm heteropolymeric RNA, about 0.5 µCi tritiated NTP, 0.1 Mm of competing cold NTP, 40 Mm Tris-HCl (Ph 7.0), 3 Mm dithiothreitol, and 0.5 Mm $MgCl_2$. Standard reactions were incubated for 2.5 h at 30° C., in the presence of increasing concentration of inhibitor. At the end of the reaction, RNA was precipitated with 10% TCA, and acid-insoluble RNA products were filtered on a size exclusion 96-well plate. After washing of the plate, scintillation liquid was added and radiolabeled RNA products were detected according to standard procedures with a Trilux Microbeta scintillation counter. The compound concentration at which the enzyme-catalyzed rate was reduced by 50% ($IC_{50}$) was calculated by fitting the data to a non-linear regression (sigmoidal).

The $IC_{50}$ values were derived from the mean of several independent experiments and are shown in Table 4. Compounds of Formula (I) showed activity in this assay. A value of 'A' in the table below indicates an $IC_{50}$ of <5 µM, a value of '3' indicates an $IC_{50}$<20 µM, and a value of 'C' indicates an $IC_{50}$ value of <100 µM.

TABLE 4

| Compound # | $IC_{50}$ |
|---|---|
| 16 | C |
| 18 | B |
| 19 | A |
| 20 | C |
| 21 | A |
| 22 | B |
| 23 | A |
| 24 | A |
| 47 | A |
| 48 | A |
| 50 | B |
| 52 | A |
| 53 | A |
| 54 | A |

Example C

Enterovirus Assay

Cells

HeLa OHIO cells are purchased from Sigma Aldrich (St Louis, Mo.) and cultured in MEM with Glutamax (Gibco cat. #41090) supplemented with 10% FBS (Mediatech cat. #35-011-CV) and 1% penicillin/streptomycin (Mediatech cat. #30-002-CI), at 37° C. with 5% $CO_2$. RD cells are purchased from ATCC (Manassas, Va.) and cultured in DMEM, supplemented with 10% FBS (Mediatech cat. #35-011-CV) and 1% penicillin/streptomycin (Mediatech cat. #30-002-CI), at 37° C. with 5% $CO_2$.

Determination of Anti-Enterovirus Activity

For HRV16, EV68, and CVB3, HeLa-OHIO cells are plated at a density of 1.5×10$^5$ cells per mL (1.5×10$^4$ cells per well) in assay media (MEM without phenol red or L-glutamine (Gibco cat. #51200) supplemented with 1% FBS, 1% penicillin/streptomycin (Mediatech cat. #30-002-CI), and 1% Glutamax (Gibco cat. #35050)) in clear-bottom black 96 well plates. For EV71, RD cells are plated at a density of 5×10$^4$ cells per mL (5000 cells per well) in assay media (DMEM supplemented with 2% FBS and 1% penicillin/streptomycin). After 24 h, media is removed and replaced with serially diluted compounds in assay media. For $EC_{50}$ measurements, cells are infected in 100 µL assay media with a virus inoculum sufficient to obtain a 10-fold reduction of the cell viability in the infected control compared to uninfected control cells. After 2-6 days, cell viability is measured using CellTiter Glo Luminescent Cell Viability Assay (Promega cat. #G7572). Cells infected with EV-71 and CVB3 are cultured at 37° C., while cells infected with HRV-16 or EV-68 are cultured at 33° C. 100 μL media is removed from each well and 100 μL CellTiter Glo reagent was added. Plates are incubated at RT for 5 mins, then luminescence is measured using a Perkin Elmer multilabel counter Victor3V. $EC_{50}$ values is determined using XLFit.

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A compound of Formula (I), or a pharmaceutically acceptable salt thereof,

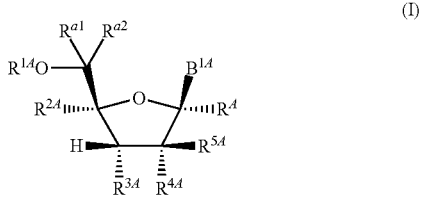

wherein:

$B^{1A}$ is an optionally substituted heterocyclic base or an optionally substituted heterocyclic base with a protected amino group;

$R^A$ is hydrogen or deuterium;

$R^{a1}$ and $R^{a2}$ are independently hydrogen or deuterium;

$R^{1A}$ is selected from the group consisting of hydrogen, an optionally substituted acyl, an optionally substituted O-linked amino acid,

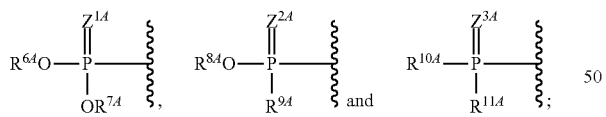

$R^{2A}$ is an unsubstituted $C_{2-4}$ alkyl, $-CHF_2$, $-(CH_2)_{1-6}Cl$, $-(CH_2)_{1-6}Br$, a $C_{1-6}$ azidoalkyl or a $C_{1-6}$ aminoalkyl; and $R^{5A}$ is halogen, $N_3$, OH, an optionally substituted $C_{1-6}$ alkyl, an optionally substituted $C_{2-6}$ alkenyl or an optionally substituted $C_{2-6}$ alkynyl; or $R^{1A}$ is hydrogen;

$R^{2A}$ is an unsubstituted $C_{2-4}$ alkenyl, an unsubstituted $C_{2-4}$ alkynyl or $-(CH_2)_{1-6}F$; and $R^{5A}$ is chloro or $N_3$; or $R^{1A}$ is selected from the group consisting of an optionally substituted acyl, an optionally substituted O-linked amino acid,

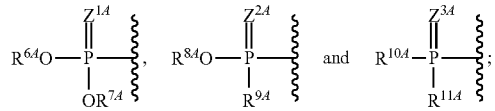

$R^{2A}$ is an unsubstituted $C_{2-4}$ alkenyl, an unsubstituted $C_{2-4}$ alkynyl or $-(CH_2)_{1-6}F$; and $R^{5A}$ is hydrogen, deuterium, fluoro, an optionally substituted $C_{1-6}$ alkyl, an optionally substituted $C_{2-6}$ alkenyl or an optionally substituted $C_{2-6}$ alkynyl;

$R^{3A}$ is selected from the group consisting of hydrogen, deuterium, halo, OH, $-OC(=O)R^{nA}$ and an optionally substituted O-linked amino acid;

$R^{4A}$ is hydrogen or deuterium;

$R^{6A}$, $R^{7A}$ and $R^{8A}$ are independently selected from the group consisting of absent, hydrogen, an optionally substituted $C_{1-24}$ alkyl, an optionally substituted $C_{3-24}$ alkenyl, an optionally substituted $C_{3-24}$ alkynyl, an optionally substituted $C_{3-6}$ cycloalkyl, an optionally substituted $C_{3-6}$ cycloalkenyl, an optionally substituted aryl, an optionally substituted heteroaryl, an optionally substituted aryl($C_{1-6}$ alkyl), an optionally substituted $*-(CR^{15A}R^{16A})_p-O-C_{1-24}$ alkyl, an optionally substituted $*-(CR^{17A}R^{18A})_q-O-C_{1-24}$ alkenyl,

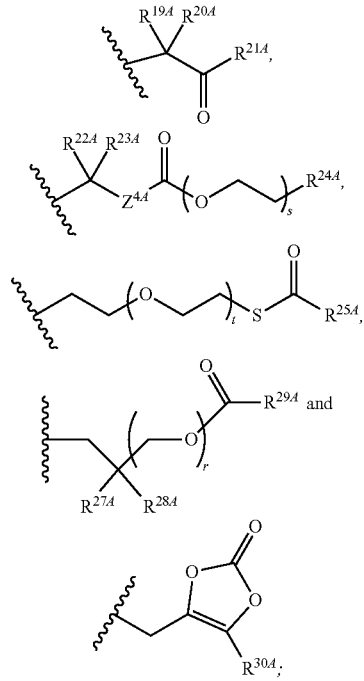

$R^{6A}$ is

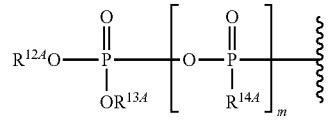

and $R^{7A}$ is absent or hydrogen; or $R^{6A}$ and $R^{7A}$ are taken together to form a moiety selected from the group consisting of an optionally substituted

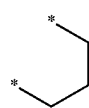

and an optionally substituted

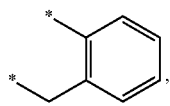

wherein the oxygens connected to $R^{6A}$ and $R^{7A}$, the phosphorus and the moiety form a six-membered to ten-membered ring system;

$R^{9A}$ is selected from the group consisting of an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, $NR^{31A}R^{32A}$, an optionally substituted N-linked amino acid and an optionally substituted N-linked amino acid ester derivative;

$R^{10A}$ and $R^{11A}$ are independently an optionally substituted N-linked amino acid or an optionally substituted N-linked amino acid ester derivative;

$R^{12A}$ and $R^{13A}$ are independently absent or hydrogen;

$R^{14A}$ is $O^-$, OH or methyl;

each $R^{15A}$, each $R^{16A}$, each $R^{17A}$ and each $R^{18A}$ are independently hydrogen, an optionally substituted $C_{1-24}$ alkyl or alkoxy;

$R^{19A}$, $R^{20A}$, $R^{22A}$ and $R^{23A}$ are independently selected from the group consisting of hydrogen, an optionally substituted $C_{1-24}$ alkyl and an optionally substituted aryl;

$R^{21A}$ and $R^{24A}$ are independently selected from the group consisting of hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl, an optionally substituted —O-monocyclic heterocyclyl and

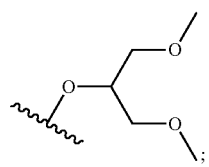 [SMILES: *OC(COC)COC]

$R^{25A}$ and $R^{30A}$ are independently selected from the group consisting of hydrogen, an optionally substituted $C_{1-24}$ alkyl and an optionally substituted aryl;

$R^{27A}$ and $R^{28A}$ are independently —C≡N or an optionally substituted substituent selected from the group consisting of $C_{2-8}$ organylcarbonyl, $C_{2-8}$ alkoxycarbonyl and $C_{2-8}$ organylaminocarbonyl;

$R^{29A}$ is selected from the group consisting of hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl;

$R^{31A}$ and $R^{32A}$ are independently selected from the group consisting of hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl and an optionally substituted aryl($C_{1-4}$ alkyl);

$R'''^A$ is an optionally substituted $C_{1-24}$ alkyl;

m and t are independently 0 or 1;

p and q are independently selected from the group consisting of 1, 2 and 3;

s is 0, 1, 2 or 3;

r is 1 or 2; and $Z^{1A}$, $Z^{2A}$, $Z^{3A}$ and $Z^{4A}$ are independently O or S.

2. The compound of claim 1, wherein $R^{2A}$ is an unsubstituted $C_{2-4}$ alkyl, an unsubstituted $C_{2-4}$ alkenyl or an unsubstituted $C_{2-4}$ alkynyl.

3. The compound of claim 1, wherein $R^{2A}$ is —$CHF_2$, —$(CH_2)_{1-6}Cl$ or —$(CH_2)_{1-6}Br$.

4. The compound of claim 1, wherein $R^{2A}$ is a $C_{1-6}$ azidoalkyl or $C_{1-6}$ aminoalkyl.

5. The compound of claim 1, wherein $R^{1A}$ is

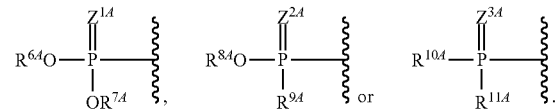

6. The compound of claim 5, wherein $R^{6A}$ and $R^{7A}$ are both hydrogen or both absent.

7. The compound of claim 5, wherein both $R^{6A}$ and $R^{7A}$ are independently selected from the group consisting of an optionally substituted $C_{1-24}$ alkyl, an optionally substituted $C_{3-24}$ alkenyl, an optionally substituted $C_{3-24}$ alkynyl, an optionally substituted $C_{3-6}$ cycloalkyl, an optionally substituted $C_{3-6}$ cycloalkenyl, an optionally substituted aryl, an optionally substituted heteroaryl, an optionally substituted aryl($C_{1-6}$ alkyl), *—$(CR^{15A}R^{16A})_p$—O—$C_{1-24}$ alkyl, *—$(CR^{17A}R^{18A})_q$—O—$C_{2-24}$ alkenyl, an optionally substituted aryl and an optionally substituted aryl($C_{1-6}$ alkyl).

8. The compound of claim 5, wherein $R^{6A}$ and $R^{7A}$ are both

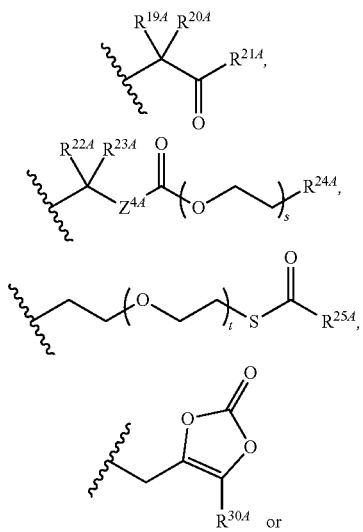

-continued

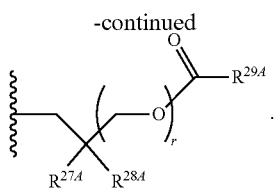

9. The compound of claim 5, wherein $R^{6A}$ and $R^{7A}$ are taken together to form a moiety selected from the group consisting of an optionally substituted

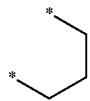

and an optionally substituted

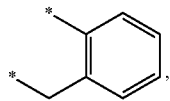

wherein the oxygens connected to $R^{6A}$ and $R^{7A}$, the phosphorus and the moiety form a six-membered to ten-membered ring system.

10. The compound of claim 5, wherein $R^{8A}$ is an optionally substituted aryl; and $R^{9A}$ is an optionally substituted N-linked amino acid or an optionally substituted N-linked amino acid ester derivative.

11. The compound of claim 5, wherein $R^{10A}$ and $R^{11A}$ are both an optionally substituted N-linked amino acid or an optionally substituted N-linked amino acid ester derivative.

12. The compound of claim 1, wherein $R^{1A}$ is

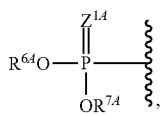

$R^{6A}$ is

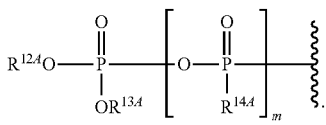

and $R^{7A}$ is absent or hydrogen.

13. The compound of claim 12, wherein m is 0; and $R^{7A}$, $R^{12A}$ and $R^{13A}$ are independently absent or hydrogen.

14. The compound of claim 12, wherein m is 1; $R^{7A}$, $R^{12A}$ and $R^{13A}$ are independently absent or hydrogen; and $R^{14A}$ is O⁻ or OH.

15. The compound of claim 12, wherein m is 1; $R^{7A}$, $R^{12A}$ and $R^{13A}$ are independently absent or hydrogen; and $R^{14A}$ is methyl.

16. The compound of claim 1, wherein $R^{1A}$ is H.

17. The compound of claim 1, wherein $R^{1A}$ is an optionally substituted acyl or an optionally substituted O-linked amino acid.

18. The compound of claim 1, wherein $B^{1A}$ is selected from the group consisting of:

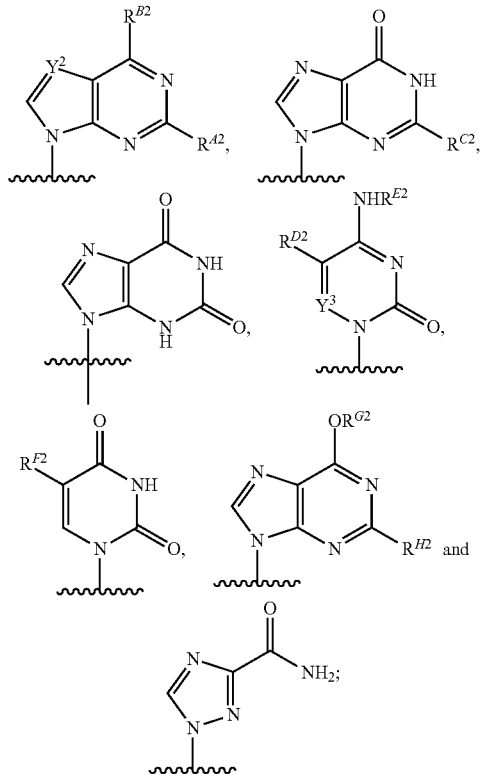

wherein:
$R^{A2}$ is selected from the group consisting of hydrogen, halogen and NHR$^{J2}$, wherein $R^{J2}$ is selected from the group consisting of hydrogen, —C(=O)R$^{K2}$ and —C(=O)OR$^{L2}$;
$R^{B2}$ is halogen or NHR$^{W2}$, wherein $R^{W2}$ is selected from the group consisting of hydrogen, an optionally substituted $C_{1-6}$ alkyl, an optionally substituted $C_{2-6}$ alkenyl, an optionally substituted $C_{3-8}$ cycloalkyl, —C(=O)R$^{M2}$ and —C(=O)OR$^{N2}$;
$R^{C2}$ is hydrogen or NHR$^{O2}$, wherein $R^{O2}$ is selected from the group consisting of hydrogen, —C(=O)R$^{P2}$ and —C(=O)OR$^{Q2}$;
$R^{D2}$ is selected from the group consisting of hydrogen, deuterium, halogen, an optionally substituted $C_{1-6}$ alkyl, an optionally substituted $C_{2-6}$ alkenyl and an optionally substituted $C_{2-6}$ alkynyl;
$R^{E2}$ is selected from the group consisting of hydrogen, hydroxy, an optionally substituted $C_{1-6}$ alkyl, an optionally substituted $C_{3-8}$ cycloalkyl, —C(=O)R$^{R2}$ and —C(=O)OR$^{S2}$;
$R^{F2}$ is selected from the group consisting of hydrogen, halogen, an optionally substituted $C_{1-6}$ alkyl, an optionally substituted $C_{2-6}$ alkenyl and an optionally substituted $C_{2-6}$ alkynyl;
$Y^2$ and $Y^3$ are independently N or CR$^{I2}$, wherein $R^{I2}$ is selected from the group consisting of hydrogen, halogen, an optionally substituted $C_{1-6}$-alkyl, an optionally substituted $C_{2-6}$-alkenyl and an optionally substituted $C_{2-6}$-alkynyl;
$R^{G2}$ is an optionally substituted $C_{1-6}$ alkyl;

$R^{H2}$ is hydrogen or $NHR^{T2}$, wherein $R^{T2}$ is independently selected from the group consisting of hydrogen, —C(=O)$R^{U2}$ and —C(=O)O$R^{V2}$; and $R^{K2}$, $R^{L2}$, $R^{M2}$, $R^{N2}$, $R^{P2}$, $R^{Q2}$, $R^{R2}$, $R^{S2}$, $R^{U2}$ and $R^{V2}$ are independently selected from the group consisting of $C_{1-6}$ alkyl, $C_{2-6}$ alkenyl, $C_{2-6}$ alkynyl, $C_{3-6}$ cycloalkyl, $C_{3-6}$ cycloalkenyl, $C_{6-10}$ aryl, heteroaryl, heterocyclyl, aryl($C_{1-6}$ alkyl), heteroaryl($C_{1-6}$ alkyl) and heterocyclyl ($C_{1-6}$ alkyl).

19. The compound of claim 18, wherein $B^{1A}$ is

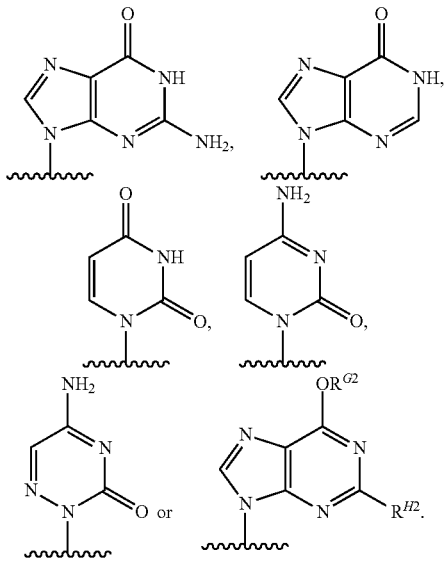

20. The compound of claim 1, wherein $R^{3A}$ is hydrogen or deuterium.
21. The compound claim 1, wherein $R^{3A}$ is halo.
22. The compound of claim 1, wherein $R^{3A}$ is OH.
23. The compound of claim 1, wherein $R^{3A}$ is —OC(=O)$R^{nA}$ or an optionally substituted O-linked amino acid.
24. The compound of claim 1, wherein $R^{4A}$ is hydrogen.
25. The compound of claim 1, wherein $R^{5A}$ is hydrogen or deuterium.
26. The compound of claim 1, wherein $R^{5A}$ is halogen.
27. The compound of claim 1, wherein $R^{5A}$ is $N_3$.
28. The compound of claim 1, wherein $R^{5A}$ is OH.
29. The compound of claim 1, wherein $R^{5A}$ is an optionally substituted $C_{1-6}$ alkyl.
30. The compound of claim 1, wherein $R^{5A}$ is an optionally substituted $C_{2-6}$ alkenyl.
31. The compound of claim 1, wherein $R^{5A}$ is an optionally substituted $C_{2-6}$ alkynyl.
32. The compound of claim 1, wherein the compound of Formula (I) is selected from the group consisting of:

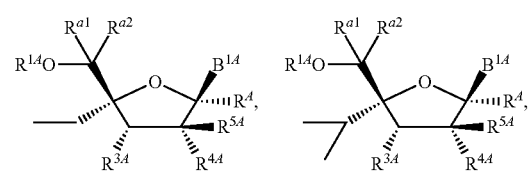

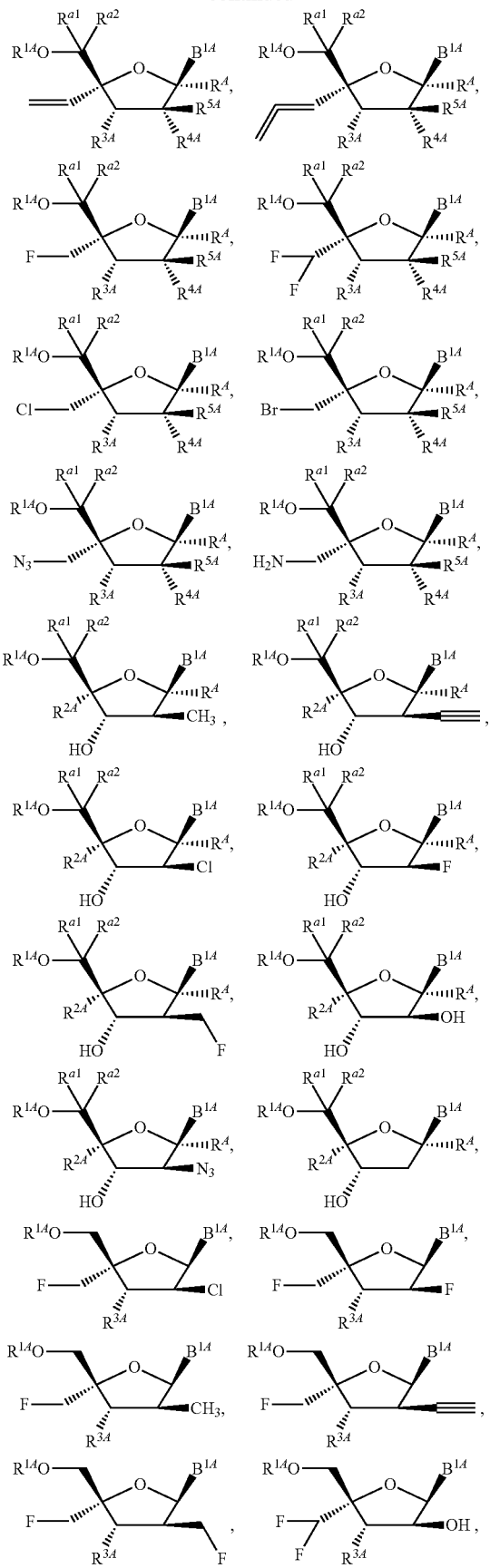

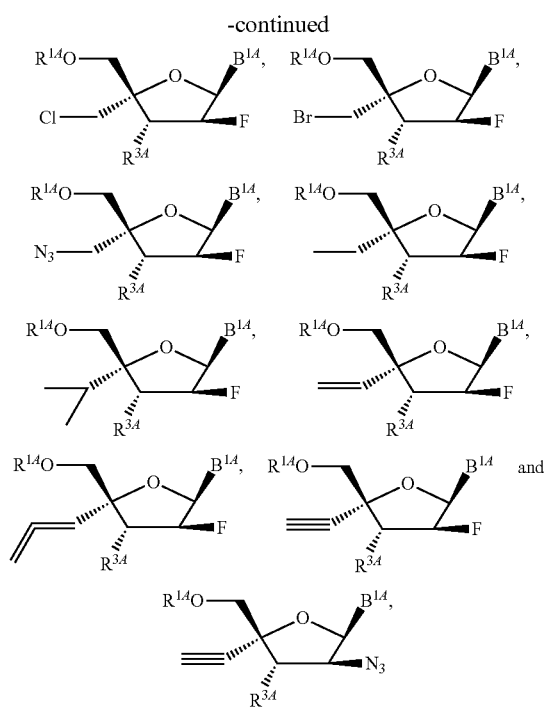
or a pharmaceutically acceptable salt of any of the foregoing.
33. A compound of Formula (I) selected from the group consisting of:
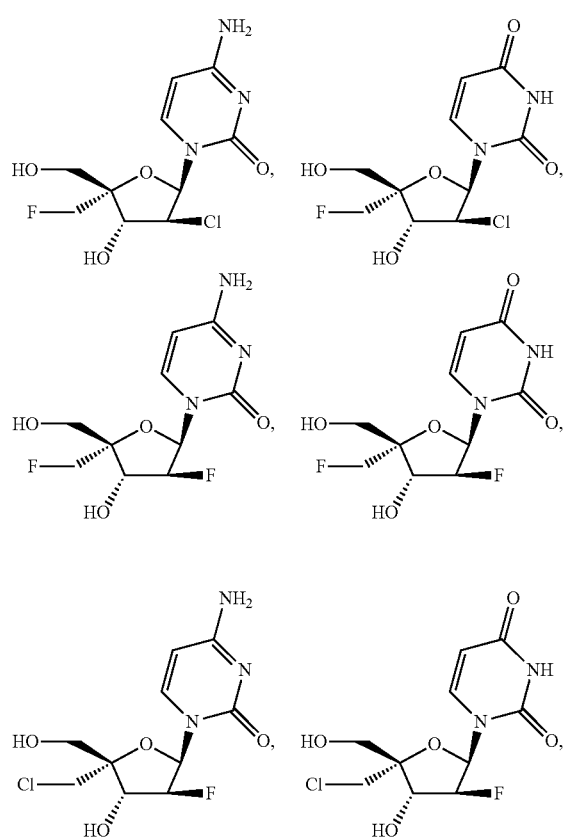
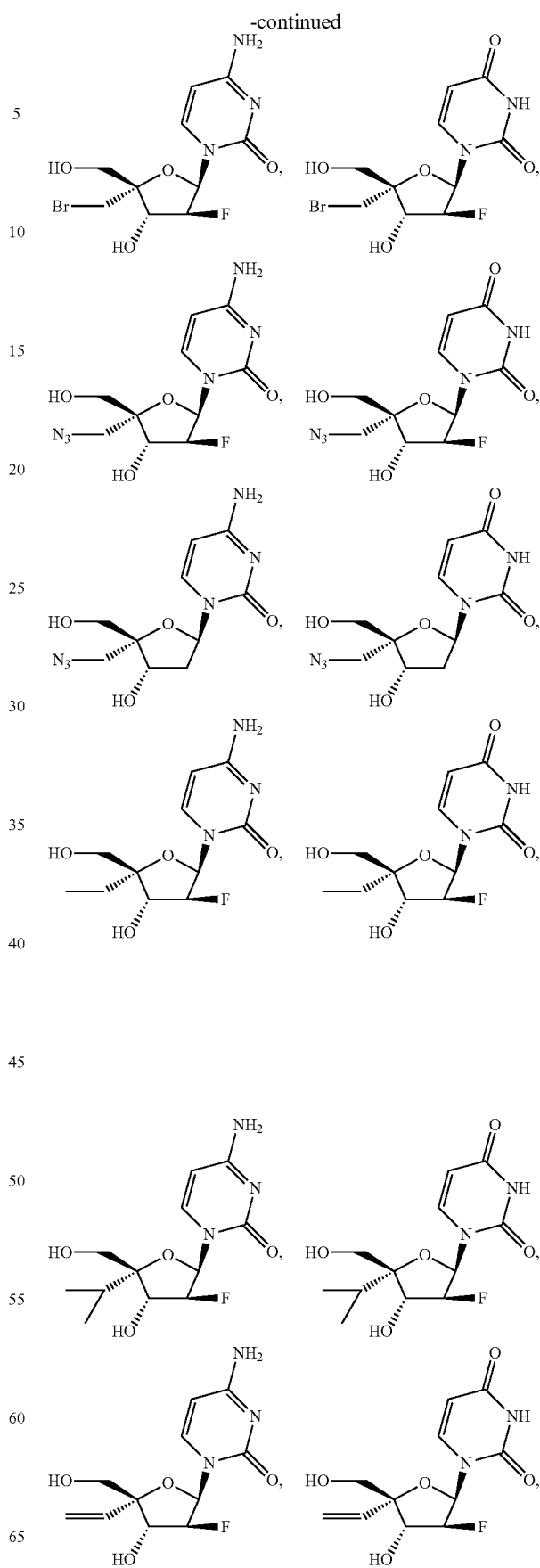

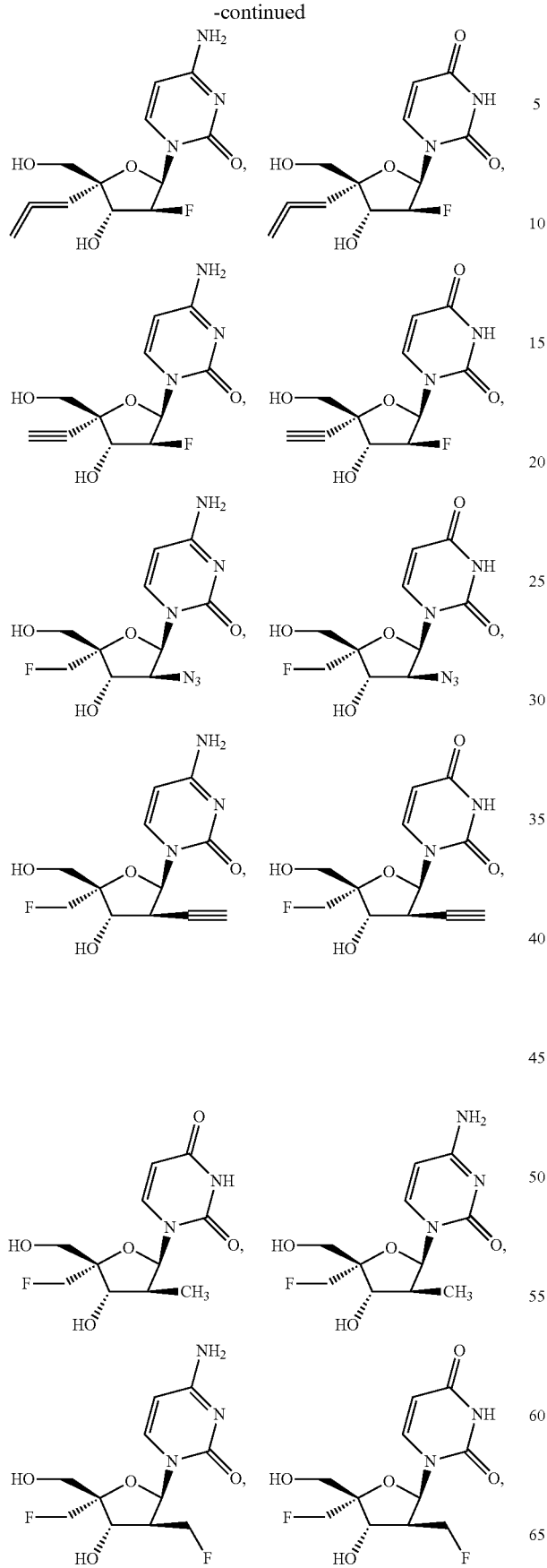
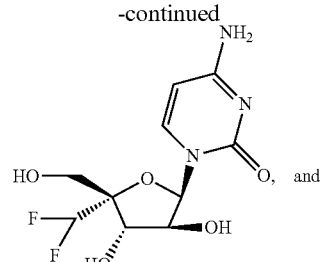
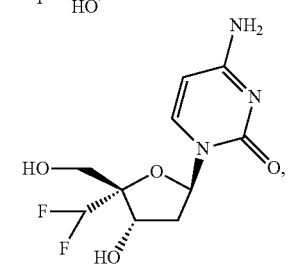
or a pharmaceutically acceptable salt of any of the foregoing.
34. A compound of Formula (I) selected from the group consisting of:
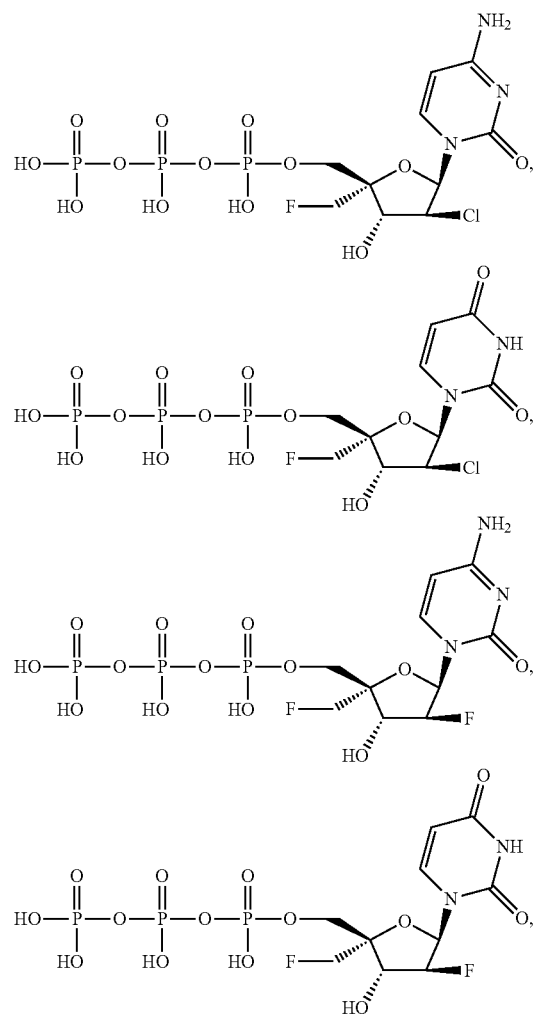

137
-continued
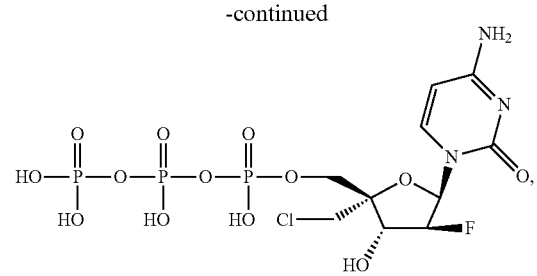
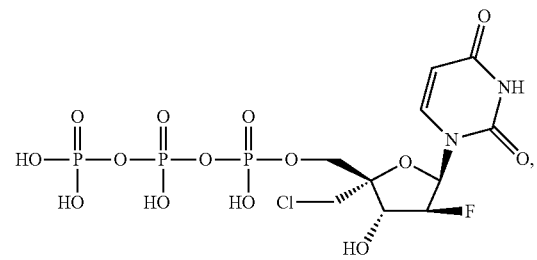
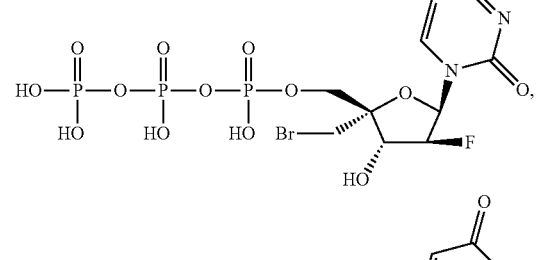
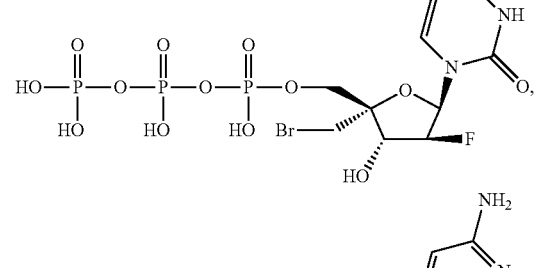
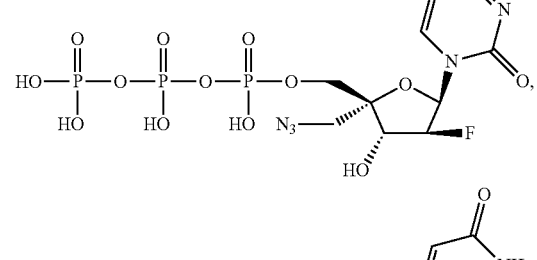
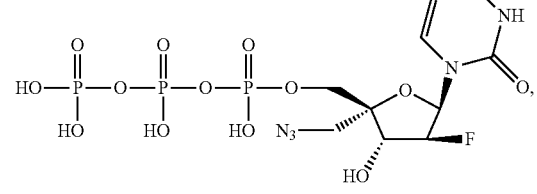
138
-continued
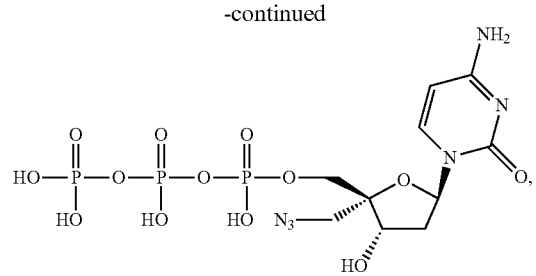
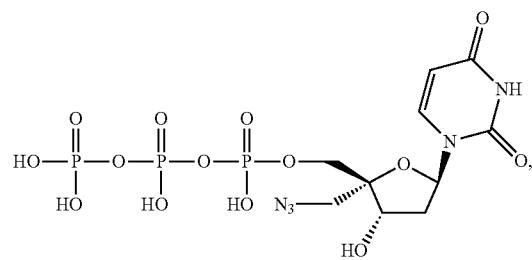
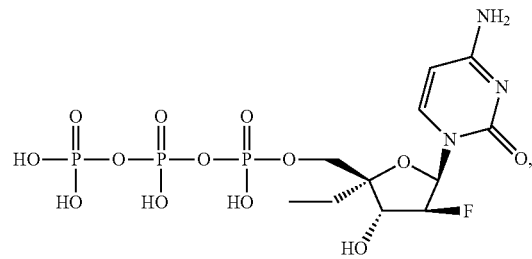
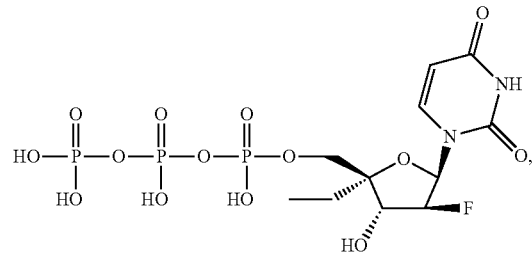
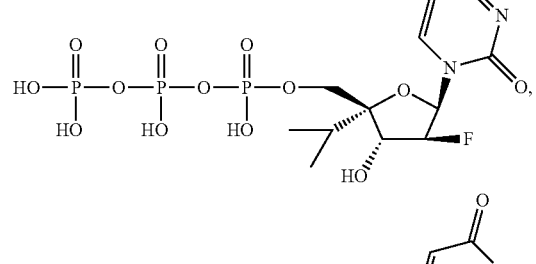
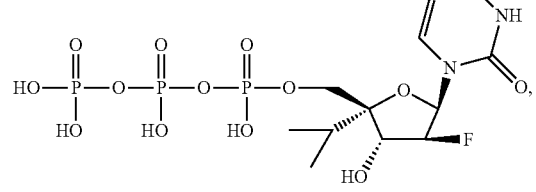

139
-continued
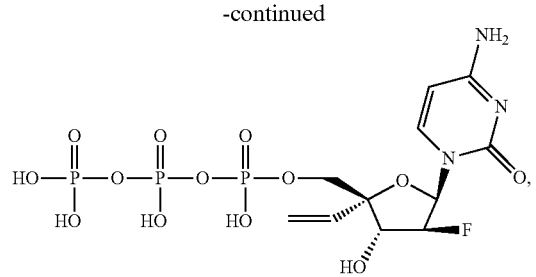
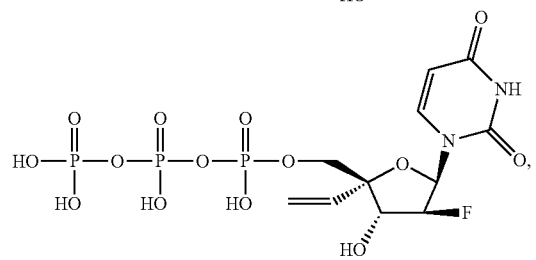
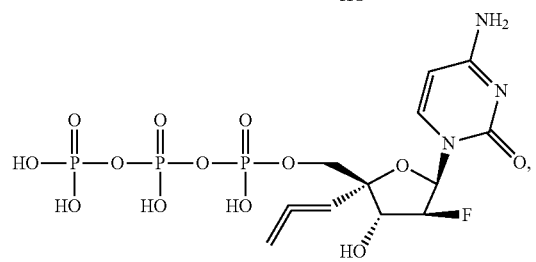
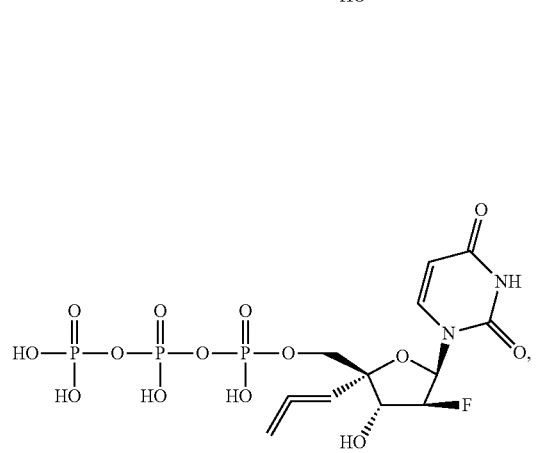
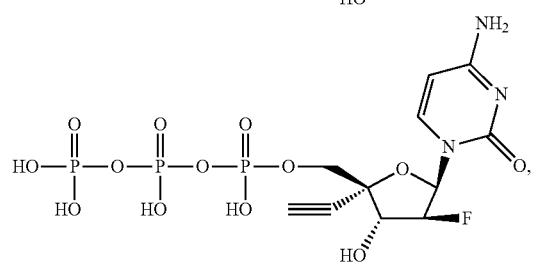
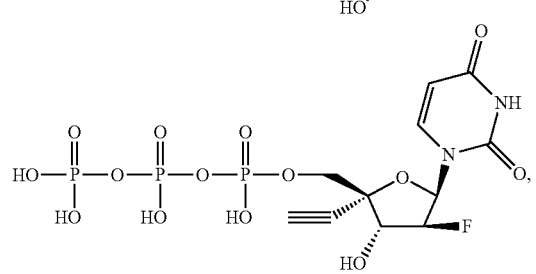
140
-continued
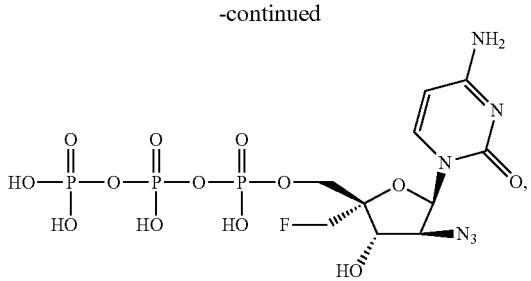
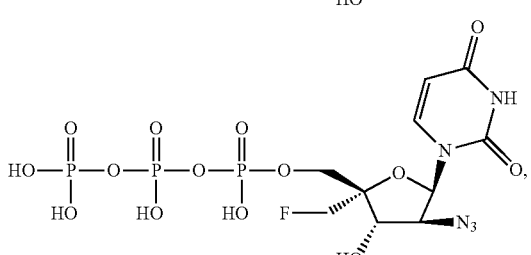
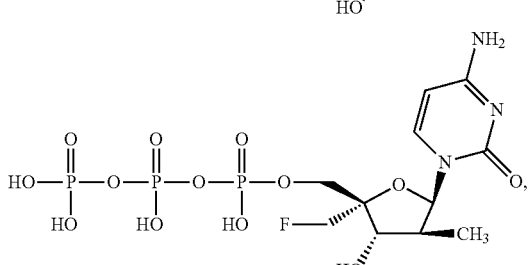
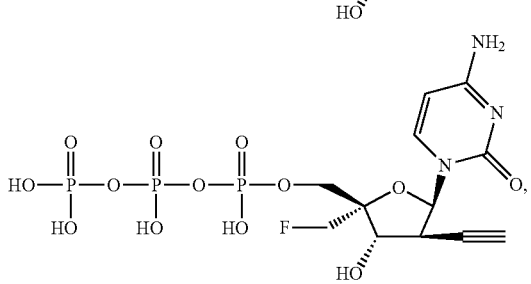
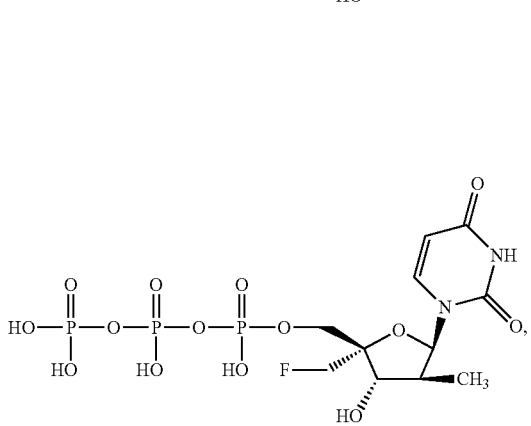
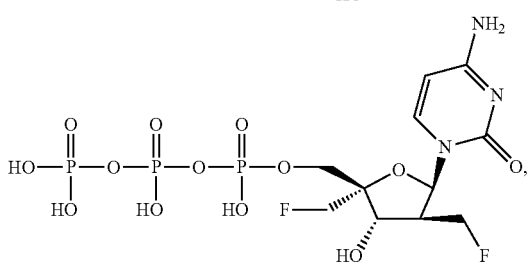

-continued

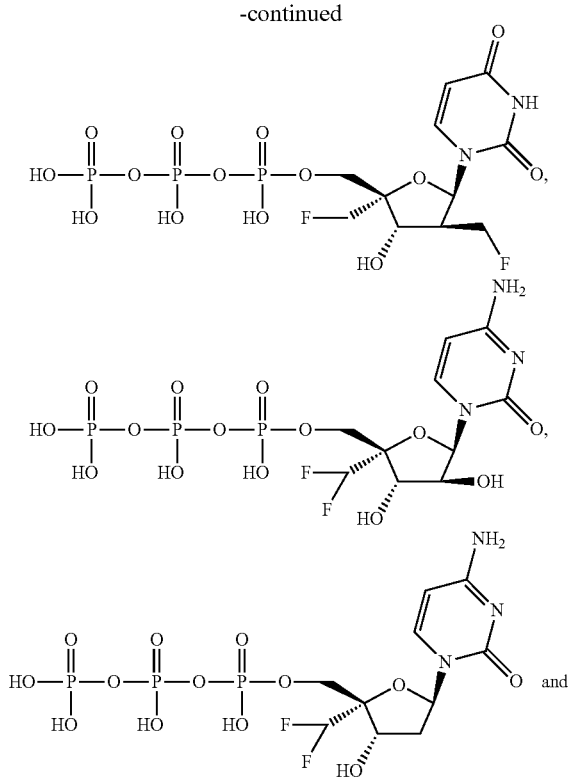

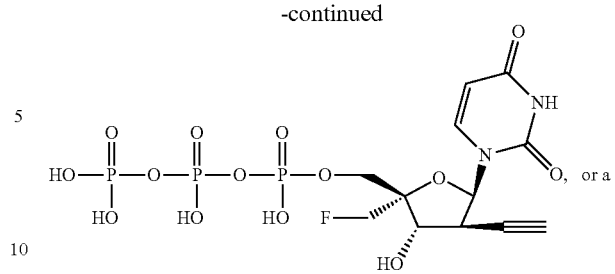, or a pharmaceutically acceptable salt of any of the foregoing.

35. A pharmaceutical composition comprising an effective amount of a compound of claim 1, or a pharmaceutically acceptable salt thereof, and a pharmaceutically acceptable carrier, diluent, excipient, or combination thereof.

36. A method for inhibiting replication of a picornavirus comprising contacting a cell infected with the picornavirus with an effective amount of a compound of claim 1, or a pharmaceutically acceptable salt thereof.

37. A method for ameliorating or treating a picornavirus viral infection comprising contacting a cell infected with the picornavirus in a subject identified as suffering from the viral infection with an effective amount of a compound of claim 1, or a pharmaceutically acceptable salt thereof.

38. The compound of claim 1, wherein $R^{2A}$ is —$(CH_2)_{1-6}F$.

* * * * *

UNITED STATES PATENT AND TRADEMARK OFFICE
CERTIFICATE OF CORRECTION

PATENT NO. : 9,890,188 B2
APPLICATION NO. : 14/971926
DATED : February 13, 2018
INVENTOR(S) : Guangyi Wang et al.

It is certified that error appears in the above-identified patent and that said Letters Patent is hereby corrected as shown below:

In the Specification

In Column 15 at Line 22 (Approx.), Change "NR" to --$NR^{31A}R^{32A}$,--.

In Column 17 at Line 58 (Approx.), Change "at least one" to --both--.

Signed and Sealed this
Twentieth Day of November, 2018

Andrei Iancu
*Director of the United States Patent and Trademark Office*

CERTIFICATE OF CORRECTION (continued)
U.S. Pat. No. 9,890,188 B2

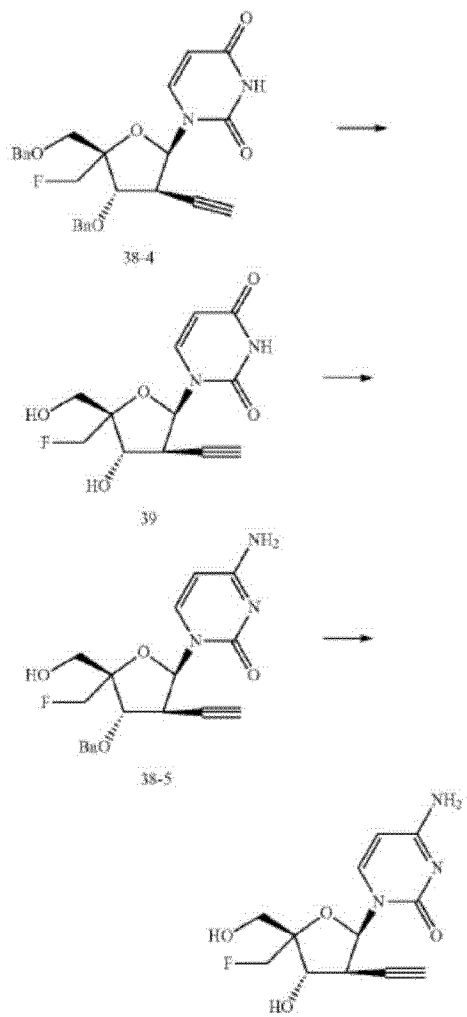

In Column 96 at Lines 15-55 (Approx.), Change "

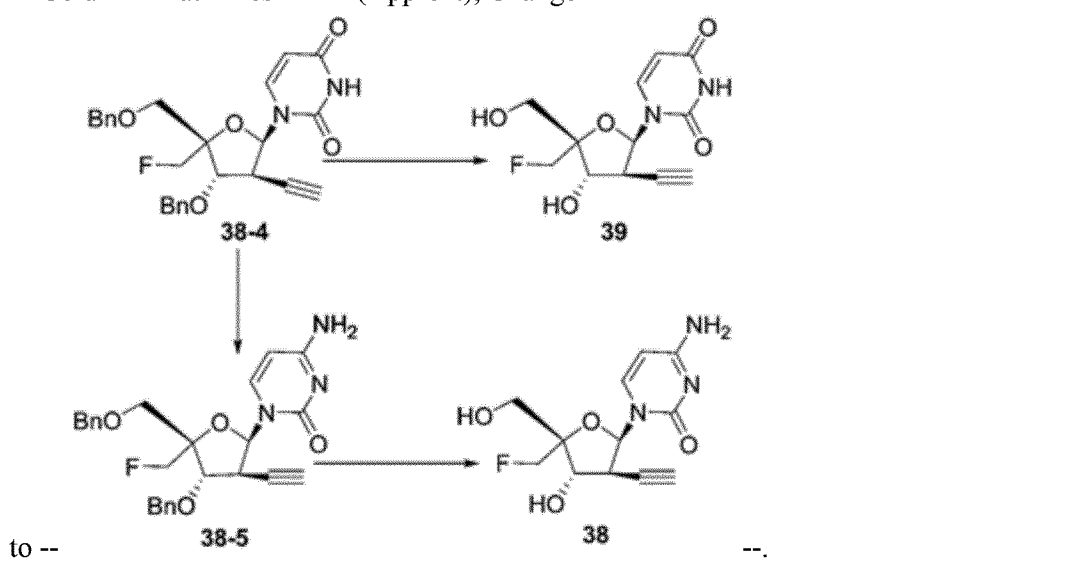

to --             --.

CERTIFICATE OF CORRECTION (continued)
U.S. Pat. No. 9,890,188 B2

Page 3 of 3

In Column 104 at Lines 1-12 (Approx.), Change " 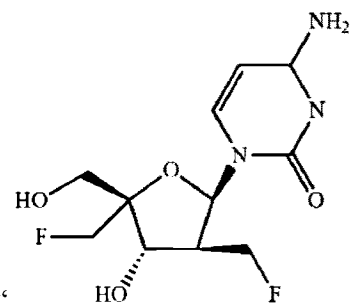 "

to -- 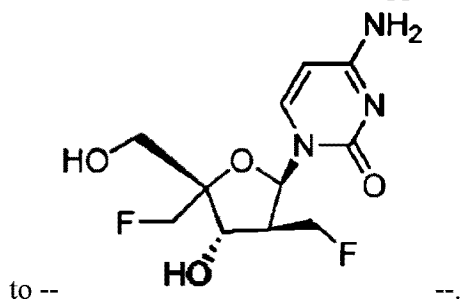 --.

In Column 124 at Line 19, Change "13'''" to --` B'--.

In the Claims

In Column 129 at Lines 39-43 (Approx.), In Claim 12, change

" 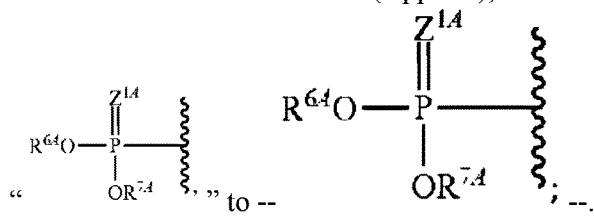 " to -- 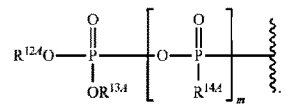 ; --.

In Column 129 at Lines 49-53 (Approx.), In Claim 12, change "

to -- 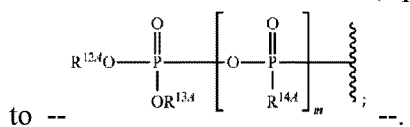 --.

In Column 130 at Line 38, In Claim 18, change "$NHR^{12}$," to --$NHR^{J2}$,--.

In Column 130 at Line 41, In Claim 18, change "$R^{w2}$" to --$R^{W2}$--.